US012629035B2

(12) United States Patent (10) Patent No.: US 12,629,035 B2

Spahn et al. (45) Date of Patent: *May 19, 2026

(54) METHOD OF MONITORING THE STATUS OF A WOUND

(71) Applicant: WoundVision, LLC, Indianapolis, IN (US)

(72) Inventors: James G. Spahn, Carmel, IN (US); Nicholas A. McMurray, Indianapolis, IN (US)

(73) Assignee: WoundVision, LLC, Indianapolis, IN (US)

( * ) Notice: Subject to any disclaimer, the term of this patent is extended or adjusted under 35 U.S.C. 154(b) by 1333 days.

This patent is subject to a terminal disclaimer.

(21) Appl. No.: 16/255,743

(22) Filed: Jan. 23, 2019

(65) Prior Publication Data

US 2019/0167117 A1 Jun. 6, 2019

Related U.S. Application Data

(63) Continuation of application No. 15/727,729, filed on Oct. 9, 2017, now abandoned, and a continuation of (Continued)

(51) Int. Cl.
| | |
|---|---|
| *A61B 5/01* | (2006.01) |
| *A61B 5/00* | (2006.01) |

(Continued)

(52) U.S. Cl.
CPC ............ *A61B 5/015* (2013.01); *A61B 5/7425* (2013.01); *G01J 5/00* (2013.01); *G01J 5/0025* (2013.01);

(Continued)

(58) Field of Classification Search
CPC ... G06T 7/0012; A61B 5/0075; A61B 5/0077; A61B 5/01; A61B 5/015; A61B 5/441; A61B 5/445; A61B 5/7425
See application file for complete search history.

(56) References Cited

U.S. PATENT DOCUMENTS

| | | |
|---|---|---|
| 5,803,082 A | 9/1998 | Stapleton et al. |
| 6,757,412 B1 | 6/2004 | Parsons et al. |

(Continued)

FOREIGN PATENT DOCUMENTS

| | | |
|---|---|---|
| WO | WO2009154765 A1 | 12/2009 |
| WO | WO2016064795 A1 | 4/2016 |

OTHER PUBLICATIONS

M. Bharara, J. Schoess, Wound Inflammatory Index: A "Proof of Concept" Study to Assess Wound Healing Trajectory, J. Diabetes Science and Tech., Jul. 4, 2010, V. 4, 774-776, 778 (Year 2010).

(Continued)

*Primary Examiner* — Amal Aly Farag
(74) *Attorney, Agent, or Firm* — Maginot, Moore & Beck, LLP

(57) ABSTRACT

A system for determining a clinically relevant temperature differential between a predetermined area of clinical interest on the body surface of a mammal and a control area on the body surface of the mammal. The system includes an image capturing device having a housing, and a visual image capturing device and a thermal image capturing device disposed within the housing. The system also includes a display apparatus on which a captured visual image including the area of clinical interest and a captured thermal image are displayed, and a computing apparatus operatively connected to the image capturing device and to the display apparatus. The computing apparatus includes means for determining a temperature differential between the area of clinical interest and a selected control area on the body surface of the mammal, and means for overlaying the visual image onto the thermal image in a desired orientation on the display apparatus.

7 Claims, 68 Drawing Sheets

Related U.S. Application Data application No. 14/876,485, filed on Oct. 6, 2015, now abandoned, and a continuation-in-part of application No. 14/577,571, filed on Dec. 19, 2014, now abandoned, which is a continuation-in-part of application No. 13/439,177, filed on Apr. 4, 2012, now Pat. No. 9,357,963.

(60) Provisional application No. 62/060,307, filed on Oct. 6, 2014, provisional application No. 61/516,459, filed on Apr. 4, 2011.

(51) Int. Cl.

| | |
|---|---|
| *G01J 5/00* | (2022.01) |
| *G01J 5/07* | (2022.01) |
| *G06T 7/62* | (2017.01) |
| *G01J 5/04* | (2006.01) |

(52) U.S. Cl.
CPC ......... *G01J 5/07* (2022.01); *G01J 2005/0077* (2013.01); *G01J 5/04* (2013.01)

(56) References Cited

U.S. PATENT DOCUMENTS

| | | | |
|---|---|---|---|
| 6,775,397 | B1 | 8/2004 | Hamalainen |
| 6,920,236 | B2 * | 7/2005 | Prokoski ................ G06V 40/16 |
| | | | 356/71 |
| 7,365,330 | B1 | 4/2008 | Sun |
| 7,436,988 | B2 | 10/2008 | Zhang et al. |
| 7,605,924 | B2 | 10/2009 | Howard et al. |
| 7,660,444 | B2 | 2/2010 | Hamalainen |
| 7,995,191 | B1 | 8/2011 | Sandusky |
| 8,090,160 | B2 | 1/2012 | Kakadiaris et al. |
| 8,374,422 | B2 | 2/2013 | Roussel |
| 8,463,006 | B2 | 6/2013 | Prokoski |
| 8,485,668 | B2 | 7/2013 | Zhang et al. |
| 8,494,227 | B2 | 7/2013 | Prokoski |
| 8,659,698 | B2 | 2/2014 | Blayvas et al. |
| 8,836,756 | B2 | 9/2014 | Park et al. |
| 9,087,233 | B2 | 7/2015 | Heringslack |
| 9,103,666 | B2 | 8/2015 | Blayvas |
| 9,117,105 | B2 | 8/2015 | Da et al. |
| 9,229,957 | B2 | 1/2016 | Kwan |
| 9,438,775 | B2 | 9/2016 | Powers et al. |
| 2003/0167008 | A1 * | 9/2003 | Rogers ................... A61B 5/445 |
| | | | 600/474 |
| 2004/0019269 | A1 | 1/2004 | Schaefer et al. |
| 2005/0033145 | A1 | 2/2005 | Graham et al. |
| 2005/0058362 | A1 | 3/2005 | Kita |
| 2006/0188140 | A1 | 8/2006 | Gholap et al. |
| 2009/0092302 | A1 | 4/2009 | Kubota et al. |
| 2009/0157327 | A1 | 6/2009 | Nissila |
| 2009/0326383 | A1 | 12/2009 | Barnes et al. |
| 2010/0014746 | A1 * | 1/2010 | Warnke ................... G01N 25/72 |
| | | | 345/157 |
| 2010/0058222 | A1 * | 3/2010 | Bergstrom .............. G06T 19/00 |
| | | | 715/782 |
| 2010/0172567 | A1 * | 7/2010 | Prokoski .............. A61B 5/0064 |
| | | | 348/47 |
| 2010/0260374 | A1 * | 10/2010 | Akashi .................. G06T 7/0004 |
| | | | 382/100 |
| 2011/0001809 | A1 | 1/2011 | McManus et al. |
| 2011/0040191 | A1 | 2/2011 | Kyle et al. |
| 2011/0215930 | A1 | 9/2011 | Lee et al. |
| 2012/0020573 | A1 * | 1/2012 | Kacenjar ................. G06T 7/337 |
| | | | 382/218 |
| 2012/0078113 | A1 | 3/2012 | Whitestone et al. |
| 2012/0148124 | A1 * | 6/2012 | Chia-Yen ............... A61B 5/015 |
| | | | 382/128 |
| 2013/0162796 | A1 * | 6/2013 | Bharara ................ G06T 7/0016 |
| | | | 348/77 |
| 2014/0046192 | A1 | 2/2014 | Mullin et al. |

OTHER PUBLICATIONS

G. Nakagami, Predicting Delayed Pressure Ulcer Healing Using Thermography: A Prospective Cohort Study, J. Wound Care, Sep. 29, 2013, V. 19 (Year 2013).

C.J.R. Siah, C. Childs, Thermographic Mapping of the Abdomen in Healthy Subjects and Patients After Enterostoma, J. Wound Care, Mar. 2015, pp. 112, 114-120, vol. 24 No. 3, Mark Allen Publishing Ltd., London UK.

\* cited by examiner

Image Capture Device Left Side: *Closed*                    Image Capture Device Left Side: *Open*

Image Capture Device Top Side: *Closed*                    Image Capture Device Top Side: *Open*

Image Capture Device Front Side: *Closed*          Image Capture Device Front Side: *Open*

Image Capture Device Right Side: *Closed*          Image Capture Device Right Side: *Open*

Fig. 1F
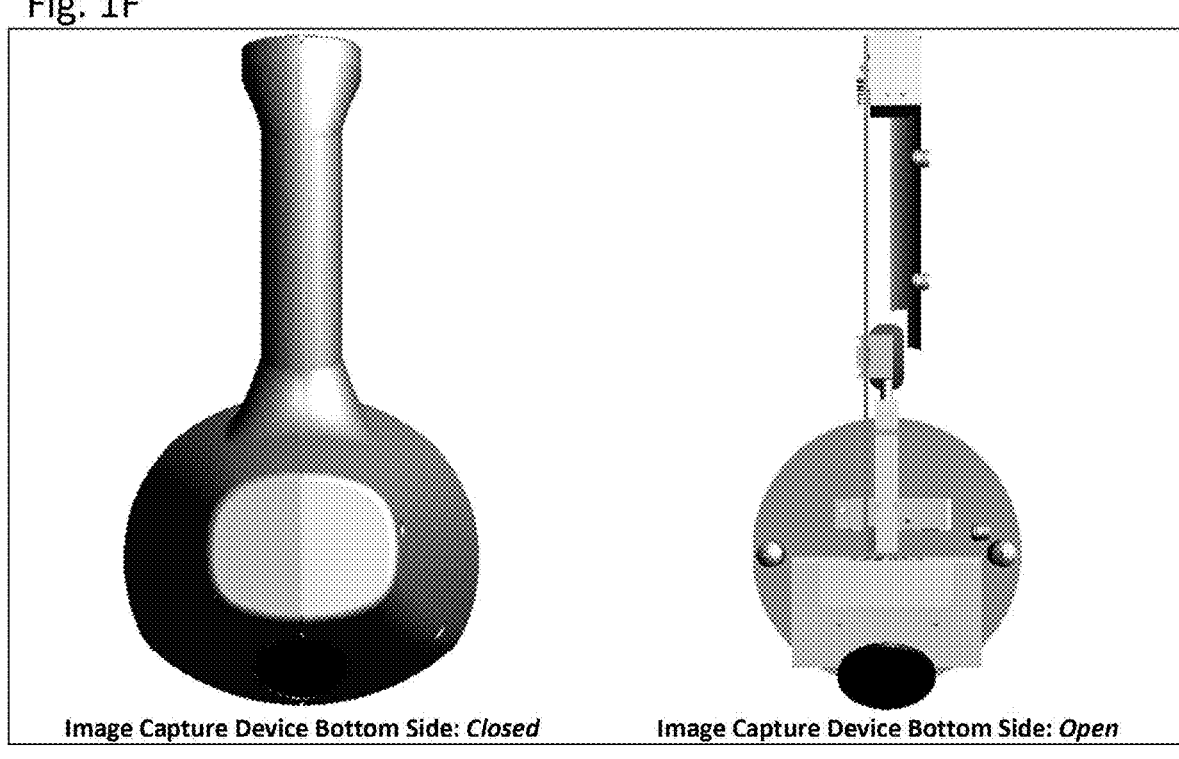
Image Capture Device Bottom Side: *Closed*          Image Capture Device Bottom Side: *Open*
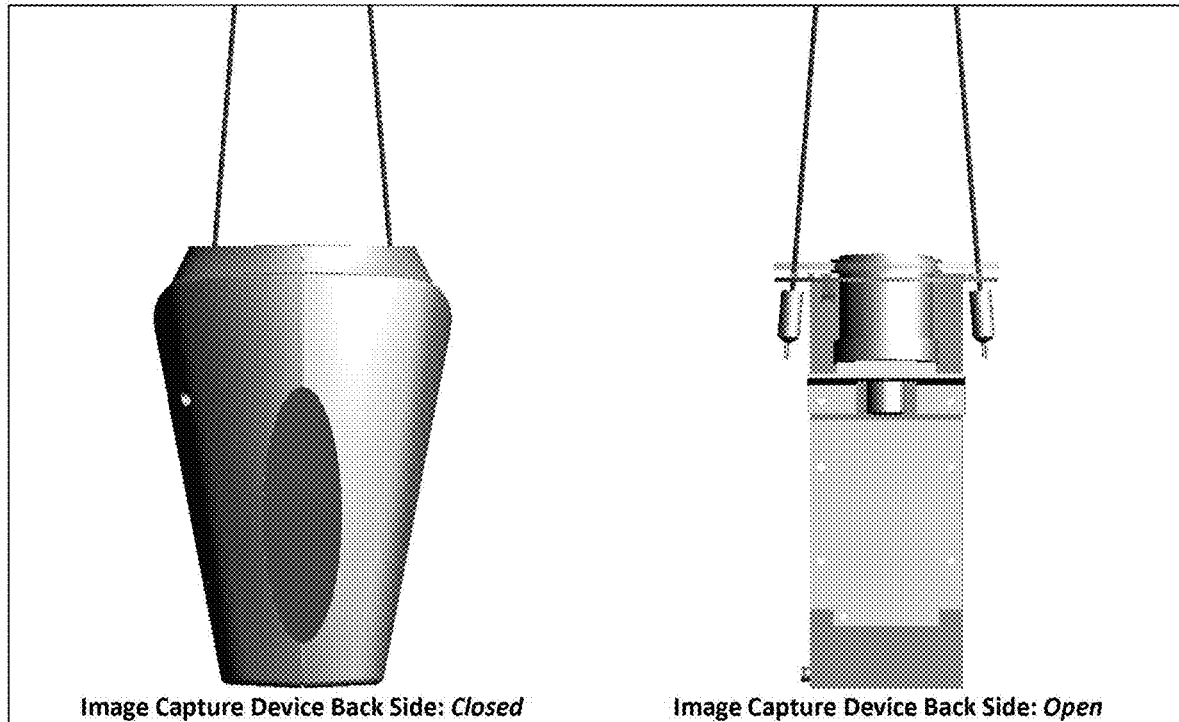
Image Capture Device Back Side: *Closed*          Image Capture Device Back Side: *Open*
Fig. 1G FIG. 1H
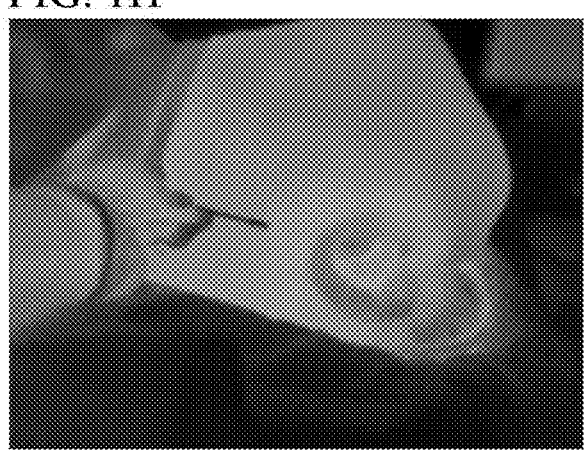

Cooler                                                                Warmer

Cooler                                              Warmer

FIG. 7
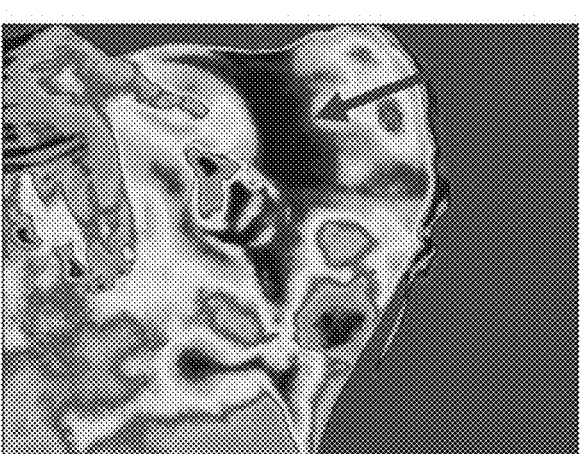

$$Cos(\Theta) = \frac{P}{D}$$

$$Cos(\Theta) = \frac{(x2 - x1)}{D}$$

$$D * Cos(\Theta) = (x2 - x1)$$

$$x2 = x1 + D * Cos(\Theta)$$

similarlarly $$Sin(\Theta) = \frac{Q}{D}$$

$$Sin(\Theta) = \frac{(y1 - y2)}{D} \text{ (for an image (0,0) starts at the top left corner)}$$

$$D * Sin(\Theta) = (y1 - y2)$$

$$y2 = y1 - D * Sin(\Theta)$$

(x2, y2) represents the coordinates of the new automated reference area selection Cooler                                                    Warmer Cooler                                        Warmer Cooler                                                    Warmer Blended Relative Color Relative Color Scale (1 °C increments)

Relative Color Scale (0.75 °C increments)

Relative Color Scale (0.5 °C increments)

Cooler                                    Warmer

Cooler                                                        Warmer

Cooler                                      Warmer

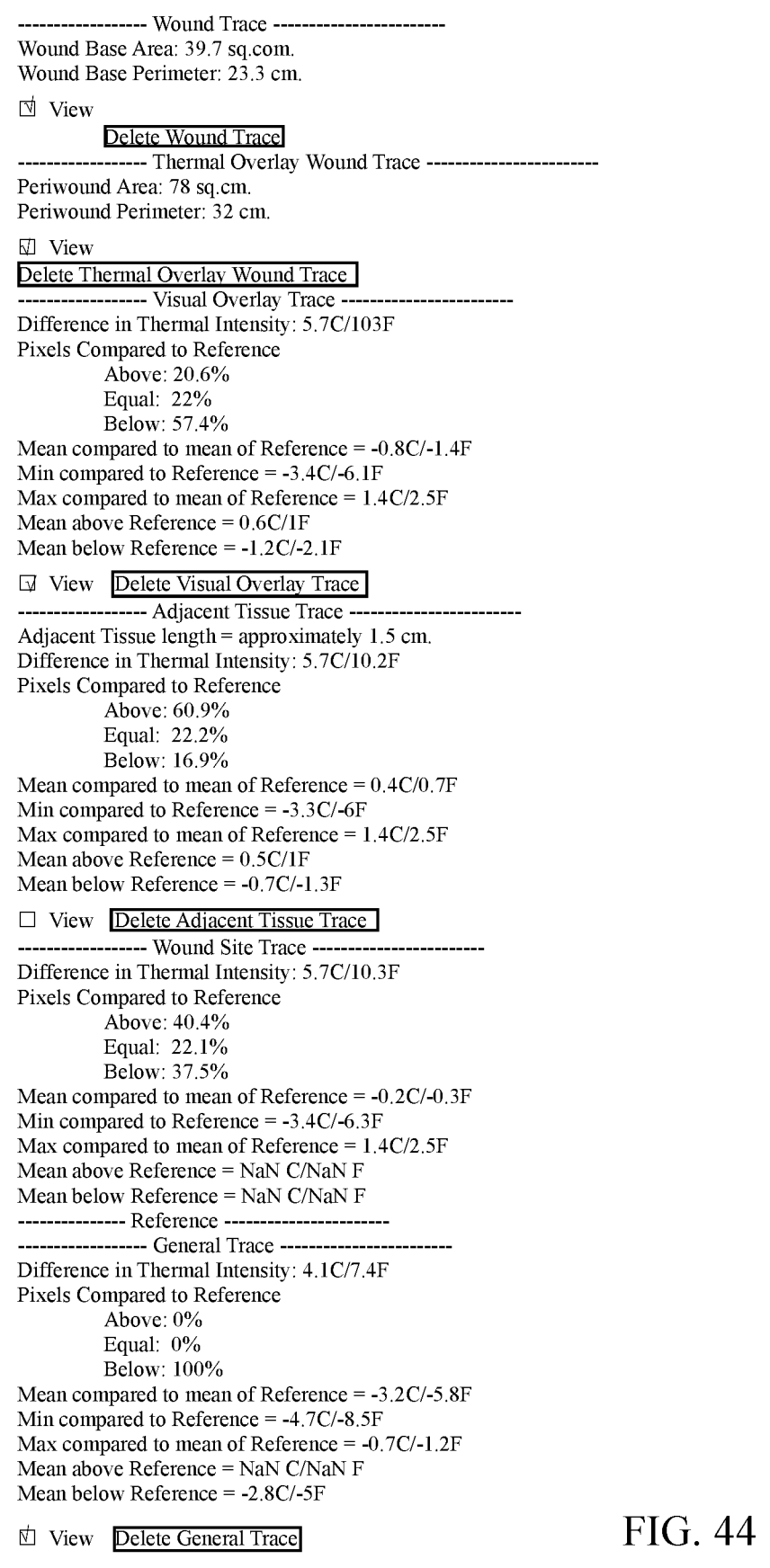

------------------ Wound Trace -----------------------
Wound Base Area: 39.7 sq.com.
Wound Base Perimeter: 23.3 cm.

☑ View
    Delete Wound Trace
------------------ Thermal Overlay Wound Trace -----------------------
Periwound Area: 78 sq.cm.
Periwound Perimeter: 32 cm.

☑ View
Delete Thermal Overlay Wound Trace
------------------ Visual Overlay Trace -----------------------
Difference in Thermal Intensity: 5.7C/103F
Pixels Compared to Reference
          Above: 20.6%
          Equal:  22%
          Below: 57.4%
Mean compared to mean of Reference = -0.8C/-1.4F
Min compared to Reference = -3.4C/-6.1F
Max compared to mean of Reference = 1.4C/2.5F
Mean above Reference = 0.6C/1F
Mean below Reference = -1.2C/-2.1F ☑ View    Delete Visual Overlay Trace
------------------ Adjacent Tissue Trace -----------------------
Adjacent Tissue length = approximately 1.5 cm.
Difference in Thermal Intensity: 5.7C/10.2F
Pixels Compared to Reference
          Above: 60.9%
          Equal:  22.2%
          Below: 16.9%
Mean compared to mean of Reference = 0.4C/0.7F
Min compared to Reference = -3.3C/-6F
Max compared to mean of Reference = 1.4C/2.5F
Mean above Reference = 0.5C/1F
Mean below Reference = -0.7C/-1.3F ☐ View    Delete Adjacent Tissue Trace
------------------ Wound Site Trace -----------------------
Difference in Thermal Intensity: 5.7C/10.3F
Pixels Compared to Reference
          Above: 40.4%
          Equal:  22.1%
          Below: 37.5%
Mean compared to mean of Reference = -0.2C/-0.3F
Min compared to Reference = -3.4C/-6.3F
Max compared to mean of Reference = 1.4C/2.5F
Mean above Reference = NaN C/NaN F
Mean below Reference = NaN C/NaN F
--------------- Reference -----------------------
------------------ General Trace -----------------------
Difference in Thermal Intensity: 4.1C/7.4F
Pixels Compared to Reference
          Above: 0%
          Equal:  0%
          Below: 100%
Mean compared to mean of Reference = -3.2C/-5.8F
Min compared to Reference = -4.7C/-8.5F
Max compared to mean of Reference = -0.7C/-1.2F
Mean above Reference = NaN C/NaN F
Mean below Reference = -2.8C/-5F ☑ View    Delete General Trace

FIG. 44

FIG. 55A
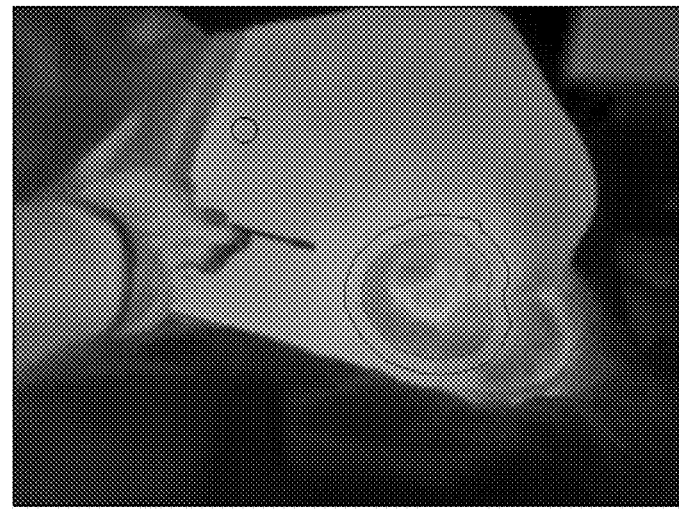
Non-relative grayscale thermal image
FIG. 55B
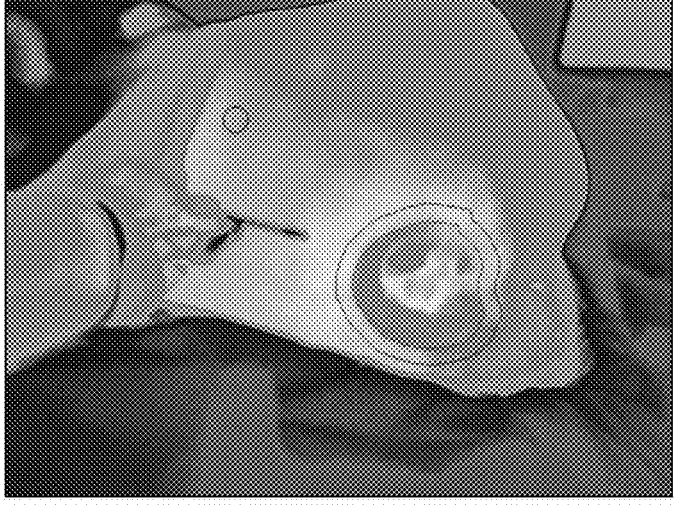
Non-relative iron color scale thermal image
FIG. 55C
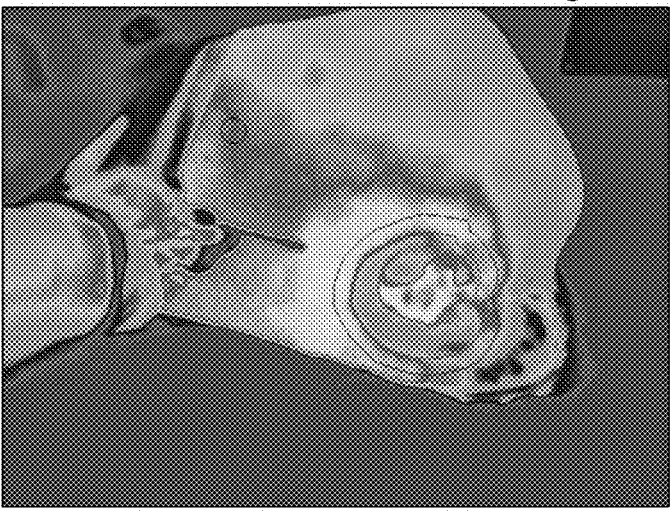
Relative color scale thermal image

METHOD OF MONITORING THE STATUS OF A WOUND

CROSS REFERENCE TO RELATED APPLICATIONS

The present application is a continuation of non-provisional U.S. patent application Ser. No. 15/727,729, filed on Oct. 9, 2017, which is a continuation of non-provisional U.S. patent application Ser. No. 14/876,485, filed on Oct. 6, 2015. U.S. patent application Ser. No. 14/876,485 claims priority to provisional U.S. patent application No. 62/060,307, filed on Oct. 6, 2014; is a continuation-in-part of non-provisional U.S. patent application Ser. No. 13/439,177, filed on Apr. 4, 2012 (now U.S. Pat. No. 10,169,860), which claims priority to provisional U.S. patent application No. 61/516,459, filed on Apr. 4, 2011; and is a continuation-in-part of non-provisional U.S. patent application Ser. No. 14/577,571, filed on Dec. 19, 2014, which claims priority to provisional U.S. patent application No. 61/921,717, filed on Dec. 30, 2013, and to non-provisional U.S. patent application Ser. No. 13/439,177.

BACKGROUND

1. Field of the Invention

The present invention relates generally to methods of using non-invasive technologies in medical care. More specifically, the present invention relates to novel thermal imaging methods and the use of the same in the medical field.

2. Description of the Prior Art

Over the last century, clinicians, which term includes herein certified and licensed medical doctors of all specialties, osteopathic doctors of all specialties, podiatrists, dental doctors of all specialties, chiropractors, veterinarians of all specialties, nurses, and medical imaging technicians, have become dependent on the use of medical devices that assist them in their delivery of patient-centered care. The common function of these devices is to assist and not replace the clinical judgment of the clinician. This fulfills the dictum that best practice is clinical judgment assisted by scientific data and information.

Entering into the era of computer science and sophisticated electronics, clinicians have the opportunity to be supported by data and information in a statistically significant and timely fashion. These advancements have allowed more extensive and useful collection of meaningful data that can be acquired, analyzed, and applied in conjunction with the knowledge and expertise of the clinician.

Medical long-wave infrared (LIR) thermography has been known to be beneficial in the evaluation of thermal heat intensity and gradiency relating to abnormalities of the skin and underlying tissue (SUT). Although this technology has expanded to other areas of medical evaluation, the scope of this patent application is limited to the skin and underlying tissue abnormalities. These abnormalities include the formation of deep tissue injury (DTI) and subsequent necrosis caused by mechanical stress, infection, auto-immune condition, and vascular flow problems. DTI caused by mechanical stress (pressure, shear and frictional forces) can be separated into three categories. The first category is a high magnitude/short duration mechanical stress represented by traumatic and surgical wound and/or areas of interest. The second category is low magnitude/long duration mechanical stress represented by pressure ulcer development, which is also a factor in the development of ischemic and neuropathic wound and/or areas of interests. The third category is a combination of categories one and two represented by pressure ulcer formation in the bariatric patient.

The pathophysiologic conditions that occur with DTI and subsequent necrosis of the affected tissue are ischemia, cell distortion, impaired lymphatic drainage, impaired interstitial fluid flow, and reperfusion injury: Category one is dominated by cell distortion and even destruction. Category two is dominated by ischemia. Category three is a combination of cell distortion and ischemia.

Hypoxia causes aerobic metabolism to convert to anaerobic metabolism. This occurrence causes lactic acidosis followed by cell destruction, release of enzymes and lytic reactions. The release of these substances causes additional cell injury and destruction, and initiation of the inflammatory response.

It is very important to recognize that ischemic-reperfusion injury is associated with all of the above mechanical stress induced underlying tissue injuries. This condition is caused by a hypoxia induced enzymatic change and the respiratory burst associated with phagocytosis when oxygen returns after an ischemic event. The result of ischemic-reperfusion injury is the formation of oxygen free radicals (hydroxyl, superoxide, and hydrogen peroxide) that cause damage to healthy and already injured cells leading to extension of the original injury Underlying tissue injury and subsequent necrosis can also be caused by vascular disorders. Hypoxia can be caused by an arterial occlusion or by venous hypertension. Lymphatic flow or node obstruction can also create vascular induced injury by creating fibrous restriction to venous drainage and subsequent cellular stasis in the capillary system. These disorders are also accentuated by reperfusion injury and oxygen free radical formation.

Infection of the skin (impetigo), underlying tissue (cellulitis), deep tissue (fasciitis), bone (osteomyelitis) and cartilage (chondritis) causes injury and necrosis of the affected tissue. Cells can be injured or destroyed by the microorganism directly, by toxins released by the microorganism and/or the subsequent immune and inflammatory response. These disorders are also accentuated by reperfusion injury and oxygen free radical formation.

Auto-immune morbidities of the skeletal joints (rheumatoid arthritis), skin and underlying tissue (tendonitis, myelitis, dermatitis) and blood vessels (vasculitis) cause similar dysfunction and necrosis of the tissue being affected by the hypersensitivity reactions on the targeted cells and the subsequent inflammatory response. Again, these conditions are accentuated by reperfusion and oxygen free radical formation.

The common event that addresses all of the above skin and underlying tissue injuries is the inflammatory response. This response has two stages. The first stage is vascular and the second is cellular. The initial vascular response is vasoconstriction that will last a short time. The constriction causes decrease blood flow to the area of injury. The decrease in blood flow causes vascular "pooling" of blood (passive congestion) in the proximal arterial vasculature in the region of injury and intravascular cellular stasis occurs along with coagulation.

The second vascular response is extensive vasodilation of the blood vessels in the area of necrosis. This dilation along with the "pooled" proximal blood causes increased blood flow with high perfusion pressure into the area of injury.

This high pressure flow can cause damage to endothelial cells. Leakage of plasma, protein, and intravascular cells causes more cellular stasis in the capillaries (micro-thrombotic event) and hemorrhage into the area of injury. When the perivascular collagen is injured, intravascular and extravascular coagulation occurs. The rupture of the mast cells causes release of histamine that increases the vascular dilation and the size of the junctions between the endothelial cells. This is the beginning of the cellular phase. More serum and cells (mainly neutrophils) enter into the area of the mixture of injured and destroyed cells by the mechanism of marginalization, emigration (diapedesis) and the chemotaxic recruitment (chemotaxic gradiency). Stalling of the inflammatory stage can cause the area of necrosis (ring of ischemia) to remain in the inflammatory stage long past the anticipated time of 2-4 days. This continuation of the inflammatory stage leads to delayed resolution of the ischemic necrotic event.

The proliferation stage starts before the inflammatory stage recedes. In this stage angiogenesis occurs along with formation of granulation and collagen deposition. Contraction occurs, and peaks, at 5-15 days post injury.

Re-epithelialization occurs by various processes depending on the depth of injury. Partial thickness wound and/or area of interests can resurface within a few days. Full thickness wound and/or area of interests need granulation tissue to form the base for re-epithelialization to occur. The full thickness wound and/or area of interest does not heal by regeneration due to the need for scar tissue to repair the wound and/or area of interest. The repaired scarred wound and/or area of interest has less vascularity and tensile strength of normal regional uninjured skin and underlying tissue. The final stage is remodeling. In this stage the collagen changes from type III to a stronger type I and is rearranged into an organized tissue.

All stages of wound and/or area of interest healing require adequate vascularization to prevent ischemia, deliver nutrients, and remove metabolic waste. Following the vascular flow and metabolic activity of a necrotic area is currently monitored by patient assessment and clinical findings of swelling, pain, redness, increased temperature, and loss of function.

Medical devices are now available to assist the clinician in defining the presence, type, and status of the skin and underlying tissue injury. The LIR thermal and digital imaging device is a non-contact and non-radiating device that can be utilized bedside. The combination of imagers allows both visible and invisible radiation from the body to be evaluated. (See FIG. 1H.) This allows both the anatomical and physiologic status of the skin and underlying tissue to be evaluated for injuries or disorders that are not yet clinically recognizable. By visualizing the IR thermal intensity, the clinician can evaluate the gradiency of the long-wave radiation emitted from the body region being imaged. The ability to visualize the thermal gradiency allows the clinician to evaluate the metabolic activity and blood flow of the region being imaged. The normal underlying tissue can be used as a control for that specific imaging procedure.

Having a real time control allows an area of interest (AOI) to be recognized. The AOI can be of greater intensity (hotter) or less intensity (cooler) than the normal underlying tissue of that region of the body. The AOI can then be evaluated by the clinician for the degree of metabolism, blood flow, necrosis, inflammation and the presence of infection by comparing the warmer or cooler thermal intensity of the AOI or wound and/or area of interest base and peri-AOI or wound and/or area of interest area to the normal underlying tissue of the location being imaged. Serial imaging also can assist the clinician in the ability to recognize improvement or regression of the AOI or wound and/or area of interest over time.

The use of an LIR thermal and digital visual imager can be a useful adjunct tool for clinicians with appropriate training to be able to recognize physiologic and anatomical changes in an AOI before it presents clinically and also the status of the AOL/wound and/or area of interest in a trending format. By combining the knowledge obtained from the images with a comprehensive assessment, skin and underlying tissue evaluation, and an AOI or wound and/or area of interest evaluation will assist the clinician in analyzing the etiology, improvement or deterioration, and the presence of infection affecting the AOI or wound and/or area of interest.

The foundational scientific principles behind LIR thermography technology are energy, heat, temperature, and metabolism.

Energy is not a stand-alone concept. Energy can be passed from one system to another, and can change from one form to another, but can never be lost. This is the First Law of Thermodynamics. Energy is an attribute of matter and electromagnetic radiation. It is observed and/or measured only indirectly through effects on matter that acquires, loses or possesses it and it comes in many forms such as mechanical, chemical, electrical, radiation (light), and thermal.

The present application focuses on thermal and chemical energy. Thermal energy is the sum of all of the microscopic scale randomized kinetic energy within a body, which is mostly kinetic energy, Chemical energy is the energy of electrons in the force field created by two or more nuclei, mostly potential energy.

Energy is transferred by the process of heat. Heat is a process in which thermal energy enters or leaves a body as the result of a temperature difference. Heat is therefore the transfer of energy due to a difference in temperature; heat is a process and only exists when it is flowing. When there is a temperature difference between two objects or two areas within the same object, heat transfer occurs. Heat energy transfers from the warmer areas to the cooler areas until thermal equilibrium is reached. This is the Second Law of Thermodynamics. There are four modes of heat transfer: evaporation, radiation, conduction and convection.

Molecules are the workhorses and are both vehicles for storing and transporting energy and the means of converting it from one form to another. When the formation, breaking, or rearrangement of the chemical bonds within the molecules is accompanied by the uptake or release of energy it is usually in the form of heat. Work is completely convertible to heat and defined as a transfer due to a difference in temperature, however work is the transfer of energy by any process other than heat. In other words, performance of work involves a transformation of energy.

Temperature measures the average randomized motion of molecules (kinetic energy) in a body. Temperature is an intensive property by which thermal energy manifests itself. It is measured by observing its effect on some temperature dependent variable on matter (i.e. ice/steam points of water). Scales are needed to express temperature numerically and are marked off in uniform increments (degrees).

As a body loses or gains heat, its temperature changes in direct proportion to the amount of thermal energy transferred from a high temperature object to a lower temperature object. Skin temperature rises and falls with the temperature of the surroundings. This is the temperature that is referred to in reference to the skins ability to lose heat its surroundings.

The temperature of the deep tissues of the body (core temperatures) remains constant (within ±1° F./±0.6° C.) unless the person develops a febrile illness. No single temperature can be considered normal. Temperature measurements on people who had no illness have shown a range of normal temperatures. The average core temperature is generally considered to be between 98.0° F. and 98.6° F. measured orally or 99.0° F. and 99.6° F. measured rectally. The body can temporarily tolerate a temperature as high as 101° F. to 104° F. (38.6° C. to 40° C.) and as low as 96° F. (35.5° C.) or lower.

Metabolism simply means all of the chemical reactions in all of the cells of the body. Metabolism creates thermal energy. The metabolic rate is expressed in terms to the rate of heat release during the chemical reactions. Essentially all the energy expended by the body is eventually converted into heat.

Since heat flows from hot to cold temperature and the body needs to maintain a core temperature of 37.0° C.±0.75° C., the heat is conserved or dissipated to the surroundings. The core heat is moved to the body surface by blood flow. Decreased flow to the body surface helps conserve heat, while increased flow promotes dissipation. Conduction of the core heat to the body surface is fast, but inadequate alone to maintain the core temperature. Heat dissipation from the body surface (3 mm microclimate) also occurs due to the conduction, convection and evaporation.

Heat production is the principal by-product of metabolism. The rate of heat production is called the metabolic rate of the body. The important factors that affect the metabolic rate are:

Basal Rate of Metabolism (ROM) of all cells of the body.

Extra ROM caused by muscle activity including shivering.

Extra ROM caused by the effect of thyroxine and other hormones to a less extent (i.e.: growth hormone, testosterone).

Extra ROM caused by the effect of epinephrine, norepinephrine, and sympathetic stimulation on the cells.

Extra ROM caused by increased chemical activity in the cells themselves, especially when the cell temperature increases.

Most of the heat produced in the body is generated in the deep organs (liver, brain, heart and the skeletal muscles during exercise). The heat is then transferred to the skin where the heat is lost to the air and other structures. The rate that heat is lost is determined by how fast beat can be conducted from where it is produced in the body core to the skin.

The skin, underlying tissues and especially adipose tissue are the heat insulators for the body. The adipose tissue is important since it conducts heat only 33% as effective as other tissue and specifically 52% as effective as muscle. Conduction rate of heat in human tissue is 18 kcal/cm/m2 k. The skin and underlying tissue insulator system allows the core temperature to be maintained yet allowing the temperature of the skin to approach the temperature of the surroundings.

Blood flows to the skin from the body core in the following manner. Blood vessels penetrate the adipose tissue and enter a vascular network immediately below the skin. This is where the venous plexus comes into play. The venous plexus is especially important because it is supplied by inflow from the skin capillaries and in certain exposed areas of the body (hands-feet-ears) by the highly muscular arterio-venous anastomosis. Blood flow can vary in the venous plexus from barely above zero to 30% of the total cardiac output. There is an approximate eightfold increase in heat conductance between the fully vasoconstricted state and the fully vasodilated state. The skin is an effective controlled heat radiator system and the controlled flow of blood to the skin is the body's most effective mechanism of heat transfer from the core to the surface.

Heat exchange is based on the scientific principle that heat flows from warmer to cooler temperatures. Temperature is thought of as heat intensity of an object. The methods of heat exchange are: radiation (60%), loss of heat in the form of LIR waves (thermal energy), conduction to a solid object (3%), transfer of heat between objects in direct contact and loss of heat by conduction to air (15%) caused by the transfer of heat, caused by the kinetic energy of molecular motion. Much of this motion can be transferred to the air if it is cooler than the surface. This process is self-limited unless the air moves away from the body. If that happens, there is a loss of heat by convection. Convection is caused by air currents. A small amount of convection always occurs due to warmer air rising. The process of convection is enhanced by any process that moves air more rapidly across the body surface (forced convection). This includes fans, air flow beds and air warming blankets.

Convection can also be caused by a loss of heat by evaporation which is a necessary mechanism at very high air temperatures. Heat (thermal energy) can be lost by radiation and conduction to the surroundings as long as the skin is hotter than the surroundings. When the surrounding temperature is higher than the skin temperature, the body gains heat by both radiation and conduction. Under these hot surrounding conditions, the only way the body can release heat is by evaporation. Evaporation occurs when the water molecule absorbs enough heat to change to gas. Due to the fact water molecules absorb a large amount of heat in order to change into a gas, large amounts of body heat can be removed from the body.

Insensible heat loss dissipates the body's heat and is not subject to body temperature control (water loss through the lungs, mouth and skin). This accounts for 10% heat loss produced by the body's basal heat production. Sensible heat loss by evaporation occurs when the body temperature rises and sweating occurs. Sweating increases the amount of water to the skins surface for vaporization. Sensible heat loss can exceed insensible heat loss by 30 times. The sweating is caused by electrical or excess heat stimulation of the anterior hypothalamus pre optic area.

The role of the hypothalamus (anterior pre-optic area) in the regulation of the body's temperatures occurs due to nervous feedback mechanisms that determine when the body temperature is either too hot or too cold.

The role of temperature receptors in the skin and deep body tissues relate to cold and warm sensors in the skin. Cold sensors outnumber warm sensors 10 to 1. The deep tissue receptors occur mainly in the spinal cord, abdominal viscera and both in and around the great veins. The deep receptors mainly detect cold rather than warmth. These receptors function to prevent low body temperature. These receptors contribute to body thermoregulation through the bilateral posterior hypothalamus area. This is where the signals from the pre-optic area and the skin and deep tissue sensors are combined to control the heat producing and heat conserving reactions of the body.

"Temperature Decreasing Mechanisms" include:

Vasodilation of all blood vessels, but with intense dilation of skin blood vessels that can increase the rate of heat transfer to the skin eight-fold.

Sweating can remove 10 times the basal rate of body heat with an additional increase in body temperature.

Decrease in heat production by inhibiting shivering and chemical thermogenesis.

"Temperature Increasing Mechanisms" include:

Skin vasoconstriction throughout the body.

Increase in heat production by increasing metabolic activity, which may include: Shivering (4 to 5 times increase) or Chemical Thermogenesis i.e. burning fat, which may cause adults to have a 10-15% increase in temperature and infants 100% increase in temperature.

LIR thermography evaluates the infra-red thermal intensity. The microbolometer is a 320×240 pixel array sensor that can acquire the long-wave infrared wavelength (7-14 micron) (NOT near-infrared thermography) and convert the thermal intensity into electrical resistance. The resistance is measured and processed into digital values between 1-254. A digital value represents the long-wave infrared thermal intensity for each of the 76,800 pixels. A grayscale tone is then assigned to the 1-254 thermal intensity digital values. This allows a grayscale image to be developed.

Using LIR thermography is a beneficial device to monitor metabolism and blood flow in a non-invasive test that can be performed bedside with minimal patient and ambient surrounding preparation. The ability to accurately measure the LIR thermal intensity of the human body is made possible because of the skin's emissivity (0.98± is 0.01), which is independent of pigmentation, absorptivity (0.98±0.01) reflectivity (0.02) and transmitability (0.000). The human skin mimics the "blackbody" radiation concept. A perfect blackbody only exists in theory and is an object that absorbs and reemits all of its energy. Human skin is nearly a perfect blackbody as it has an emissivity of 0.98, regardless of actual skin color. These same properties allow temperature degrees to be assigned to the pixel digital value. This is accomplished by calibration utilizing a "blackbody" simulator and an algorithm to account for the above factors plus ambient temperatures. A multi-color palate can be developed by clustering pixel values. There are no industry standards how this should be done so many color presentations are being used by various manufacturers. The use of gray tone values is standardized, consistent and reproducible. Black is usually considered cold and white is usually considered hot by the industry.

An LIR camera has the ability to detect and display the LIR wavelength in the electromagnetic spectrum. The basis for infrared imaging technology is that any object whose temperature is above 0° K radiates infrared energy. Even very cold objects radiate some infrared energy. Even though the object might be absorbing thermal energy to warm itself, it will still emit some infrared energy that is detectable by sensors. The amount of radiated energy is a function of the object's temperature and its relative efficiency of thermal radiation, known as emissivity.

Emissivity is a measure of a surface's efficiency in transferring infrared energy. It is the ratio of thermal energy emitted by a surface to the energy emitted by a perfect blackbody at the same temperature.

LIR thermography is a beneficial device to monitor metabolism, and blood flow, and profusion of the skin and underlying tissue in a noninvasive test that can be performed bedside with minimal patient and ambient surrounding preparation. It uses the scientific principles of energy, heat, temperature and metabolism. Through measurement and interpretation of thermal energy, it produces images that will assist clinicians to make a significant impact on wound and/or area of interest care (prevention, early intervention and treatment) through detection.

SUMMARY

Accurate and repeatable measurement of size is essential for documenting progression or regression of the wound and/or area of interest. The long-accepted gold standard of length times width wound and/or area of interest measurement has been shown to have significant errors between when used to compare the results of one observer to another. The first part of the present invention provides a system and method of tracing the wound and/or area of interest edge on a visual image to provide clinicians with both measurements of area and perimeter but the area and perimeter measurement have been shown to be more accurate than length times width with the perimeter measurement being the most accurate. Another aspect of the present invention discloses a system and method for using long wave infrared thermography to analyze physiological aspects such as perfusion and metabolic activity as measured by the effect of a body surface temperature. In another aspect of the present invention there is disclosed a new combination of digital and long wave infrared thermography cameras to simultaneously capture a visual and infrared image of a wound and/or area of interest and surrounding body surface.

Once captured the visual image is used to document the appearance of a wound and/or area of interest, trace the wound and/or area of interest's edge, and determine the area and perimeter of the wound and/or area of interest. The long wave infrared thermographic camera however is used to provide insight into the physiological functions of a wound and/or area of interest and surrounding body surface. The present invention provides means for a trace visual image's wound and/or area of interest to be overlaid onto the congruent thermal wound and/or area of interest shown by the long wave infrared thermographic camera.

The present invention uses long wave infrared thermography as a temperature measurement technique for the visualization and quantification of thermal energy emitted by the human body surface. When using long wave infrared thermography, thermal energy is represented through a unique conversion of gray scale pixel values to temperature values. The gray scale pixel value is a spectrum of absolute white to absolute black where pixel value of one (absolute black) is usually (but not necessarily) the coolest and a pixel value of 254 (absolute white) is usually (but not necessarily) the warmest.

Advantageously the system and methods of the present invention do not provide absolute measurements of temperatures. Instead, the system and method of the present invention allows clinicians to measure and record the temperature of a wound and/or area of interest area of interest and compare that to known unaffected areas on the patient. Thus, the effects of extrinsic and intrinsic variables that affect absolute temperature on a given day and make absolute measurements unreliable for clinical purposes, especially when taken across different days or by different clinicians, are avoided. Some of these intrinsic variables include the normal cycle of thermal production, age, chromatic morbidities, body region, medications, core temperature and others. Extrinsic variables including ambient temperature, humidity, air convection, climate adaption of the tissue, configuration of the body surface, sub straight temperature of the infrared core.

When assessing temperature data from multiple points in time, it is essential that the intrinsic and extrinsic variables described above are minimized. To accomplish this, selection of an unaffected area on a body surface can be used as a control relative to an affected area or likely affected area such as a wound and/or area of interest area of interest. Because the control is exposed to the same intrinsic and extrinsic variables as the affected area, a comparison of the two makes them independent of such variables. Since the temperature data can vary between body regions, it is preferable that the selection of the control area occur on or near the same body surface of the area of interest. If unable to obtain the above, compare to same area on the contralateral side of the body or an available part of the body of the contralateral side is not available. This new reference area should be reproducible for a particular patent.

In combinations with other clinical information clinicians are provided with relative quantitative data and relative qualitative data. Measurements of relative temperature differential can allow clinicians to accurately and reliably evaluate wound and/or area of interest by comparing the same over time through ratio analyses, graphs, and algorithms to unaffected areas thus eliminating the variables that might affect the accuracy of such measurements at a single point in time.

Thus, the present invention comprises, in one exemplary embodiment, a system for determining a clinically relevant temperature differential between a predetermined area of interest on the body surface of a mammal and a control area on the body surface of said mammal, said system comprising: a visual and thermal image capturing device, said image capturing device comprising: a housing, a means for capturing a digital visual image within said housing; and a means for capturing a digital thermal image within said housing; a display apparatus, said display apparatus comprising means for showing said captured visual image and said captured thermal image; and a computing apparatus, said computing apparatus operatively connected to said image capturing device and to said display apparatus, said computing apparatus comprising: a means for selecting a control area on the surface of the skin; a means for determining an temperature of said control area; a means for selecting an area of clinical interest within said visual image; a means for calculating plane geometric features of said selected area of clinical interest; a means for overlaying said digital image onto said thermal image in a desired orientation on said display apparatus; and a means for applying a unique pixel value to a specific predetermined temperature range on said thermal image.

In another exemplary embodiment, the present invention comprises a method of contemporaneously comparing an average temperature of predetermined area of interest on the body surface of a mammal and a control area on the body surface of said mammal, said method comprising the steps of: capturing a physical image of a portion of the body of a mammal capturing a thermal image of said body portion; displaying said physical and said thermal image on a screen; selecting a control area on the surface of the skin; determining an temperature of said control area; selecting an area of clinical interest within said visual image; calculating plane geometric features of said selected area of clinical interest; overlaying said digital image onto said thermal image in a desired orientation on said display apparatus; and applying a unique pixel value to a specific predetermined temperature range on said thermal image.

BRIEF DESCRIPTION OF THE DRAWINGS

The present invention will be understood more fully from the detailed description given hereinafter and from the

Figure 1A:
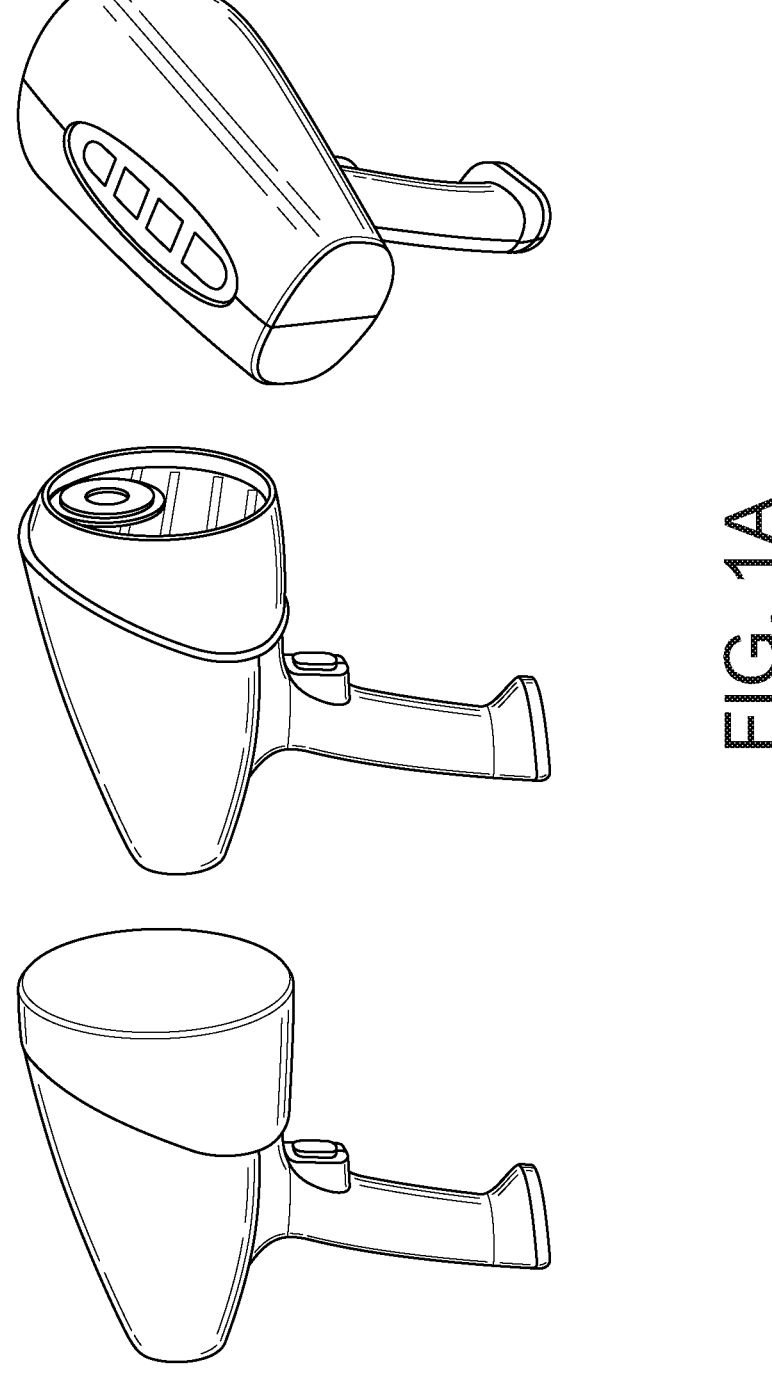

10 accompanying drawings of the preferred embodiment of the present invention, which, however, should not be taken to limit the invention, but are for explanation and understanding only.

In the drawings:

FIG. 1A shows: A visual and thermal image capturing device according to the present invention.

Figure 1B:
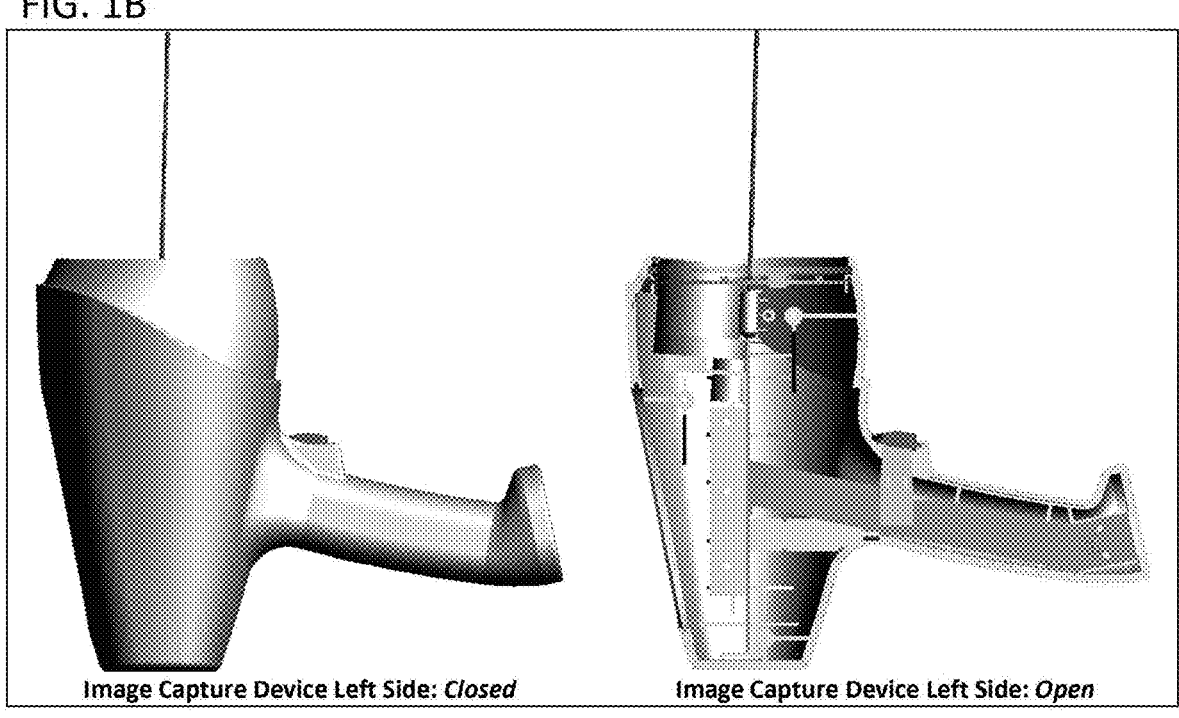

FIG. 1B shows: Left side view of the device open and closed of FIG. 1A.

Figure 1C:
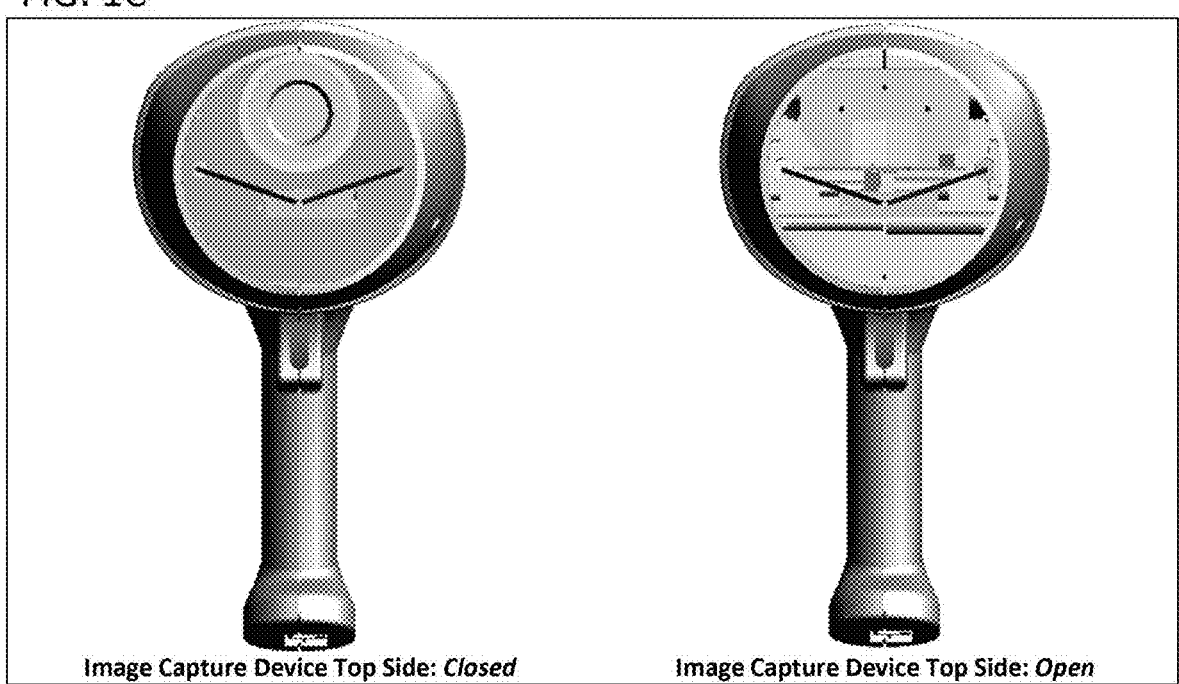

FIG. 1C shows: Top view of the device open and closed of FIG. 1A.

Figure 1D:
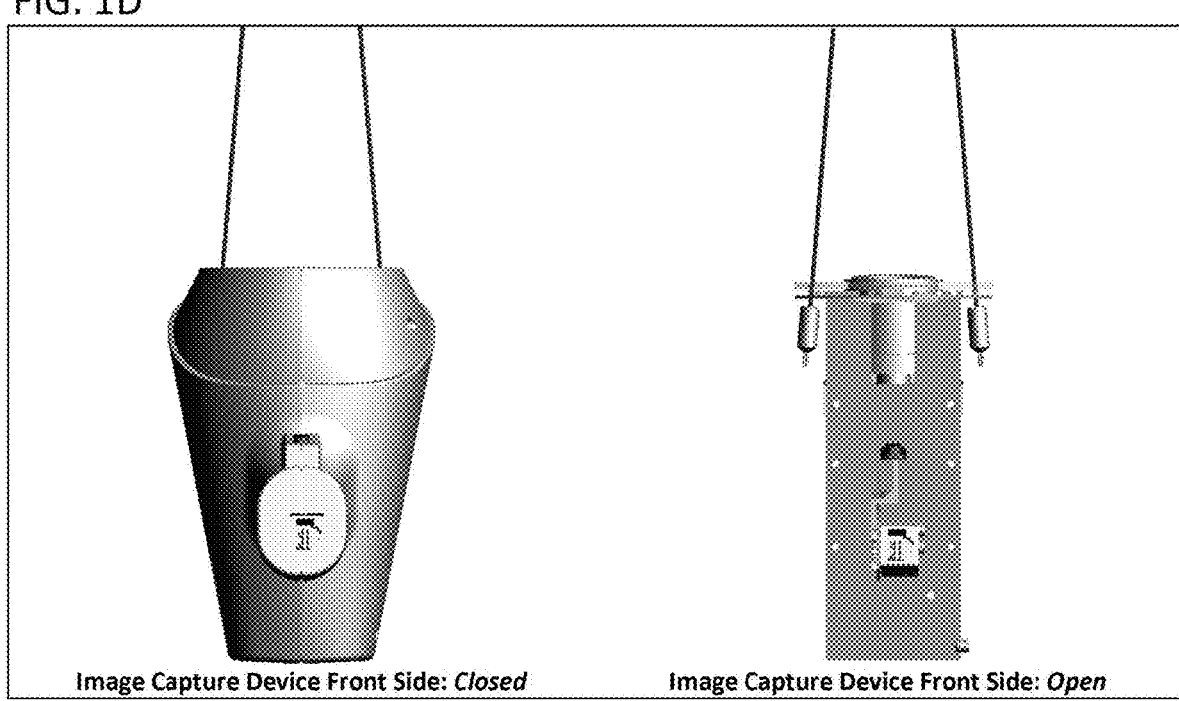

FIG. 1D shows: Front view of the device open and closed of FIG. 1A.

Figure 1E:
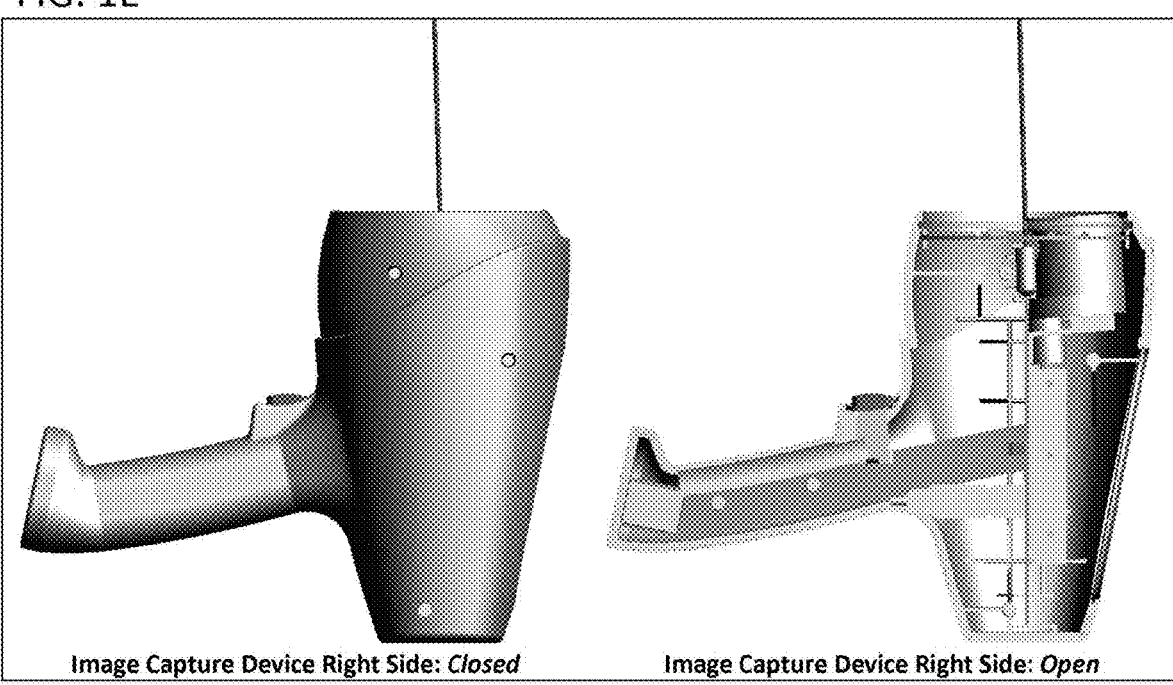

FIG. 1E shows: Right side view of the device open and closed of FIG. 1A.

FIG. 1F shows: Bottom side view of the device open and closed of FIG. 1A.

FIG. 1G shows: Back side view of the device open and closed of FIG. 1A.

FIG. 1H shows: Side-by-side thermal and visual images captured by the device of FIGS. 1A to 1G.

Figure 2:
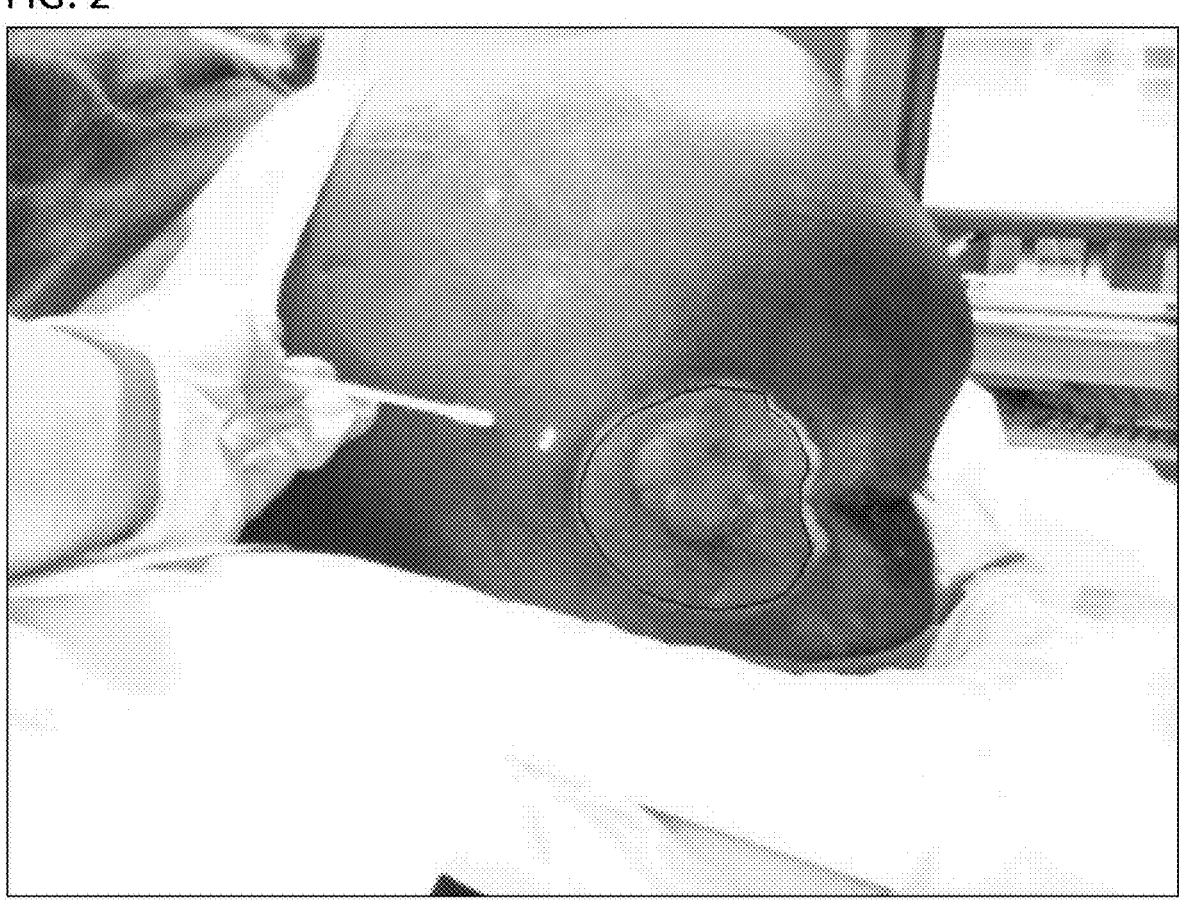

FIG. 2 shows: A computer display of a wound trace on a visual image of the body surface.

Figure 3:
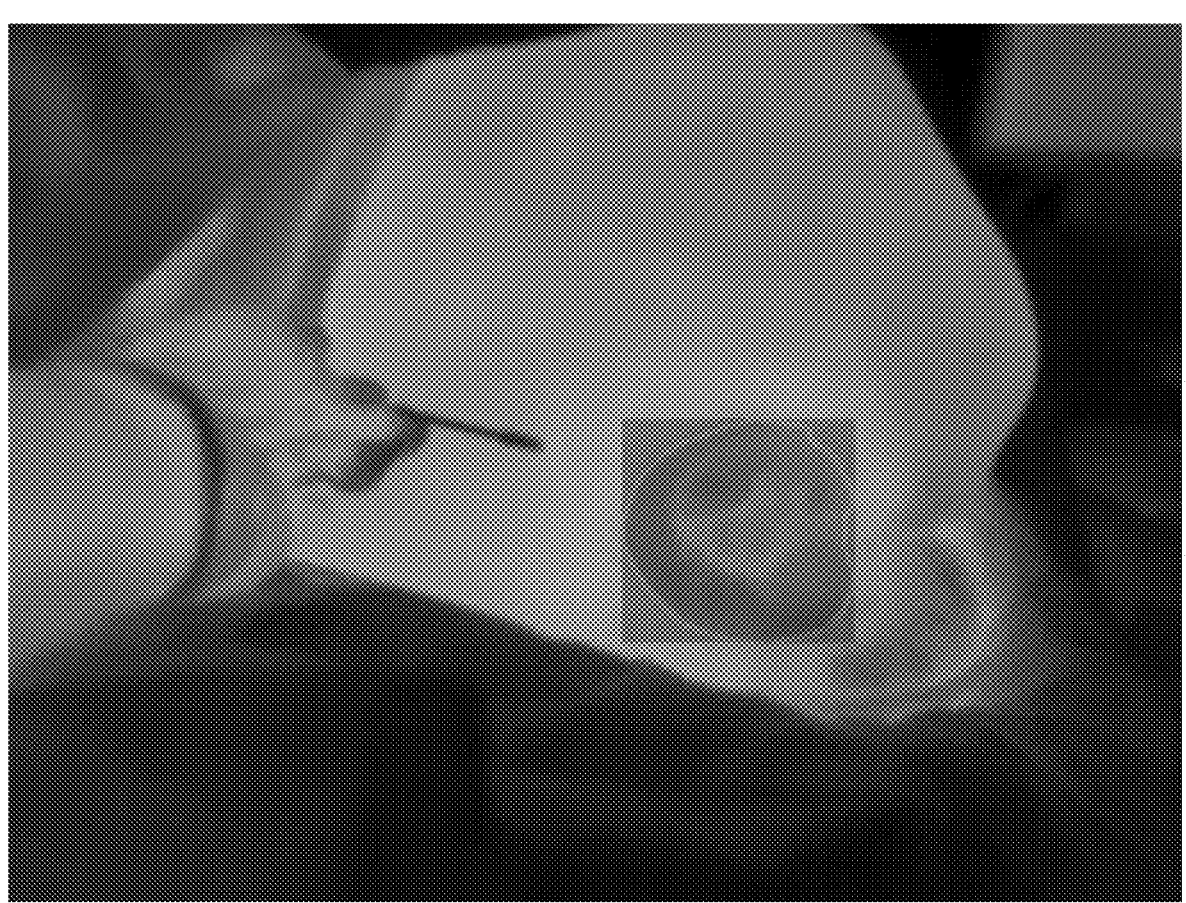

FIG. 3 shows: A computer display of a wound trace overlaid on a thermal image of the body surface.

Figure 4:
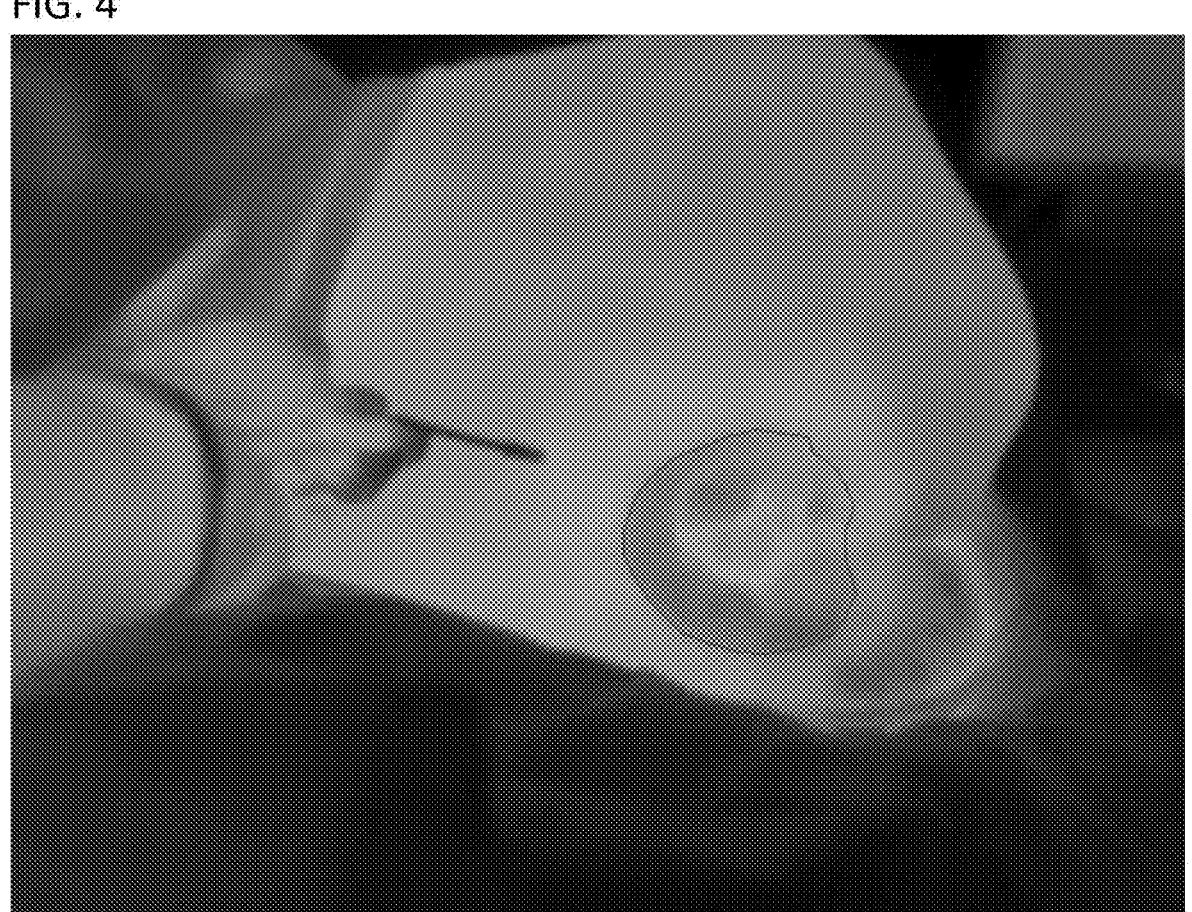

FIG. 4 shows: A computer display of a wound trace placed on a thermal image of the body surface.

Figure 5:
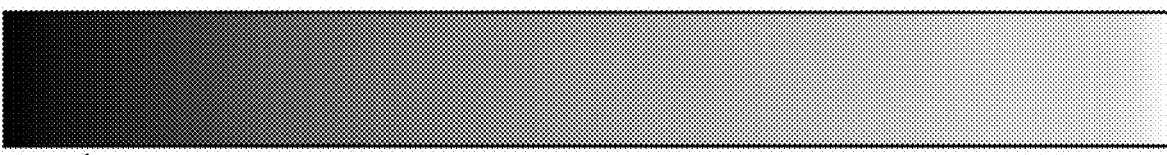

FIG. 5 shows: A non-relative "gray scale" for use with the present invention.

Figure 6:
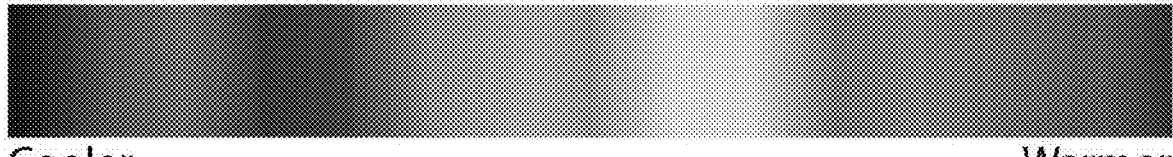

FIG. 6 shows: A non-relative "color scale for use with the present invention.

FIG. 7 shows: An exemplary "hot" thermal image for use with the present invention.

FIG. 8A shows: An exemplary "cold" thermal image for use with the present invention.

Figure 8:
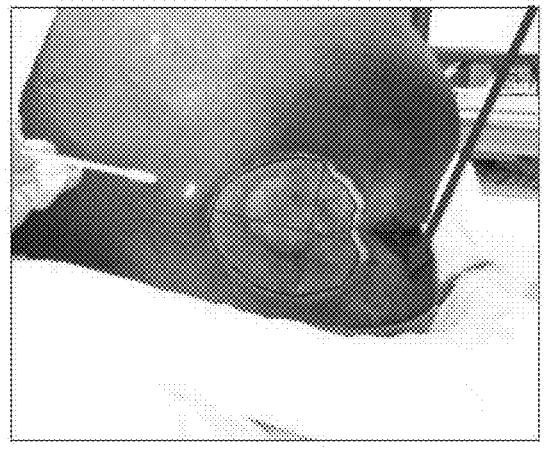
Figure 8B:
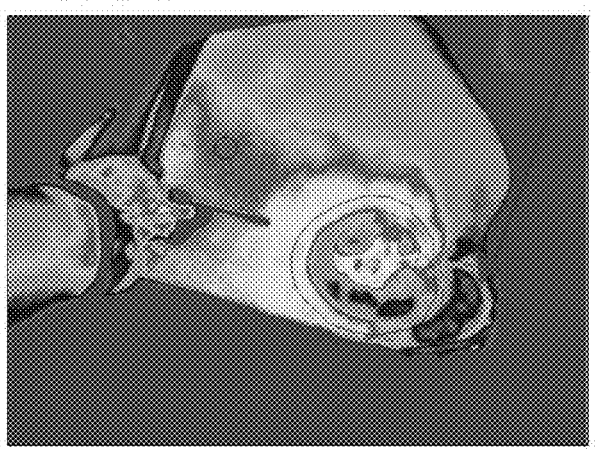

FIG. 8B shows: An exemplary "cold" thermal image for use with the present invention.

Figure 9:
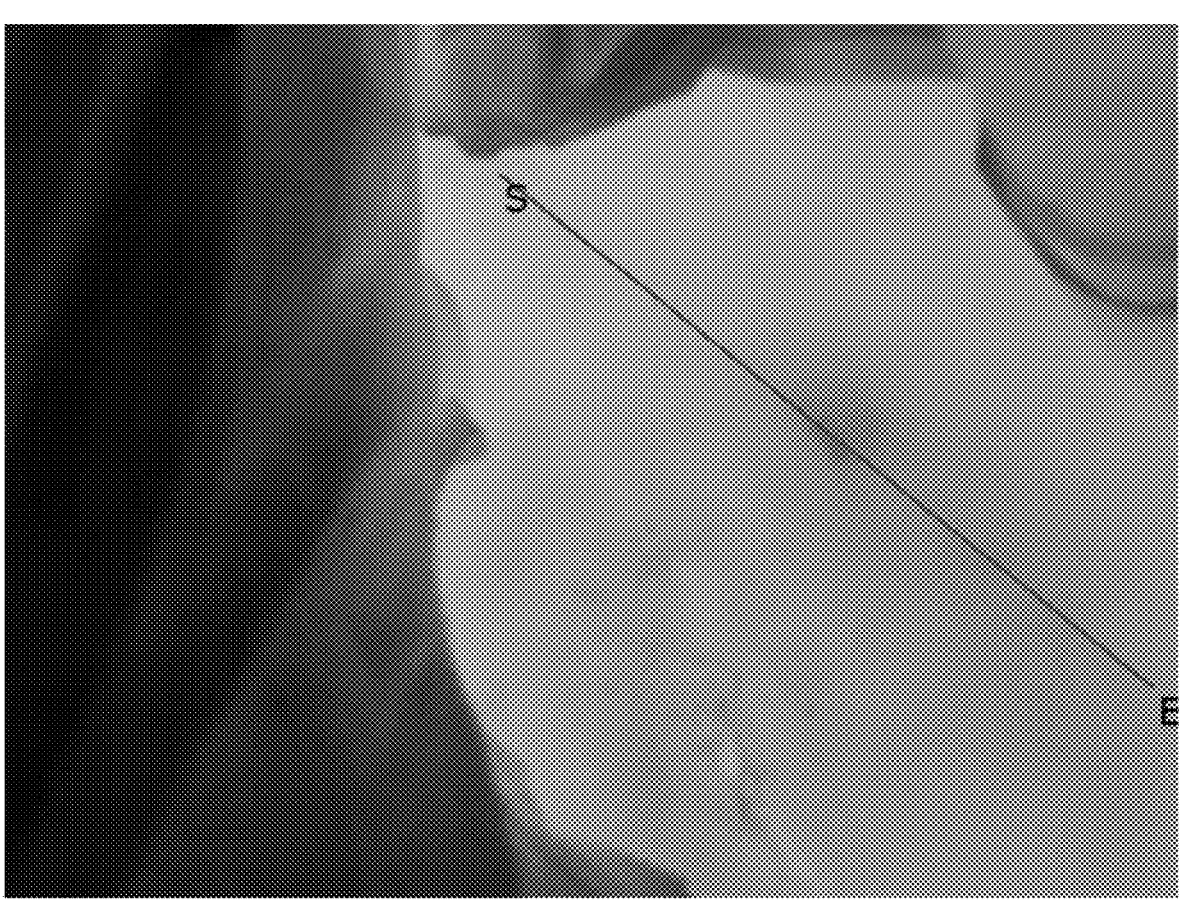

FIG. 9 shows: A "profile" line for use with the present invention.

Figure 10A:
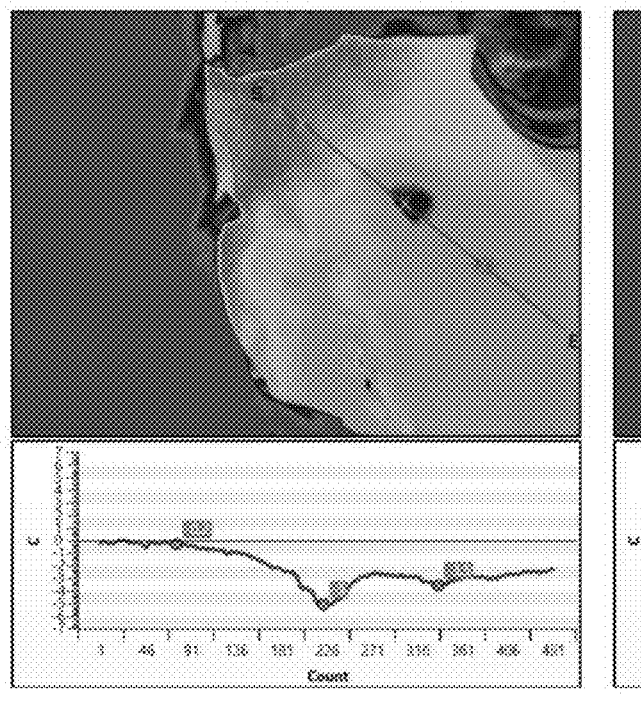
Figure 10B:
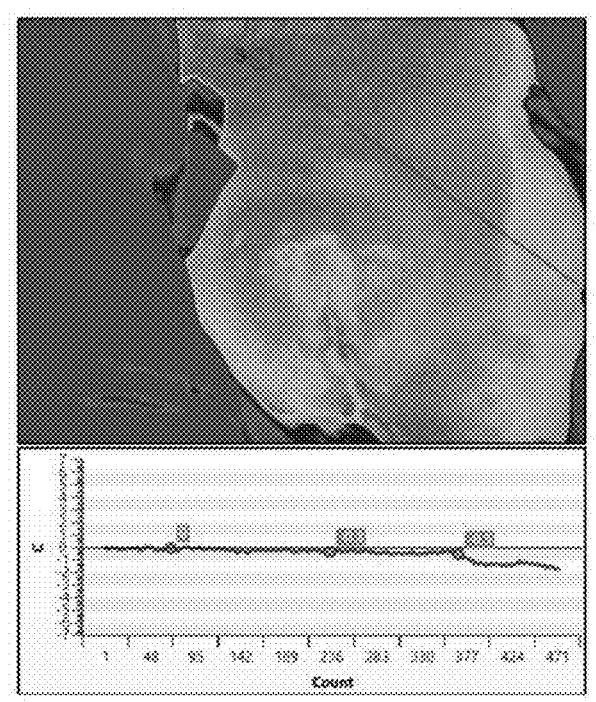

FIG. 10 includes FIGS. 10A and 10B. FIG. 10A shows: A profile line plot showing body surface and underlying tissue anomaly before and after resolution for use with the present invention.

FIG. 10B shows: A profile line plot showing body surface and underlying tissue anomaly before and after resolution for use with the present invention.

Figure 11:
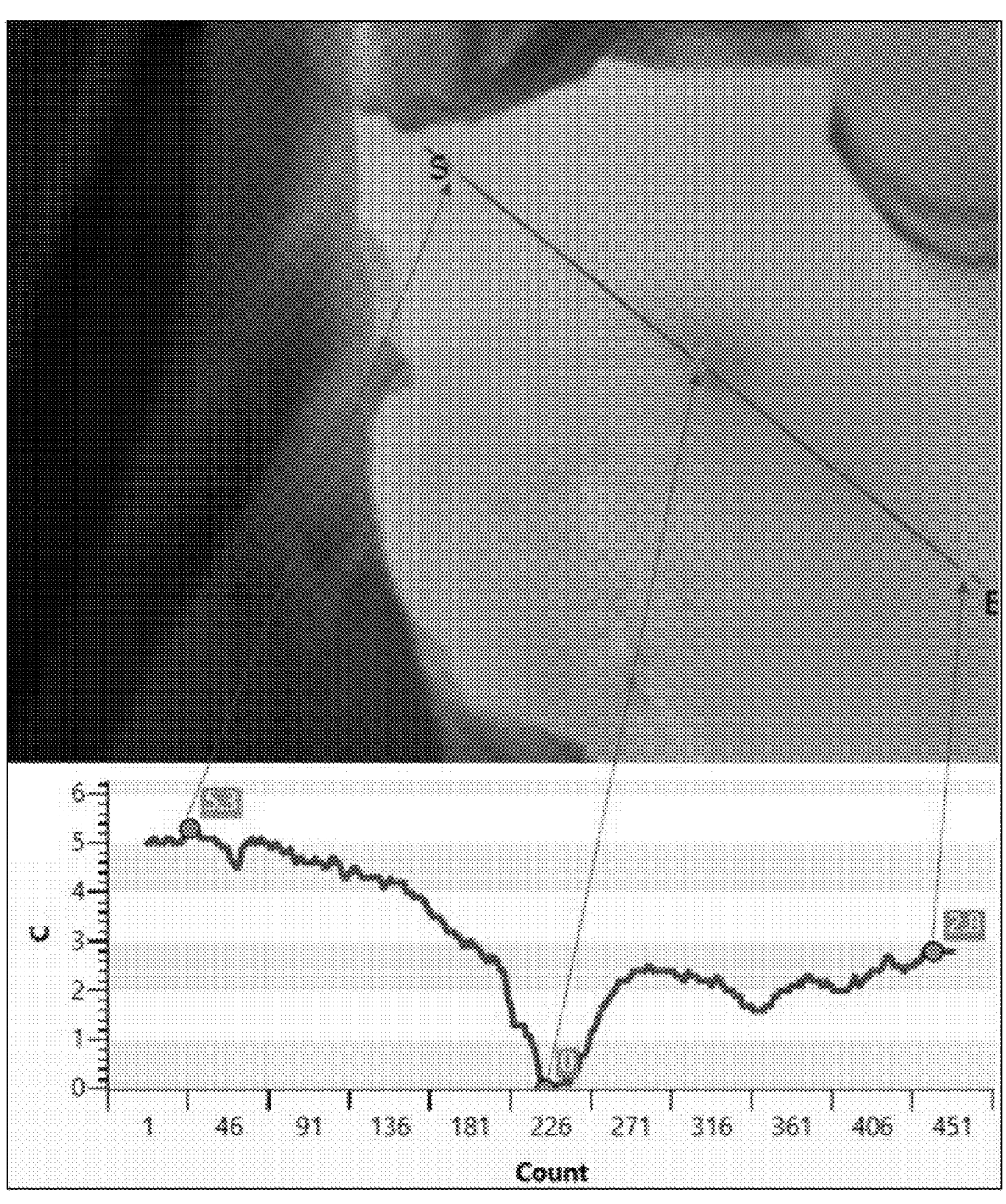

FIG. 11 shows: A larger view of the profile line shown in FIG. 9.

Figure 12:
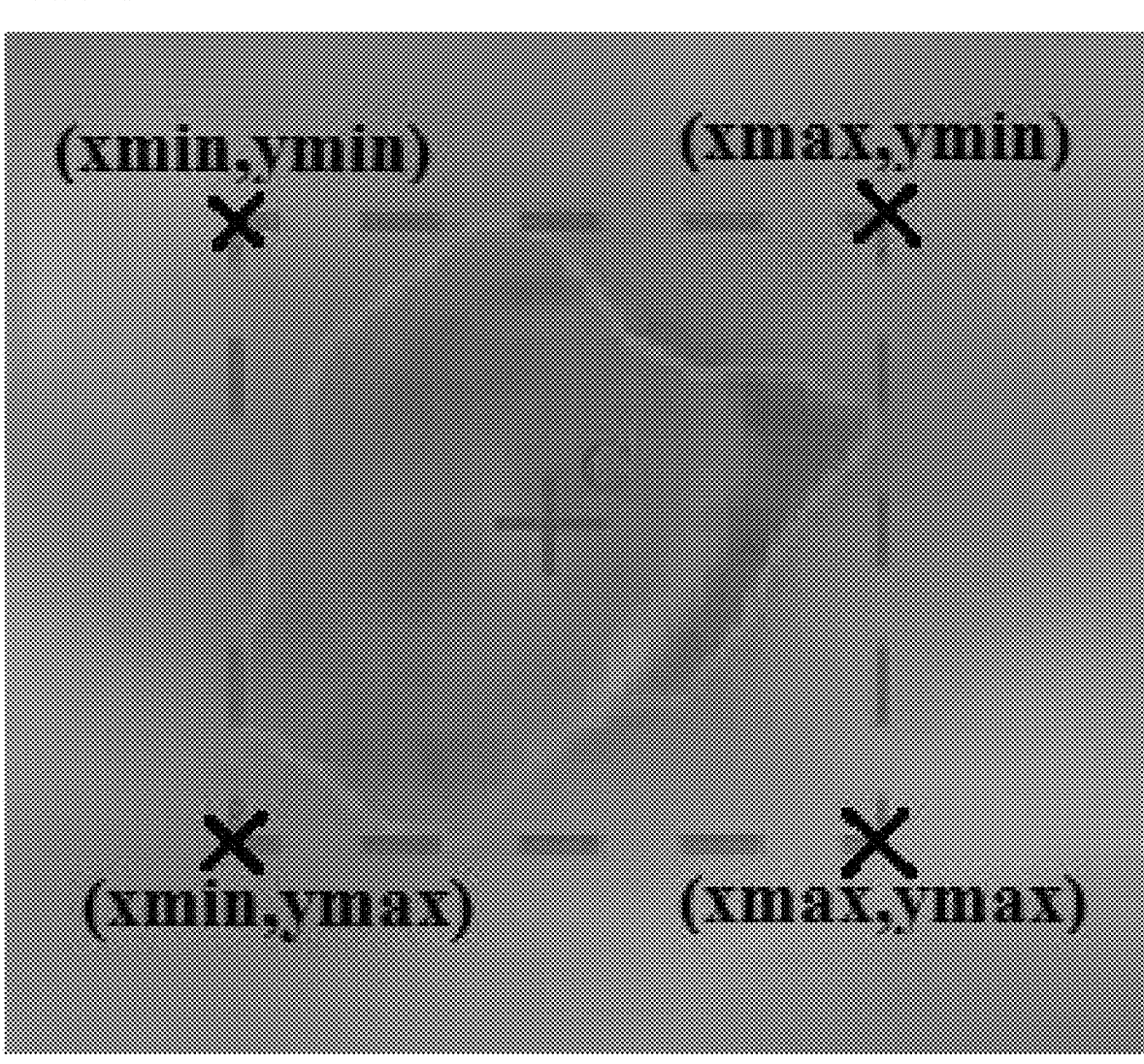

FIG. 12 shows: A graphical representation of the data used to calculate the center point of a traced area.

Figure 13:
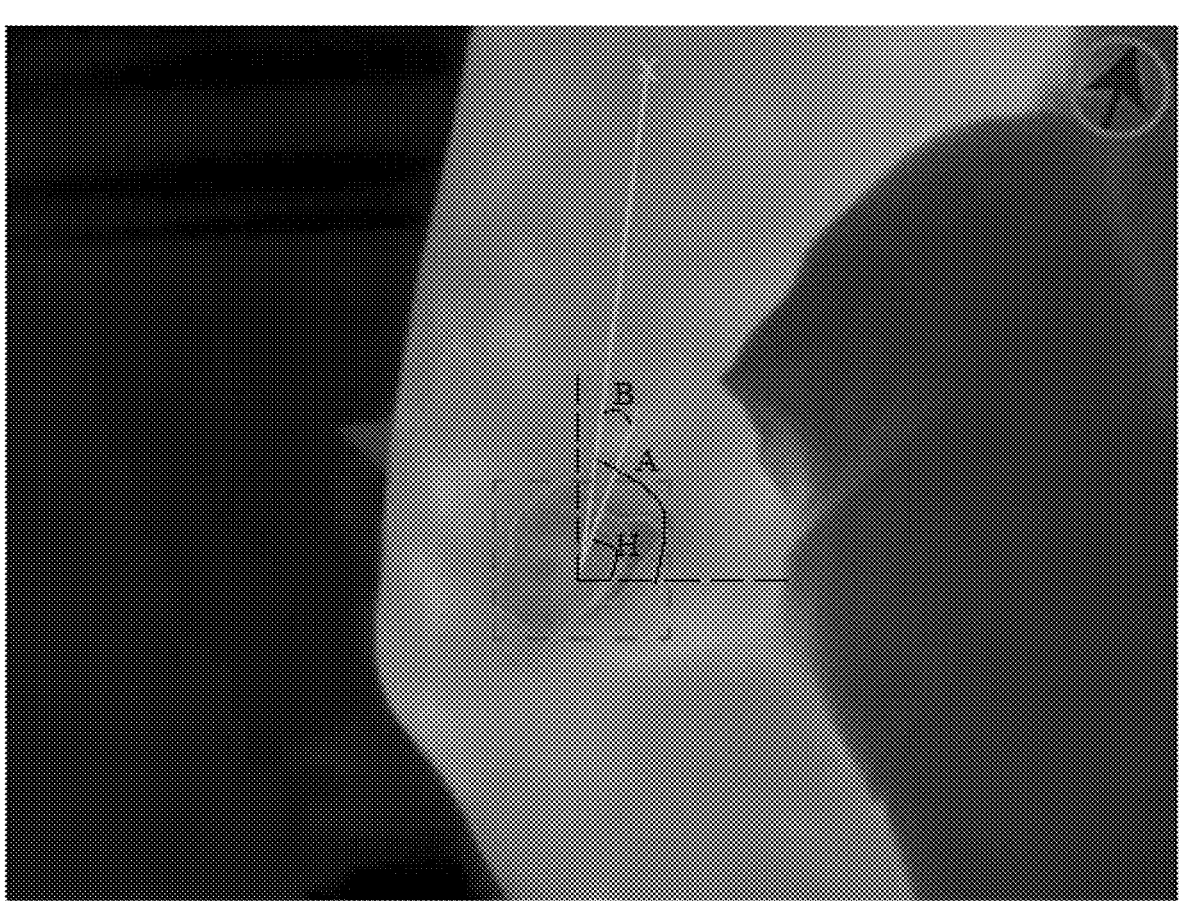

FIG. 13 shows: A graphical representation of orienting an unaffected reference area based on head direction and the center point of the traced area.

Figure 14:
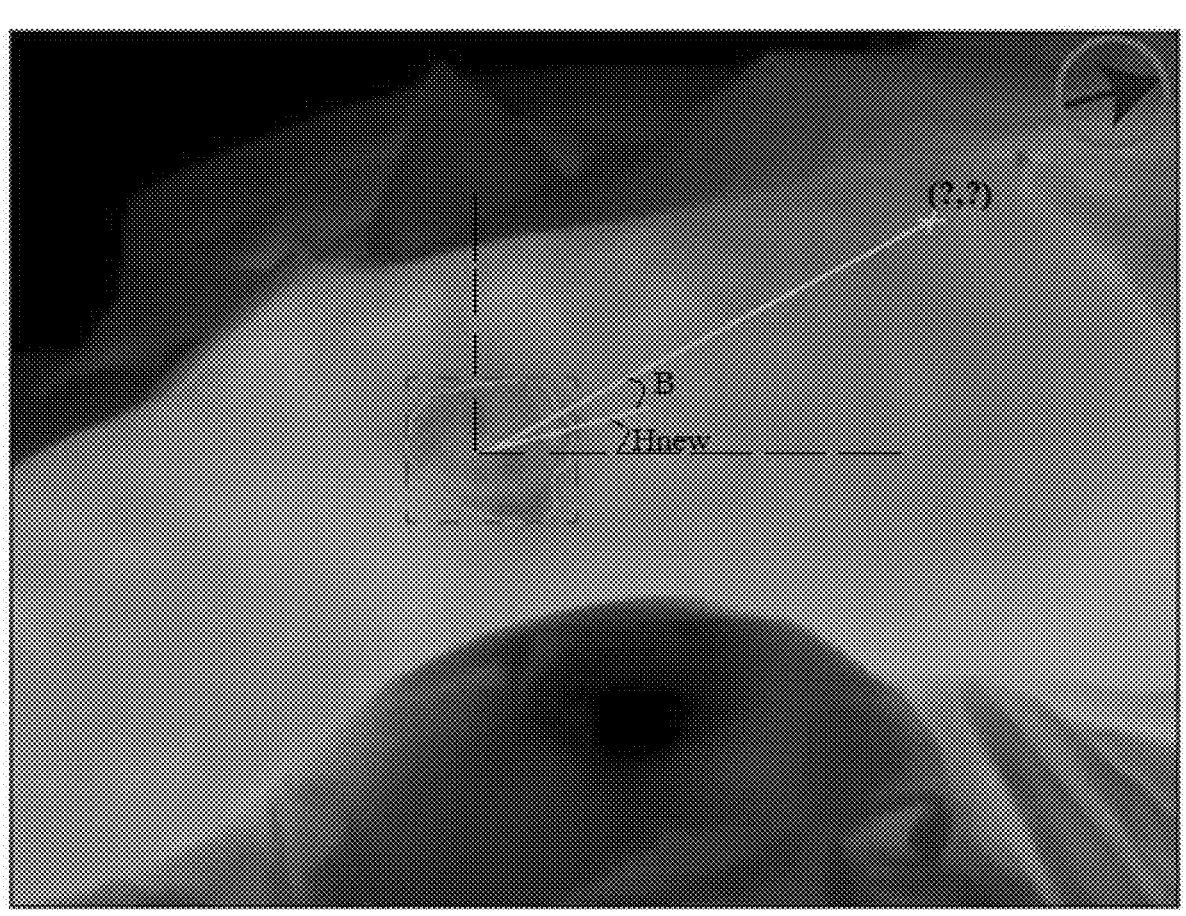

FIG. 14 shows: An alternative representation of orienting an unaffected reference area based on head direction and the center point of the traced area.

Figure 15:
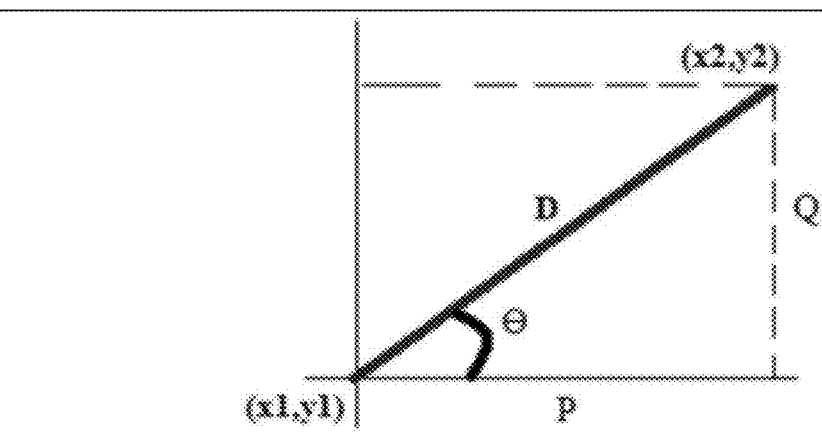

FIG. 15 shows: A graph and calculation for automatically calculating an unaffected reference area.

Figure 16:

FIG. 16 shows: A photograph of a wound trace on a visual image of the body surface.

Figure 17:
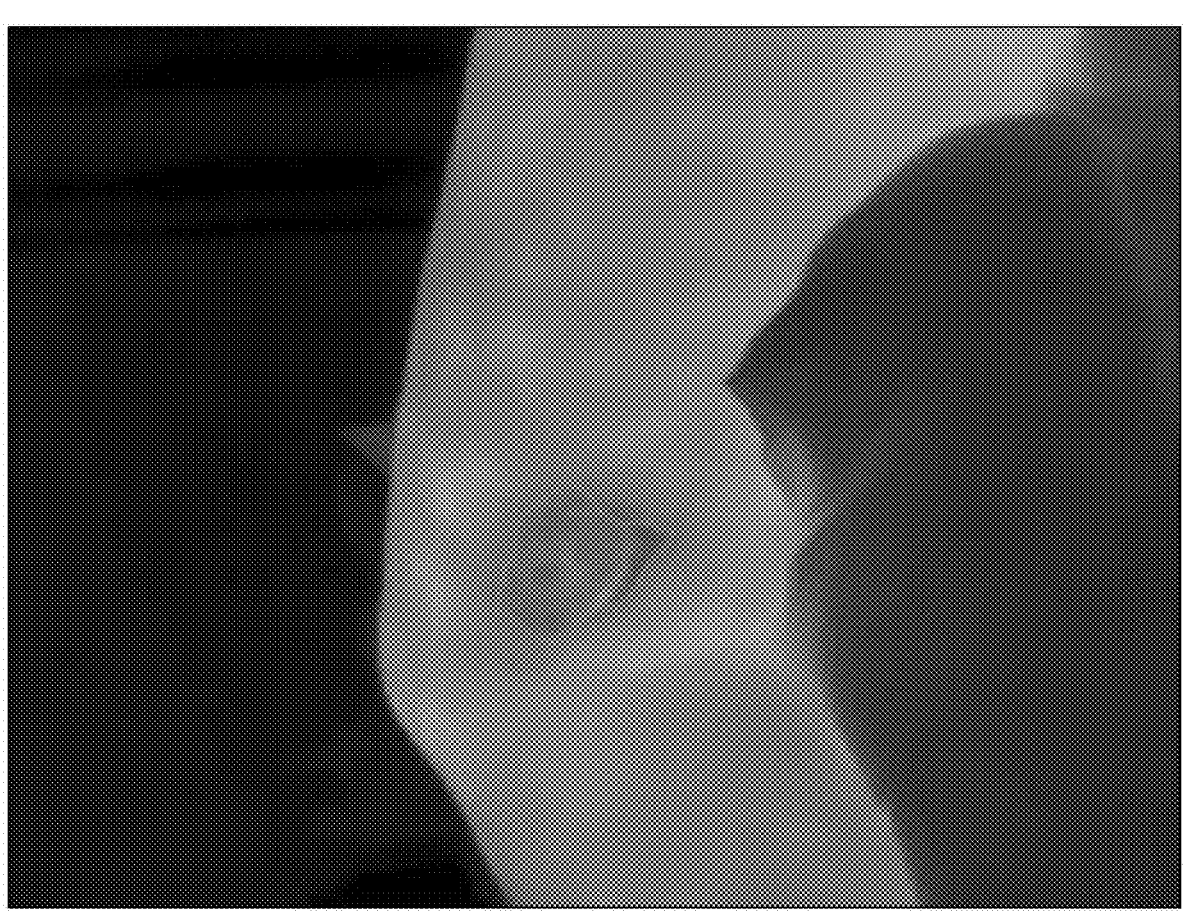

FIG. 17 shows: A photograph of a wound trace placed on a thermal image of the body surface.

Figure 18:
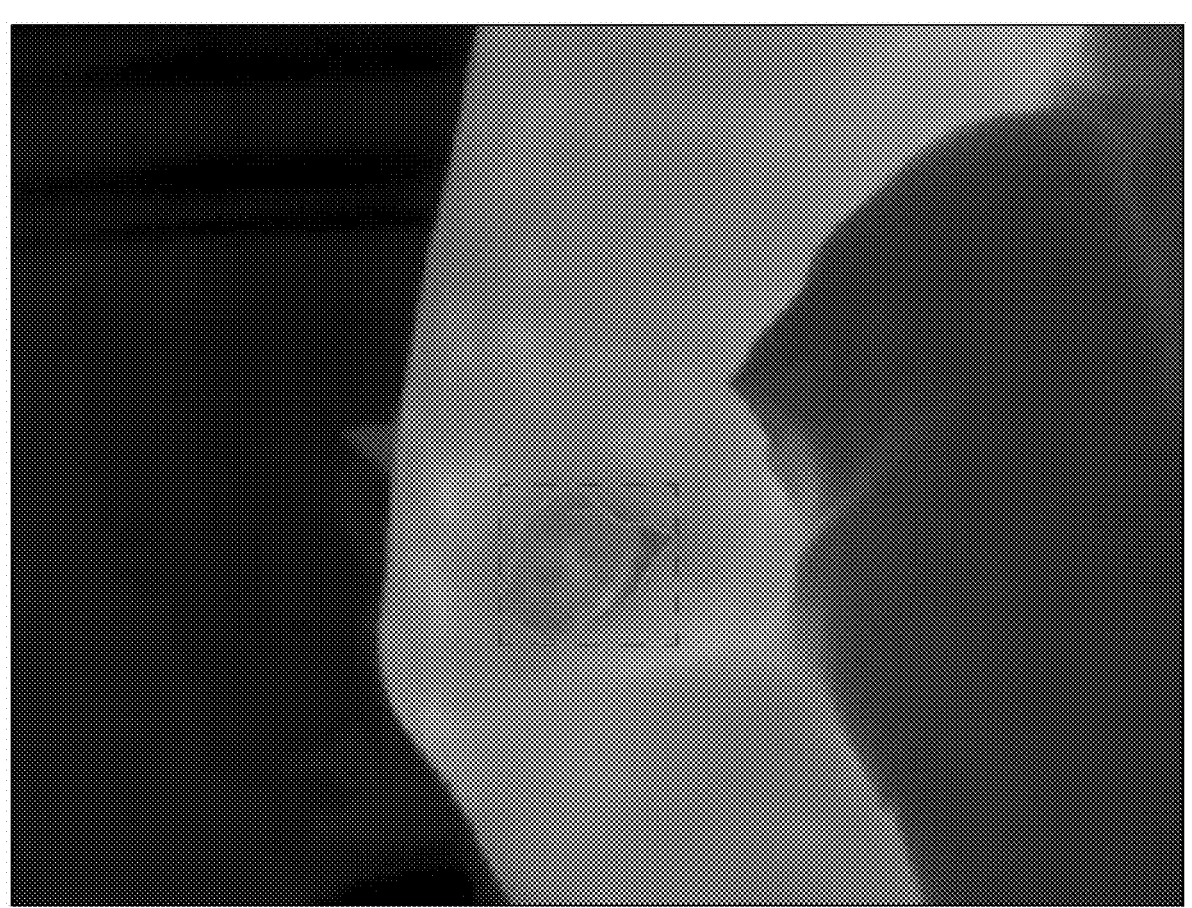

FIG. 18 shows: A photograph of a graphical method of calculating the center point of a traced area.

Figure 19:
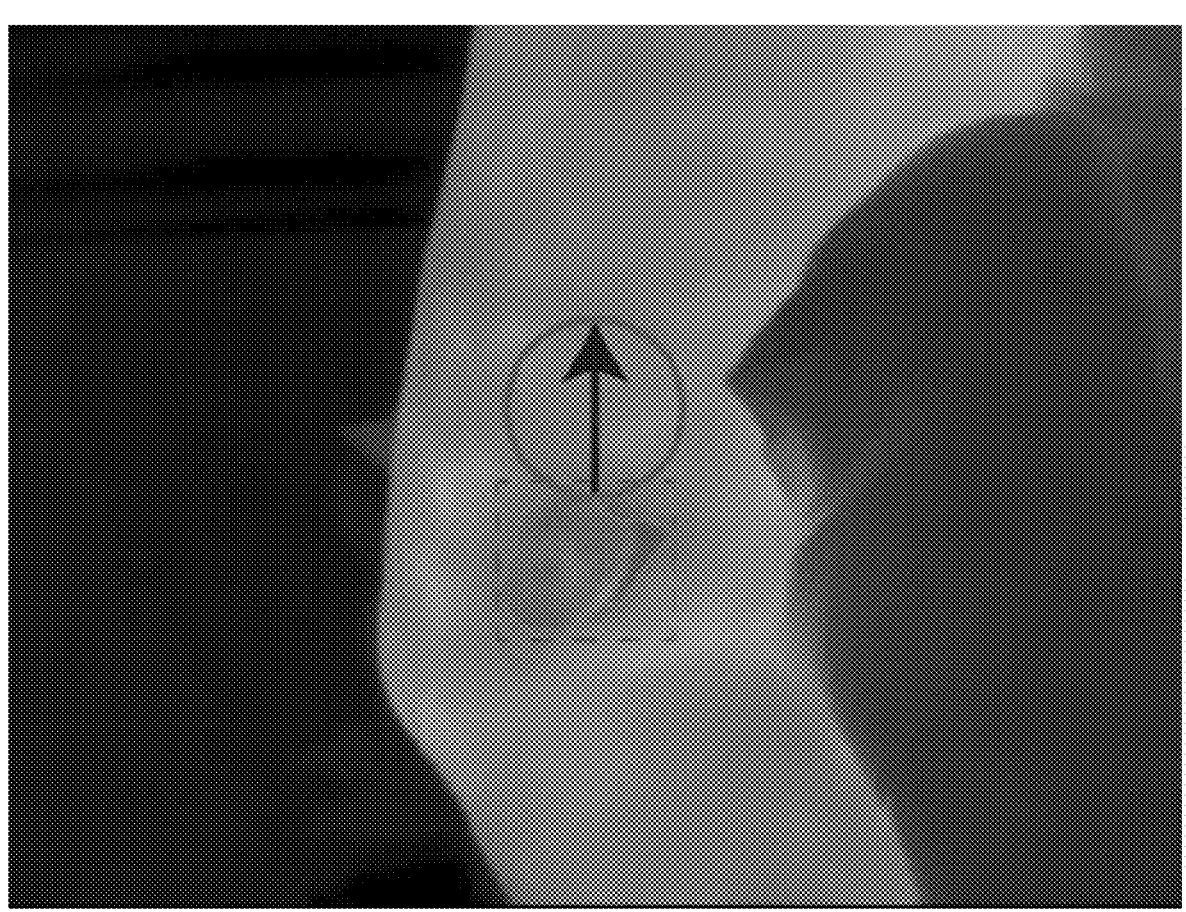

FIG. 19 shows: A photograph of a graphical method before choosing proper head direction.

Figure 20:
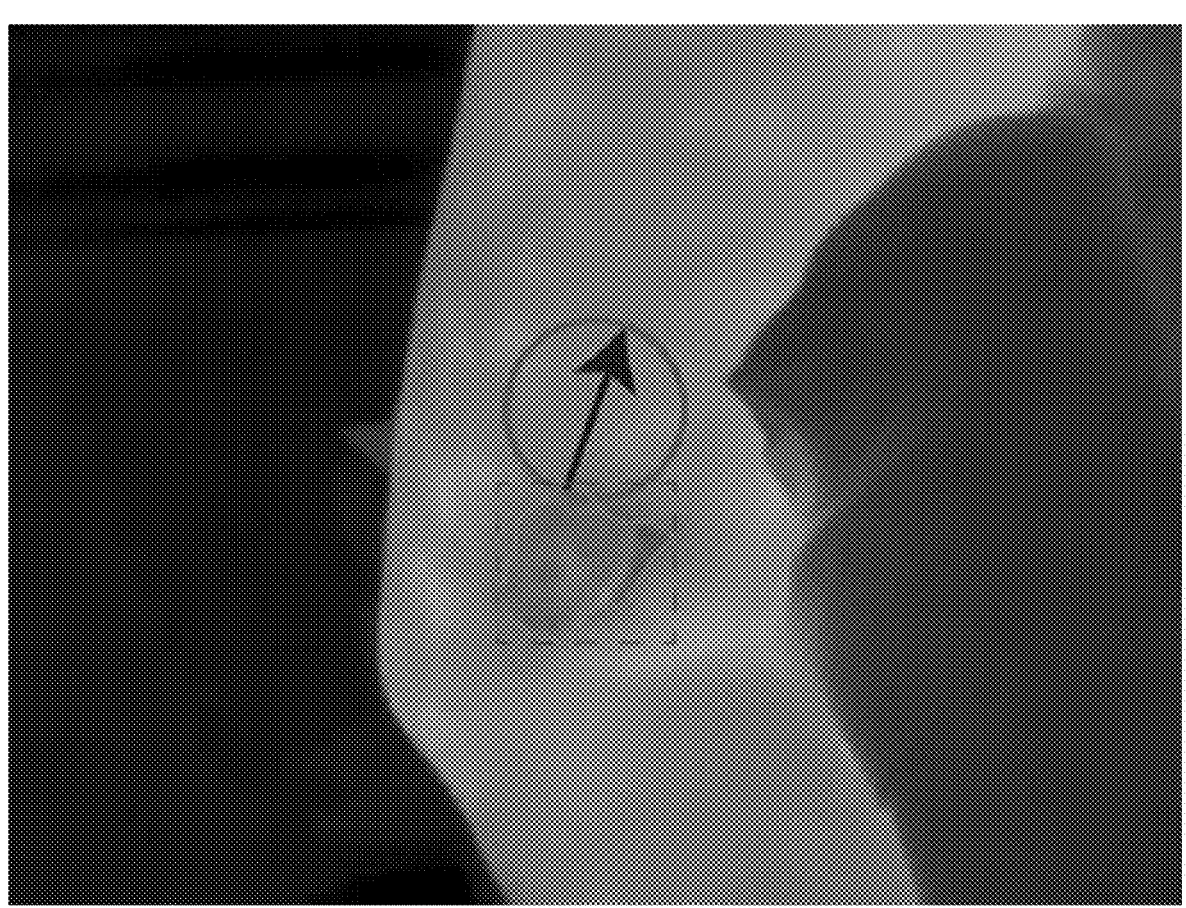

FIG. 20 shows: A photograph of the graphical method of FIG. 19 after proper head direction has determined.

Figure 21:
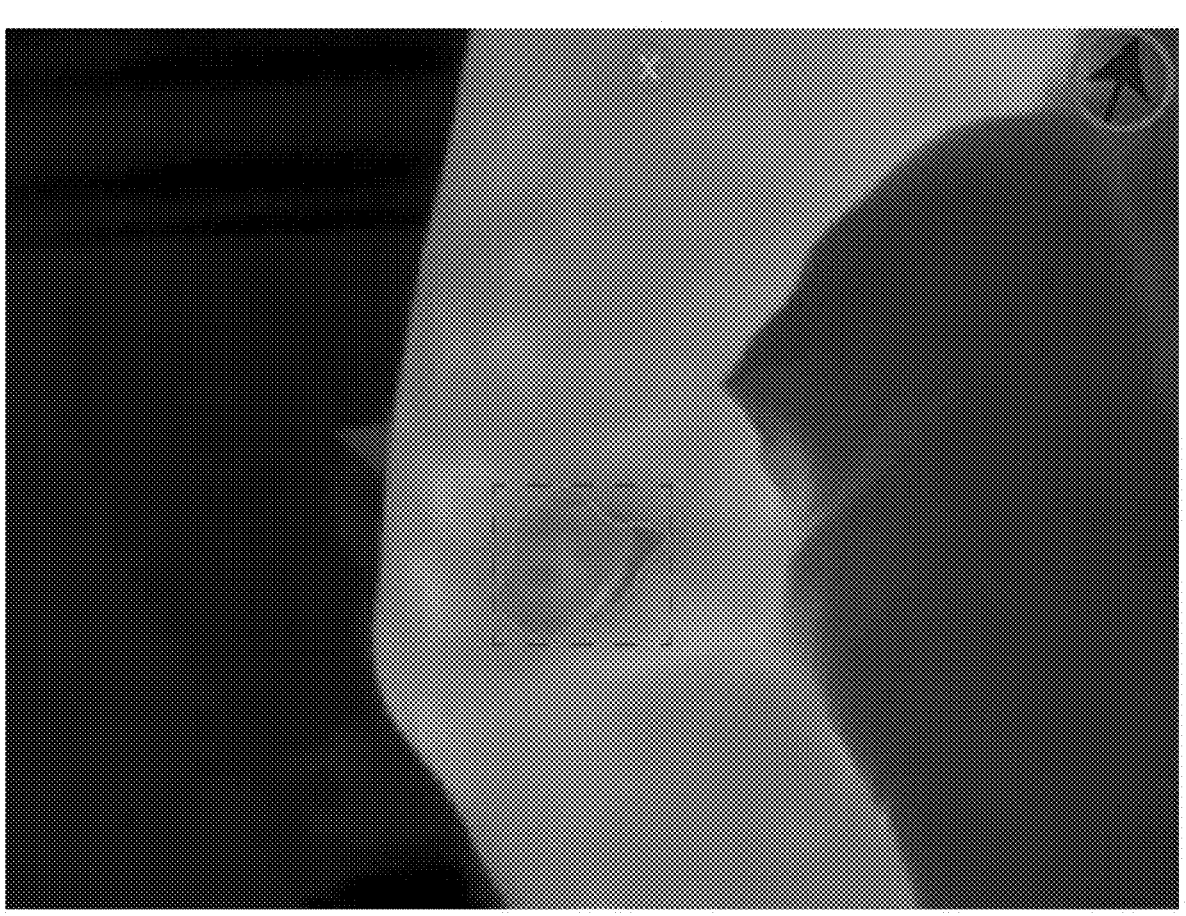

FIG. 21 shows: A photograph of an unaffected reference area displayed by the present invention.

Figure 22:
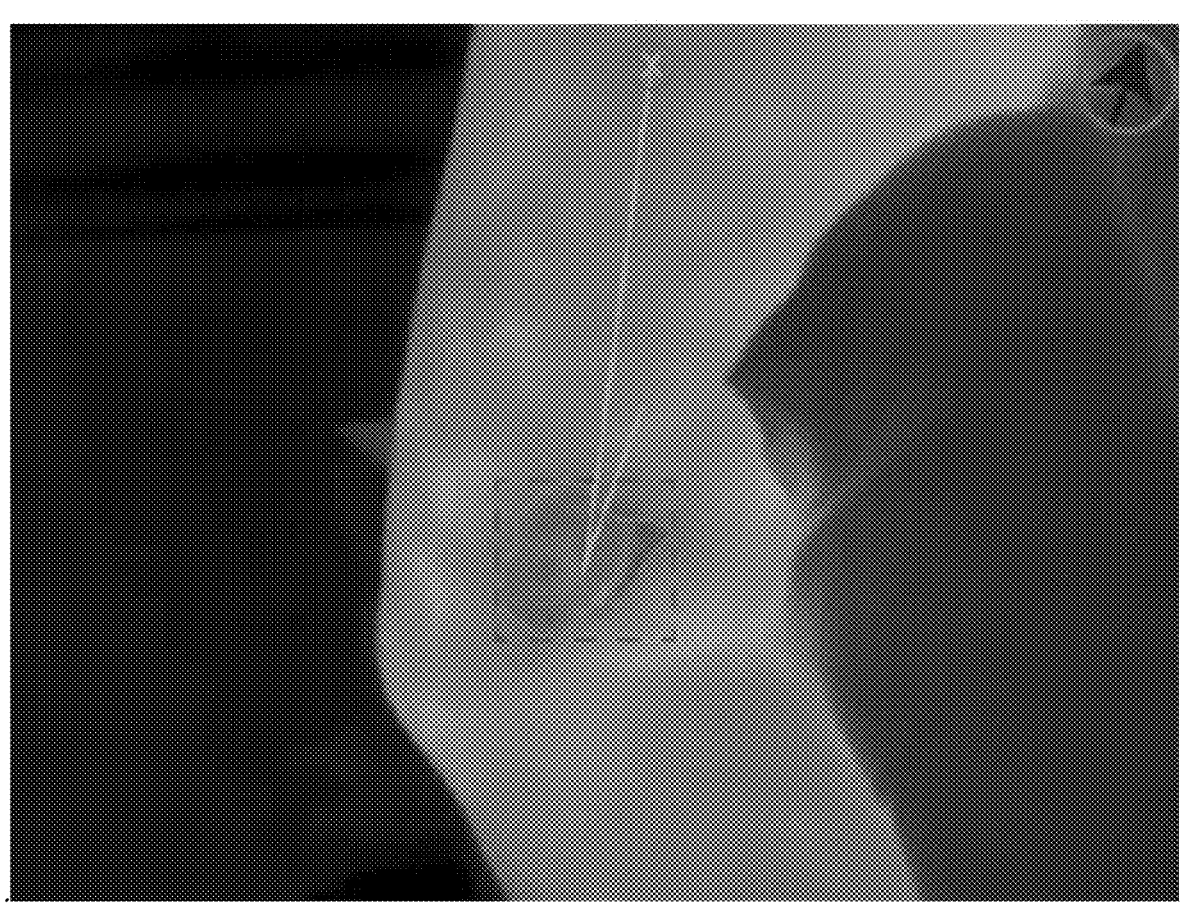

FIG. 22 shows: A photograph of a traced area, head direction, and unaffected reference area on a first day of study.

Figure 23:
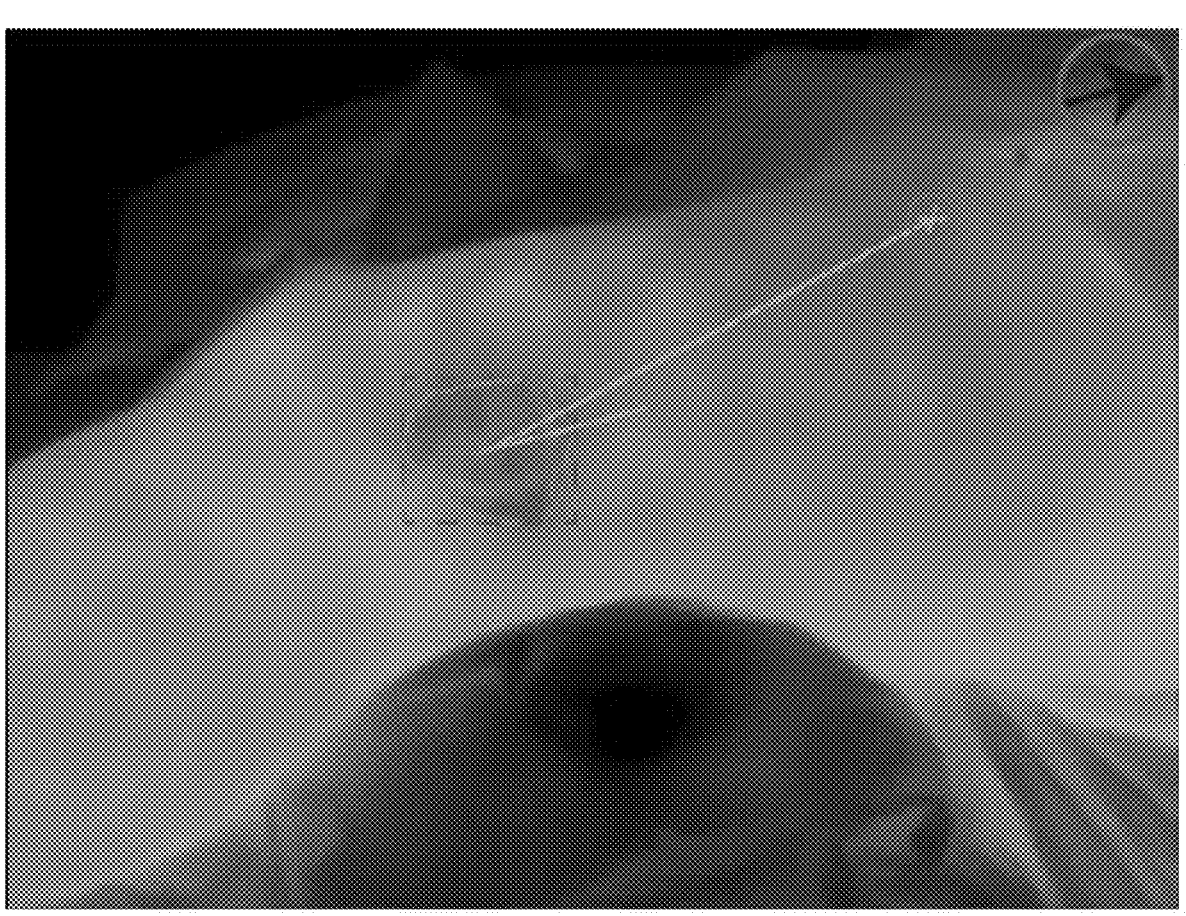

FIG. 23 shows; A photograph of the automatic unaffected reference area of FIG. 22 on a second day of study; based on traced area, head direction, and unaffected reference area from first day of study.

Figure 24:
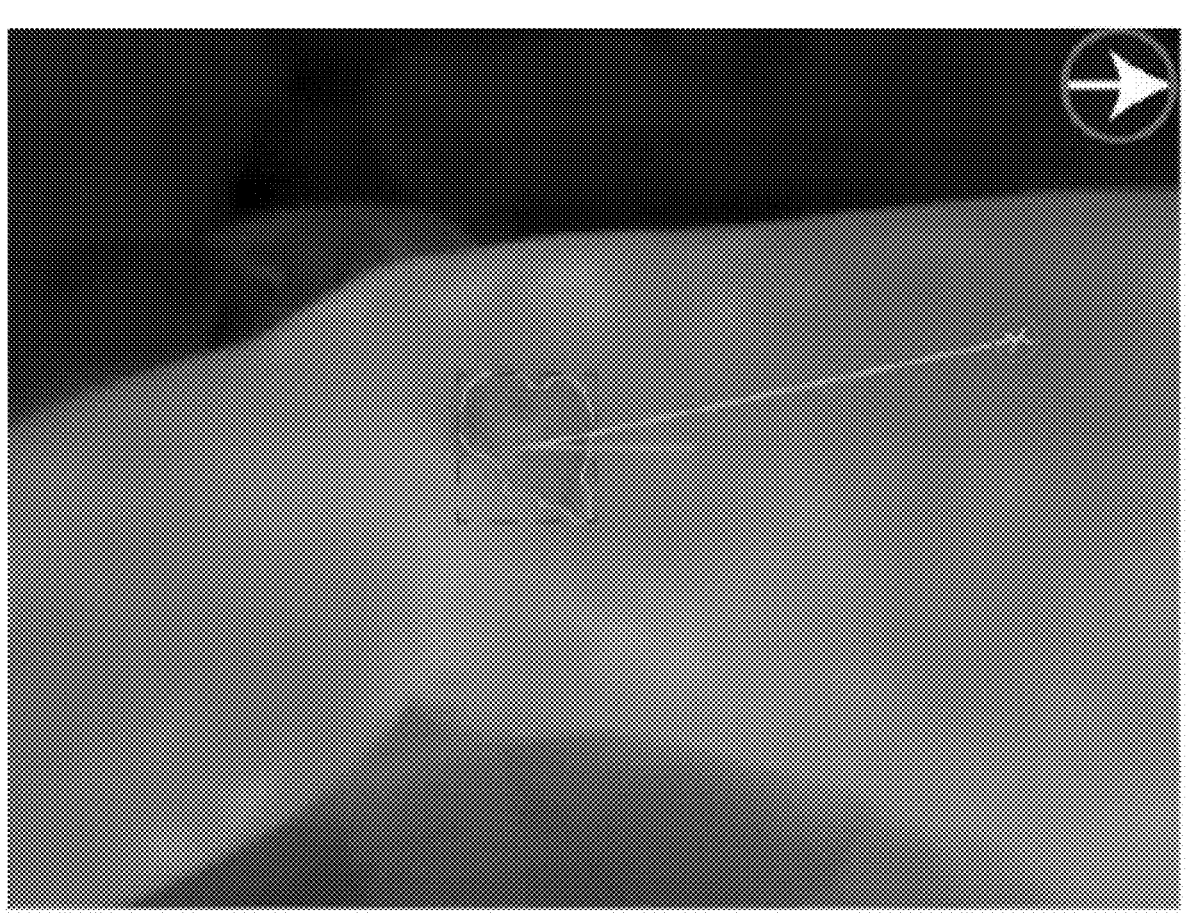

FIG. 24 shows: A photograph of the automatic unaffected reference area of FIG. 22 on a third day of study; based on traced area, head direction, and unaffected reference area from first day of study.

Figure 25:
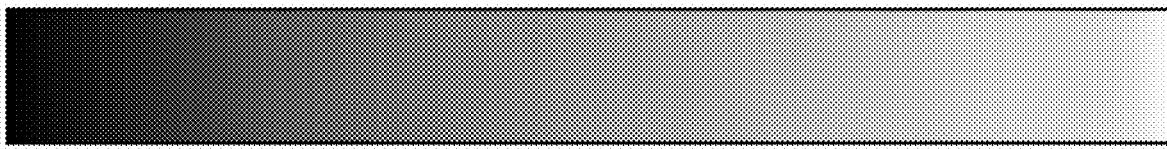

FIG. 25 shows: A non-relative "gray" scale as may be used with the present invention.

Figure 26:
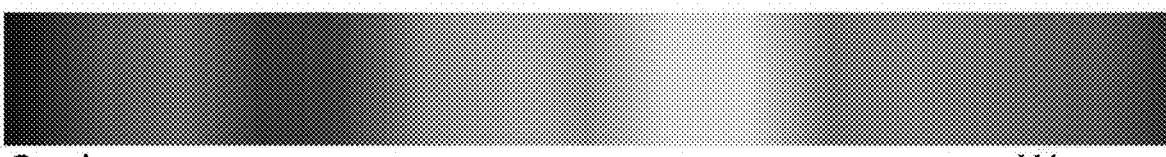

FIG. 26 shows: A non-relative "color" scale as may be used with the present invention.

Figure 27:
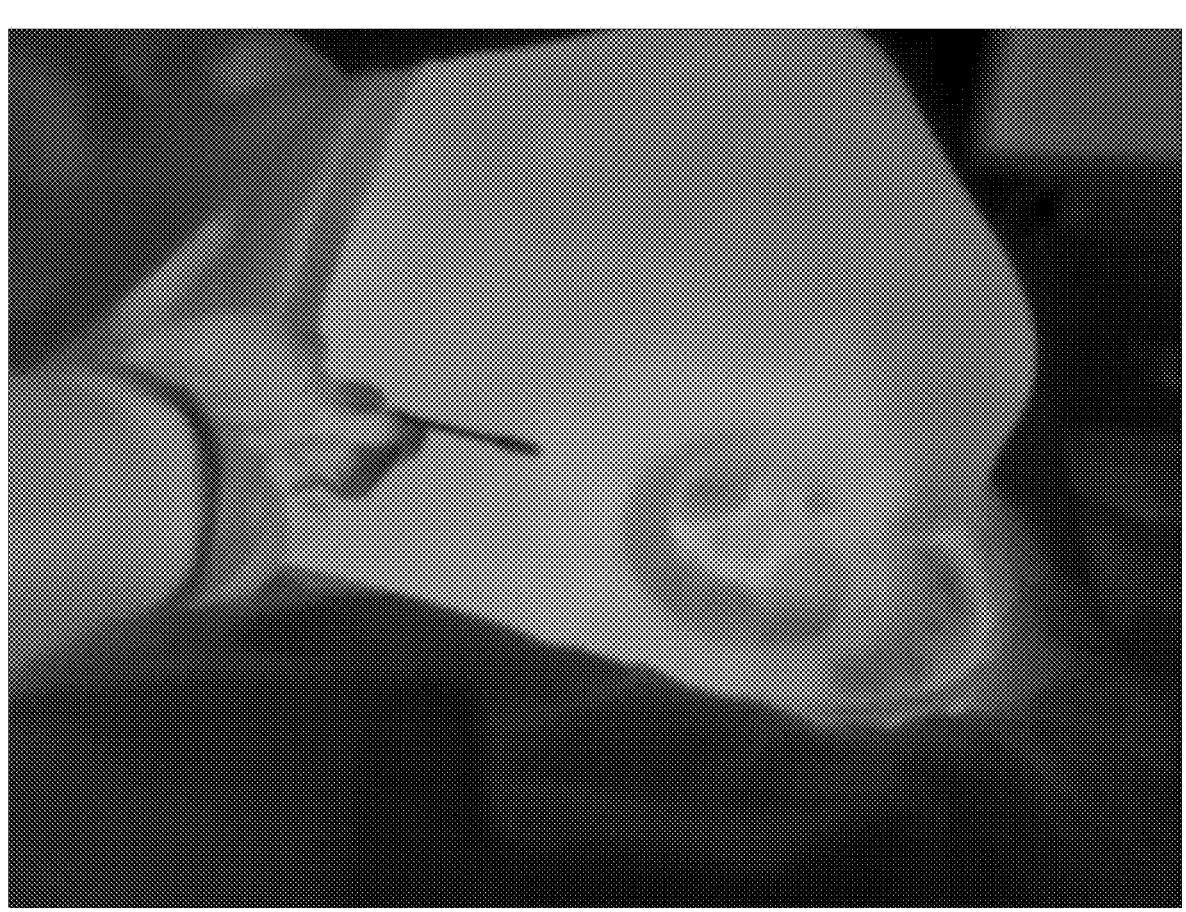

FIG. 27 shows: A gray scale image before applying a non-relative color scale.

Figure 28:
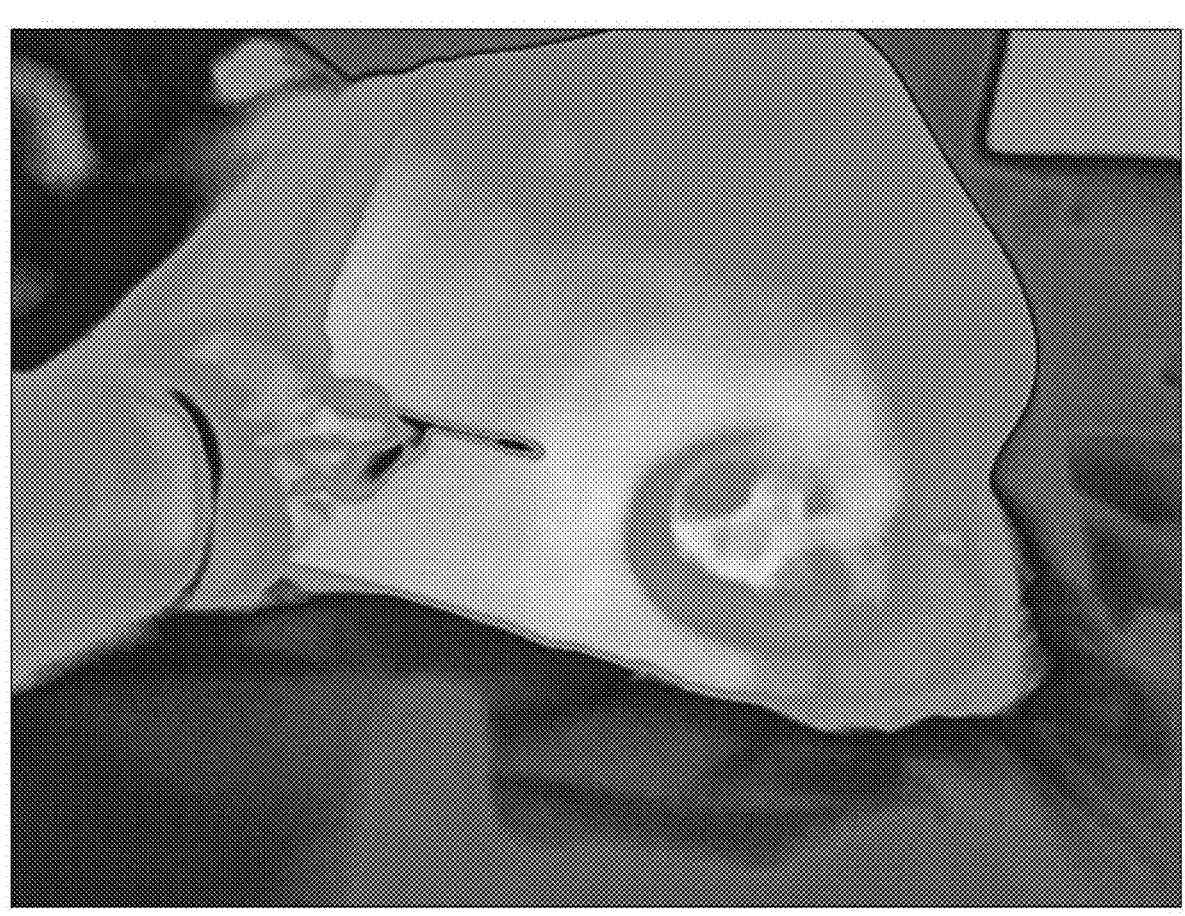

FIG. 28 shows: A non-relative color scale based on the image in FIG. 27.

Figure 29:
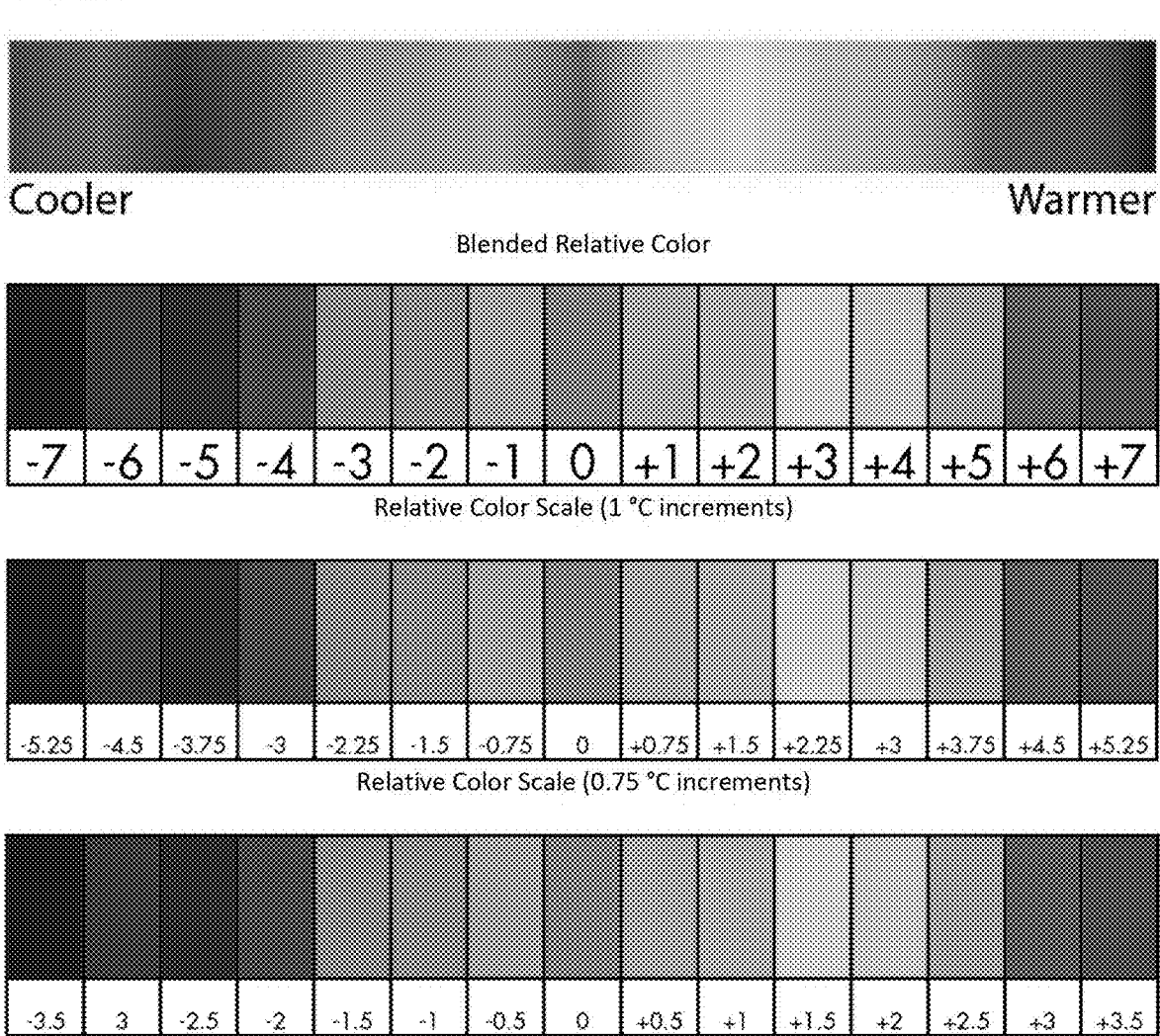

FIG. 29 shows: A relative color scale may be used with the present invention.

Figure 30:
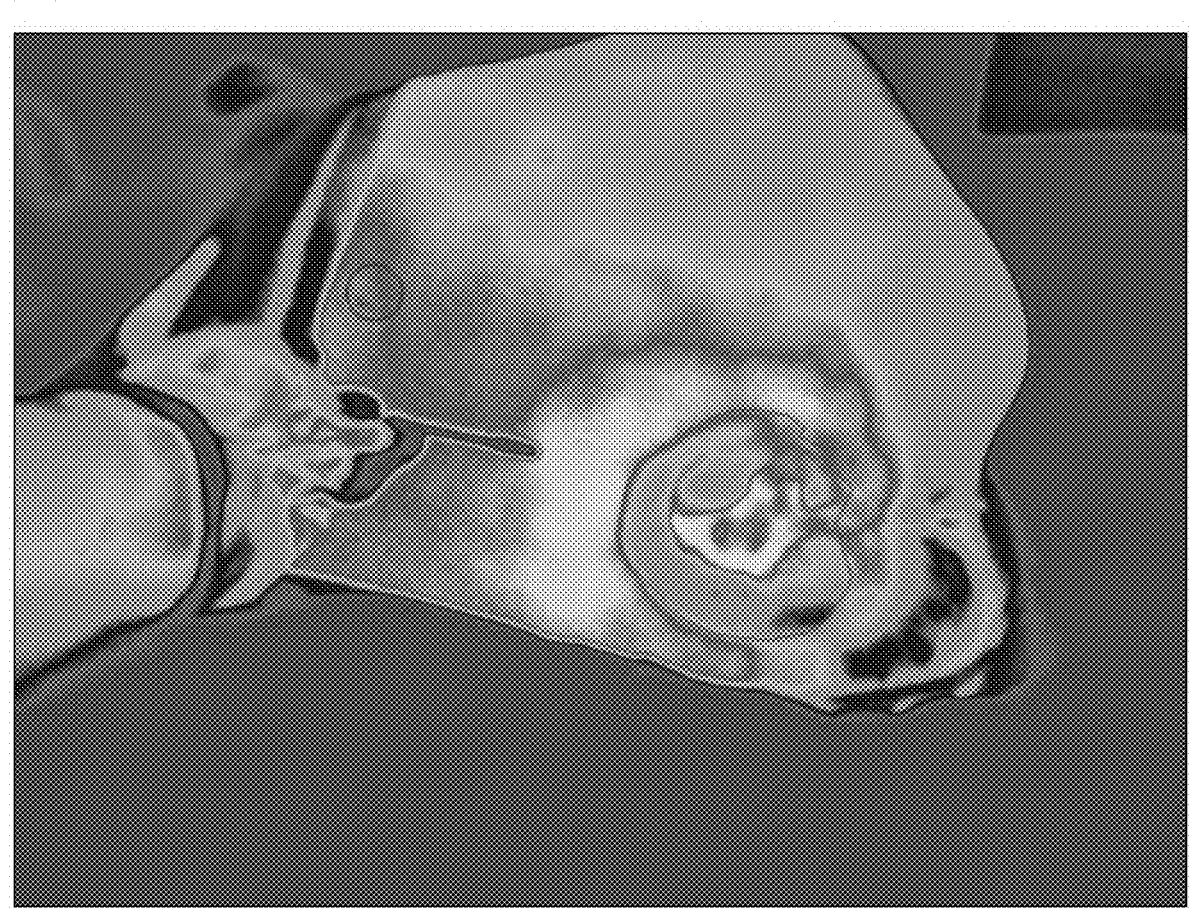

FIG. 30 shows: A relative color scale image comparing the area of interest to an unaffected reference area.

Figure 31:
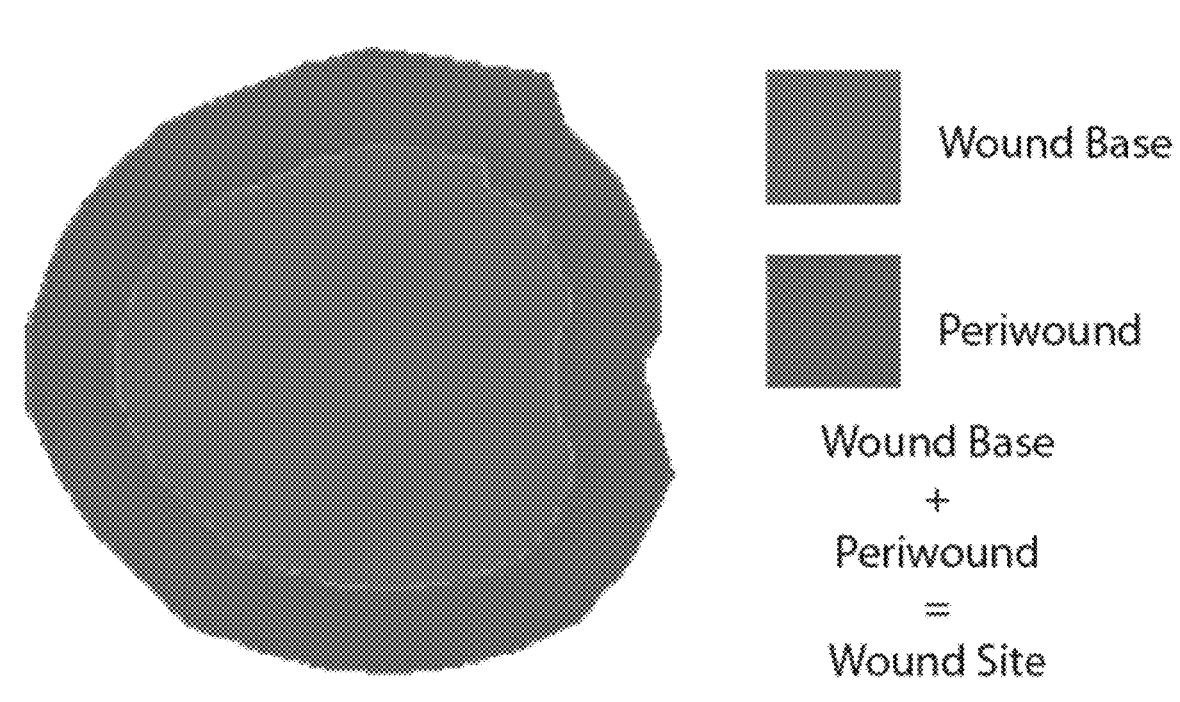

FIG. 31 shows: An exemplary graphical representation of a wound site comprising a wound base and periwound.

Figure 32:

FIG. 32 shows: A computer display of wound trace on a visual image of the body surface.

Figure 33:
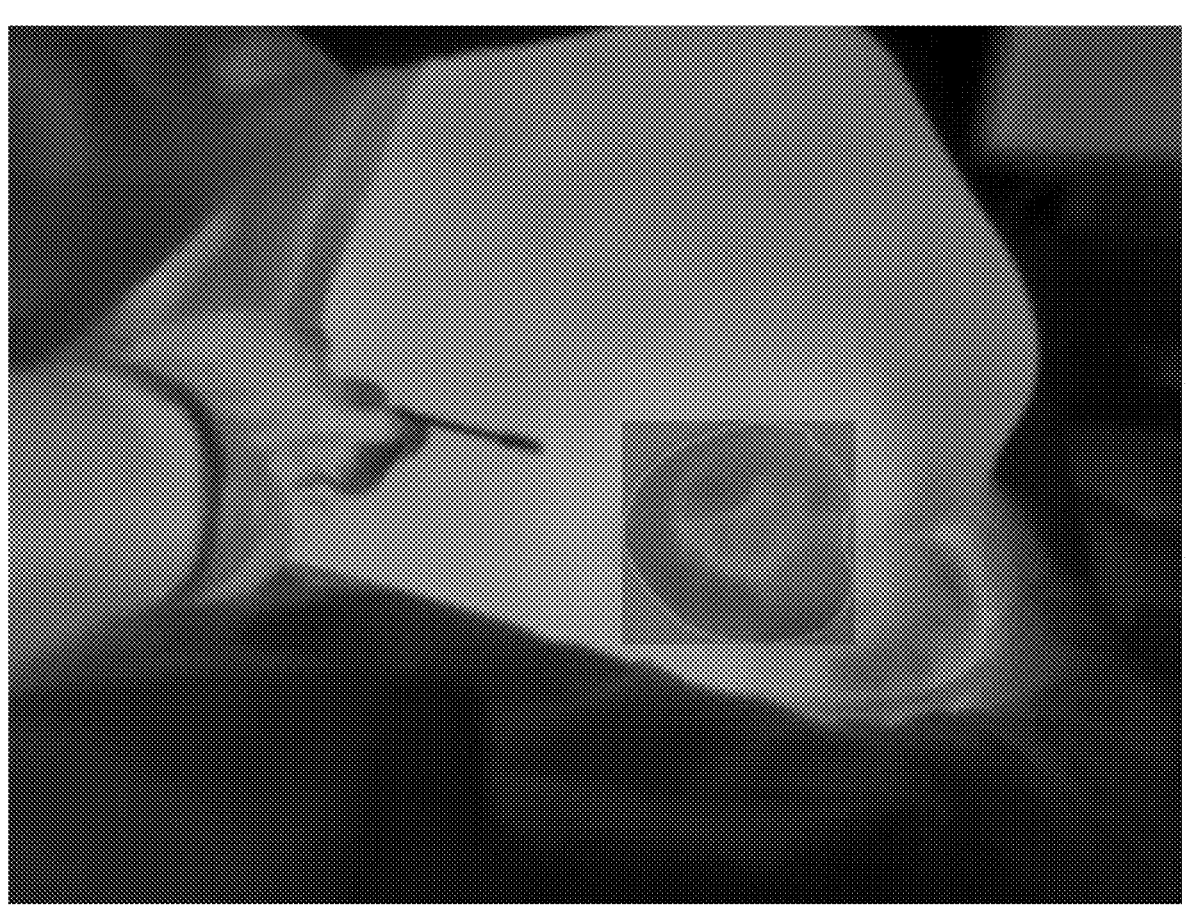

FIG. 33 shows: A photograph of a wound trace overlaid on a thermal image of the body surface.

Figure 34:
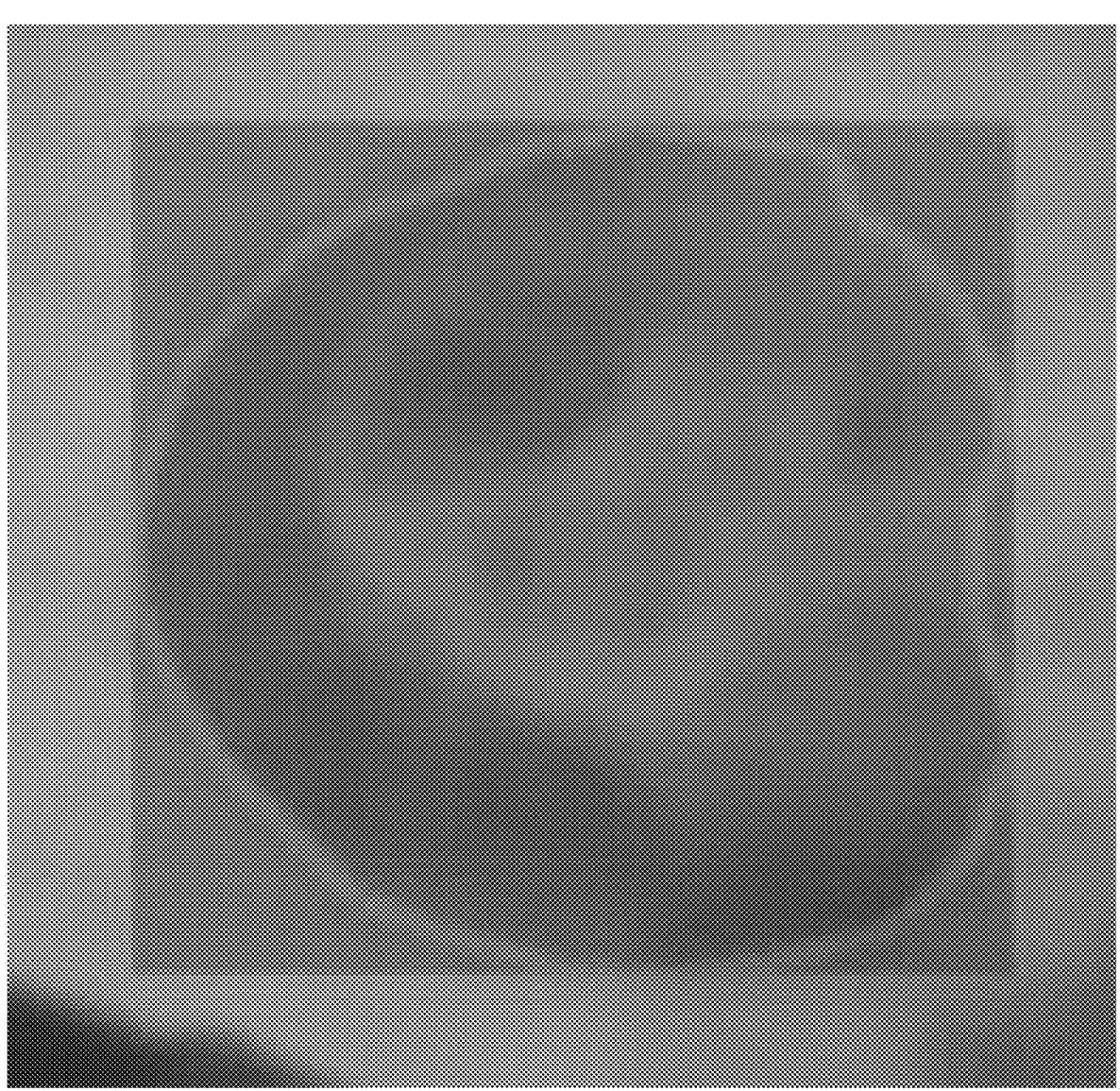

FIG. 34 shows: A close up view of FIG. 33.

Figure 35:
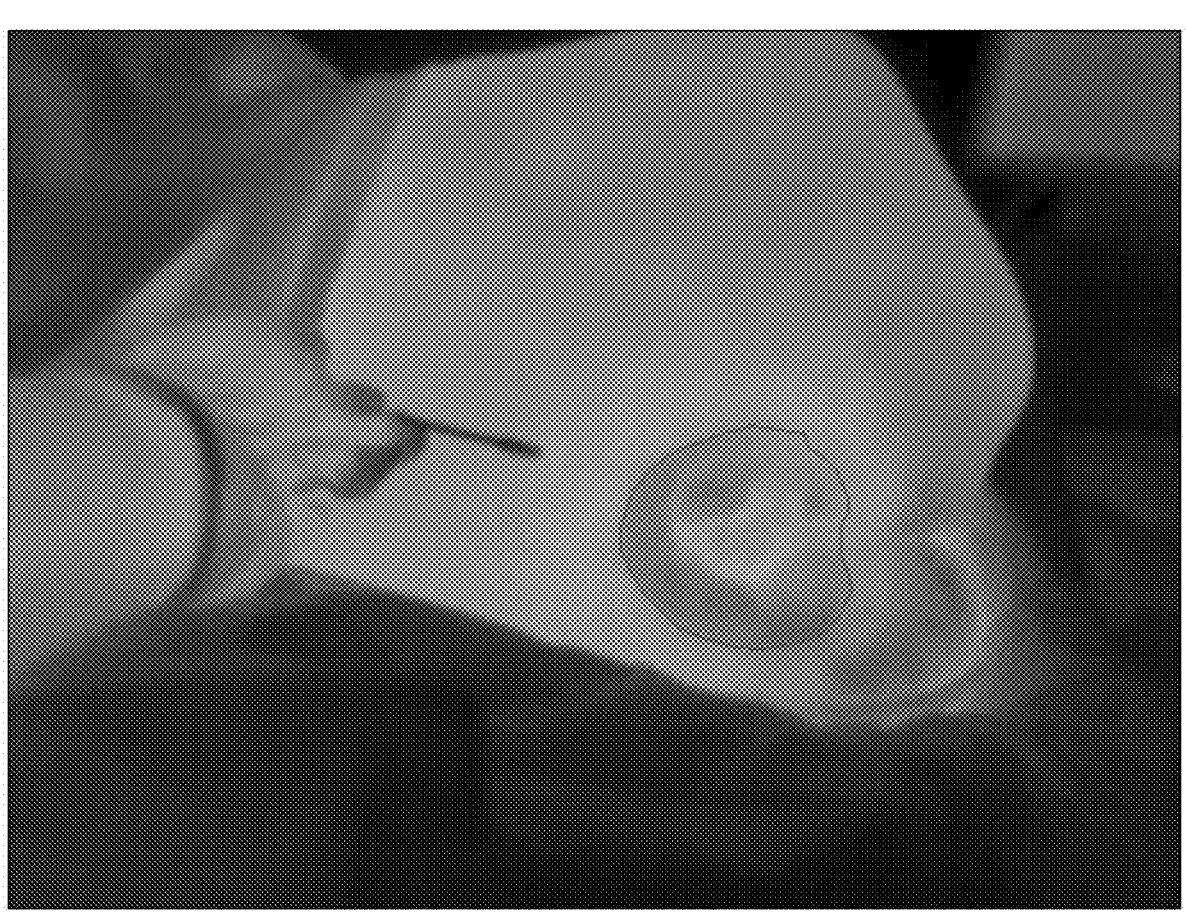

FIG. 35 shows: A photograph of a wound trace placed on a thermal image as in FIG. 33.

Figure 36:
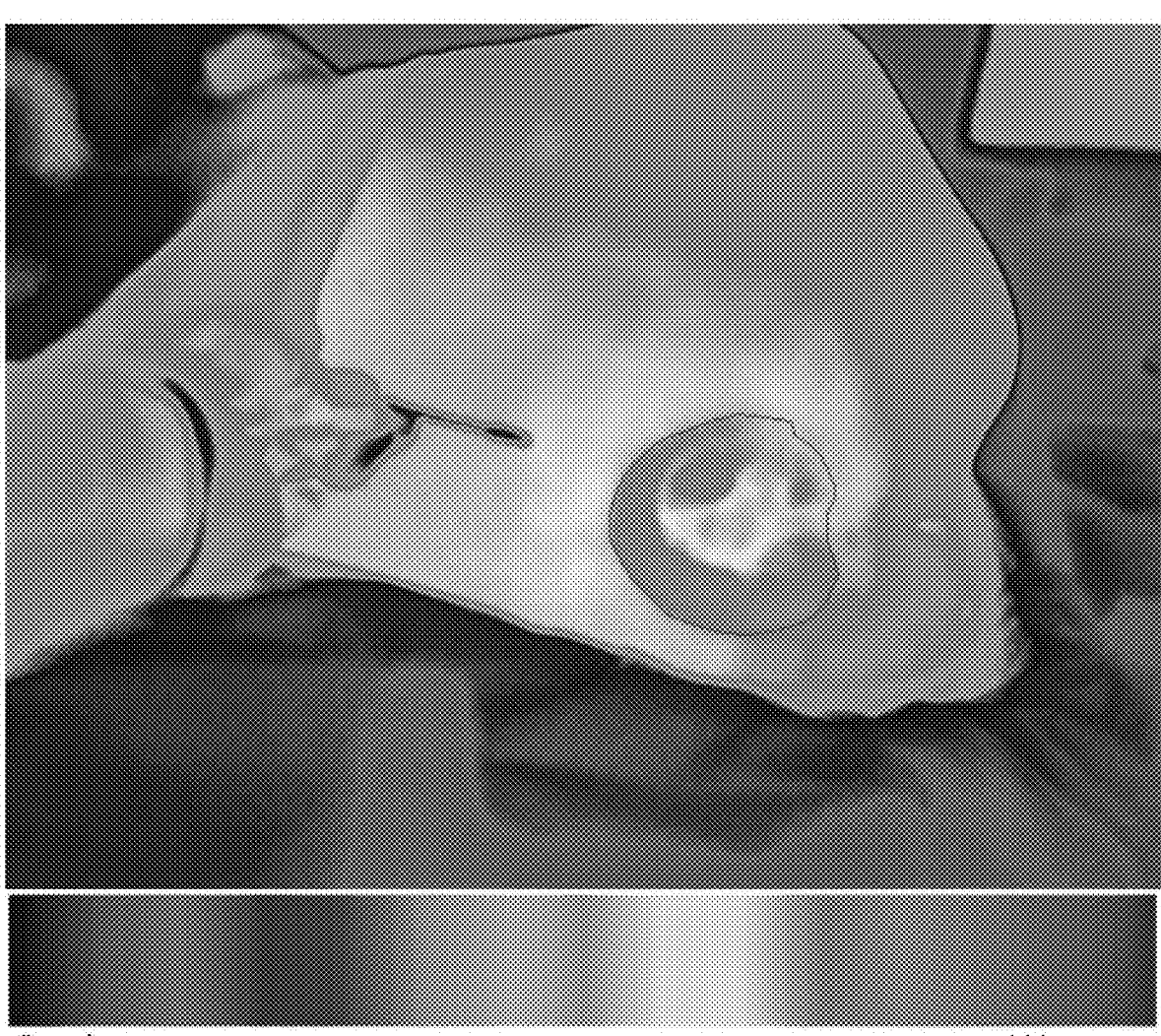

FIG. 36 shows: A photograph of the display of FIG. 35 with a non-relative color scale.

Figure 37:
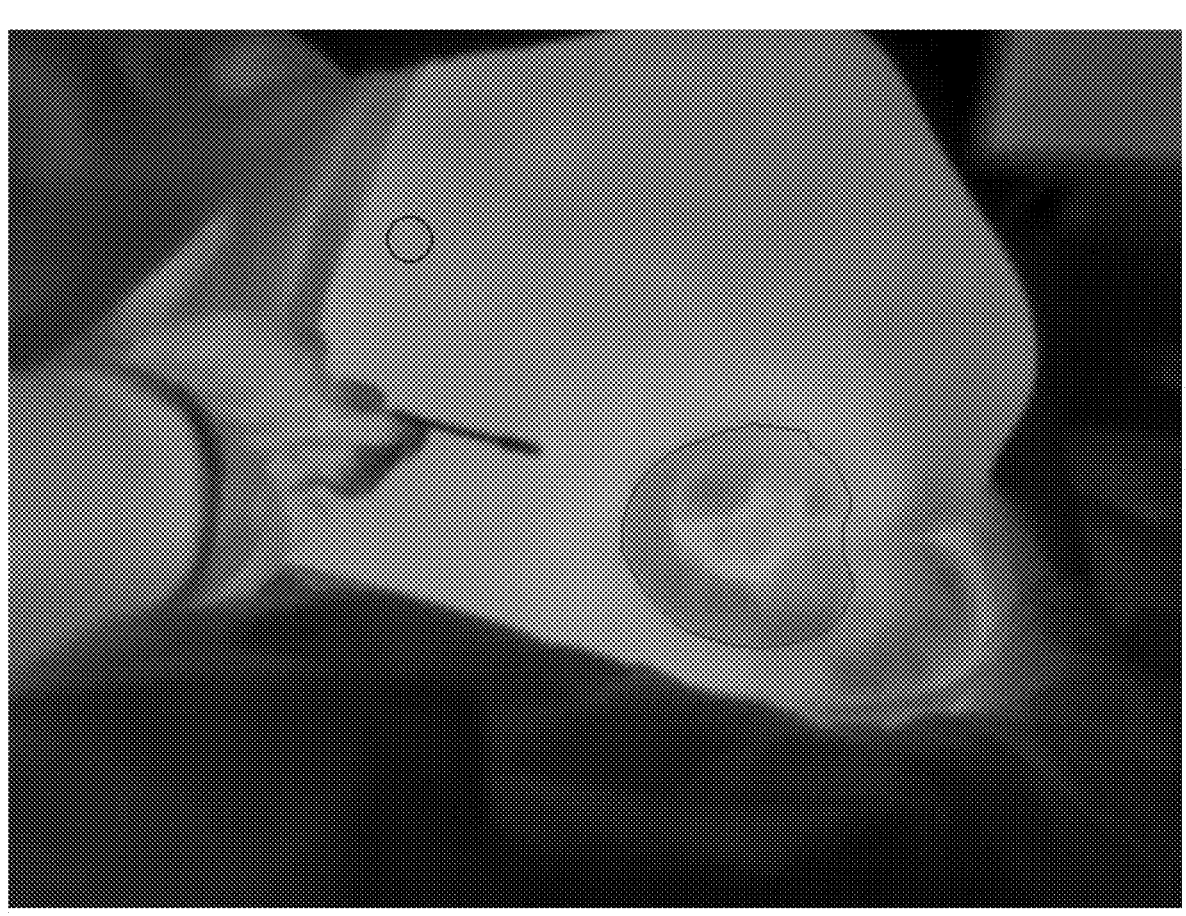

FIG. 37 shows: A photograph of the wound of FIG. 33 with an unaffected reference area selected.

Figure 38:
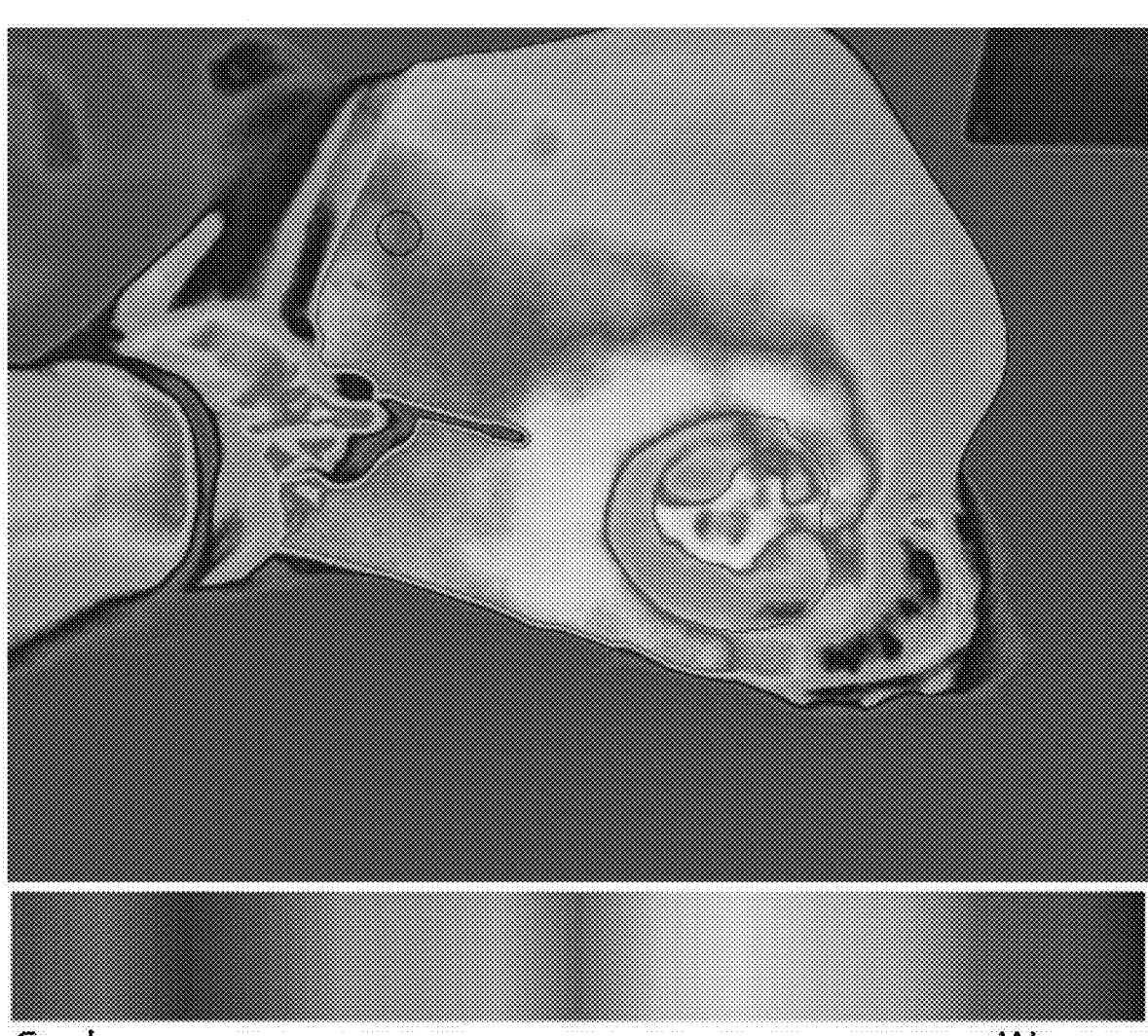

FIG. 38 shows: A photograph of an overlaid wound trace and unaffected reference area on a thermal image with a relative color scale.

Figure 39:
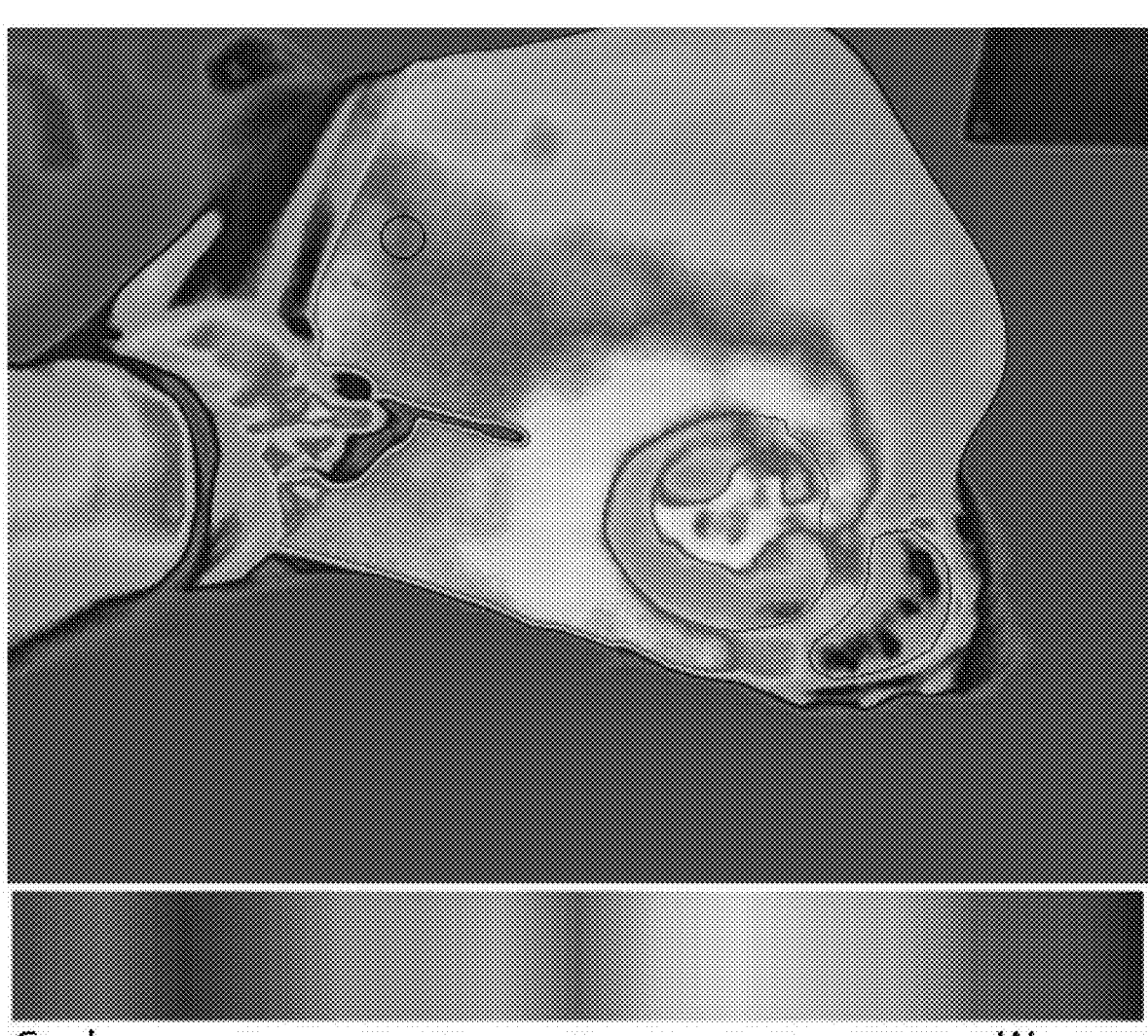

FIG. 39 shows: A photograph of an overlaid wound trace, unaffected reference area, and area of interest trace on a thermal image with a relative color scale.

Figure 40:
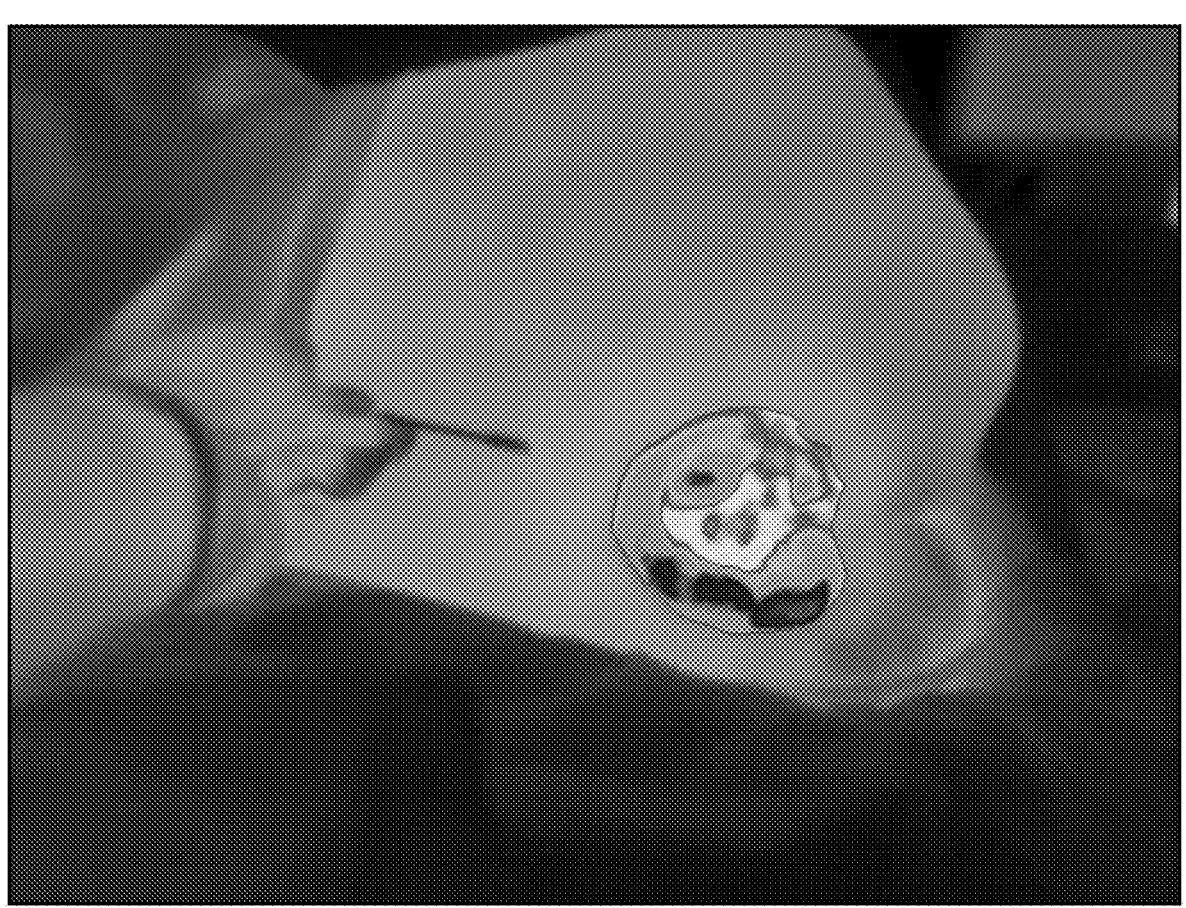

FIG. 40 shows: A photograph of the relative color wound bend of FIG. 38 combined with a non-relative gray scale image.

Figure 41:
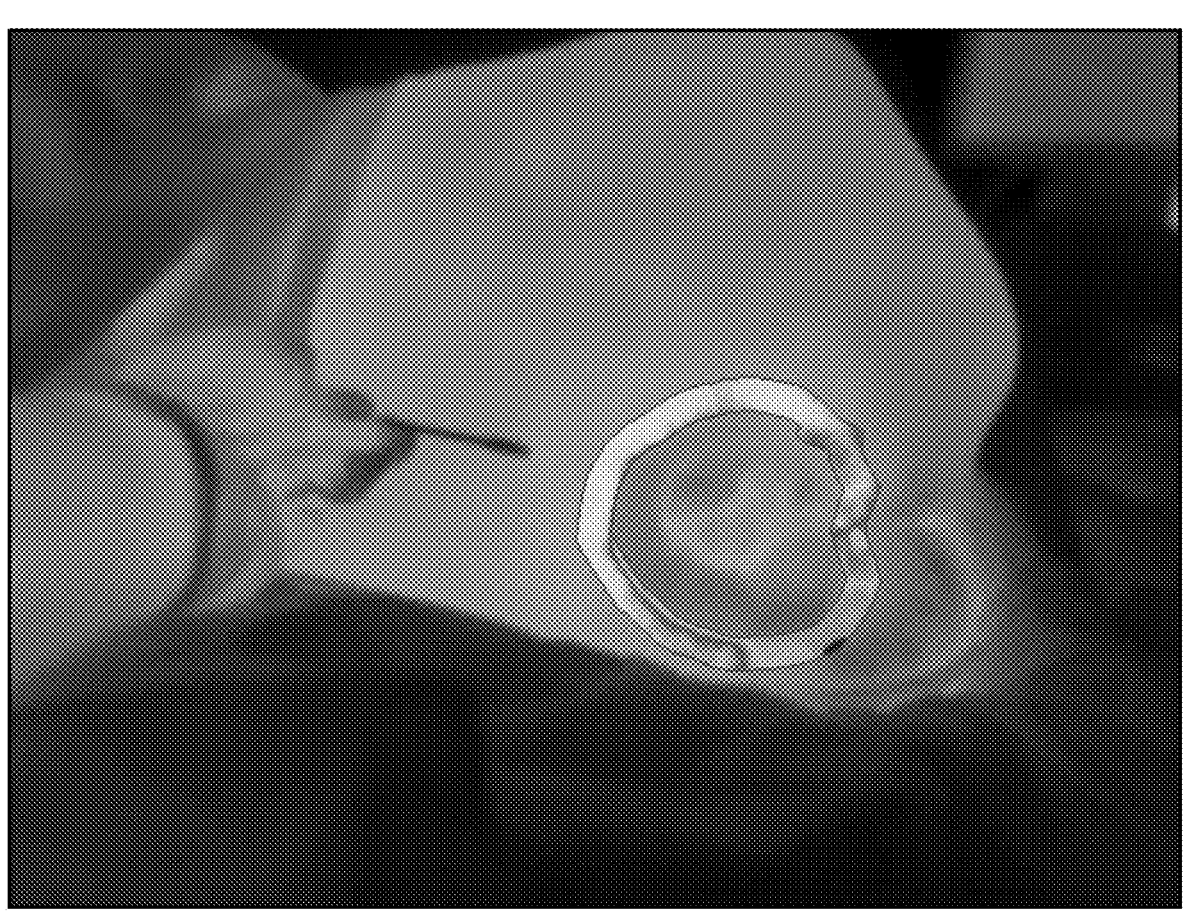

FIG. 41 shows: A photograph of the relative color periwound of FIG. 38 combined with a non-relative gray scale image.

Figure 42:
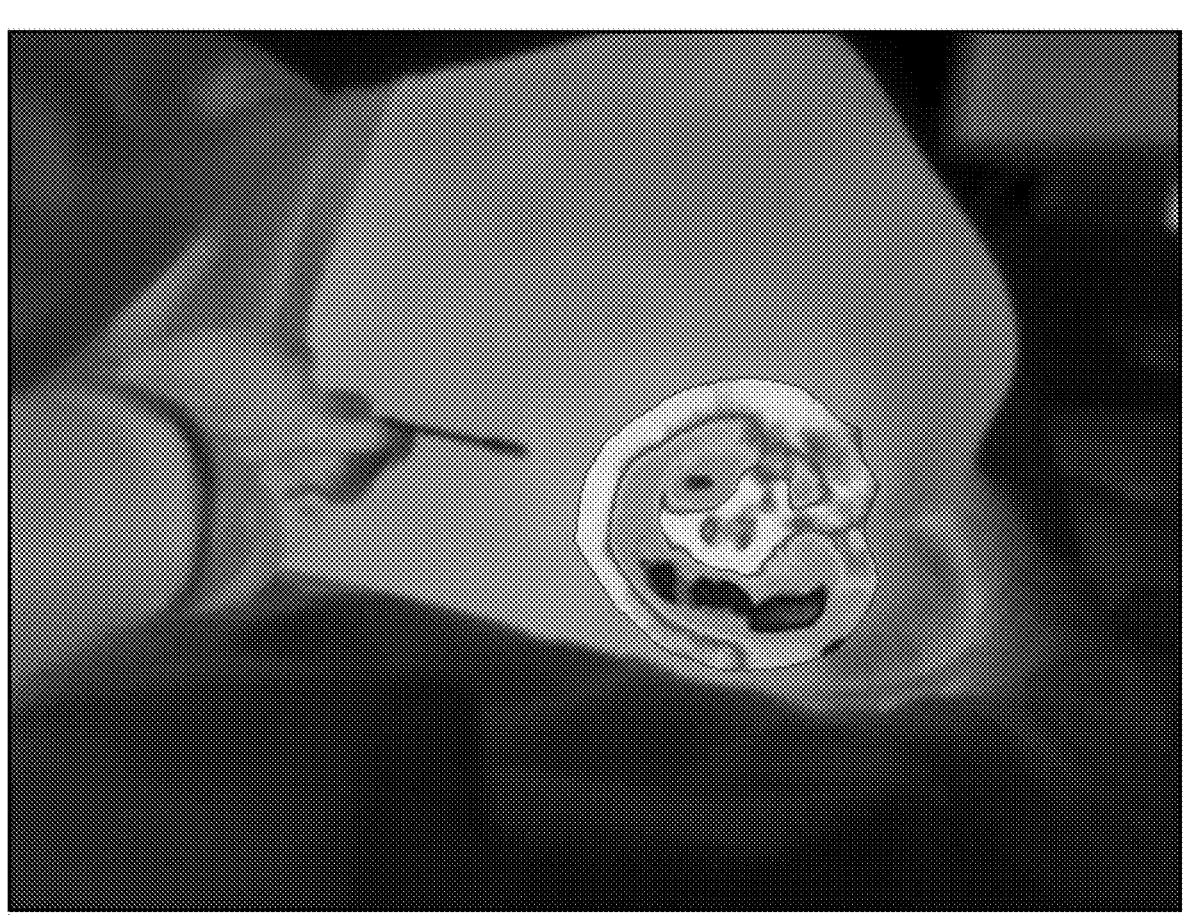

FIG. 42 shows: A photograph of the relative color wound site of FIG. 38 combined with a non-relative gray scale image.

Figure 43A:
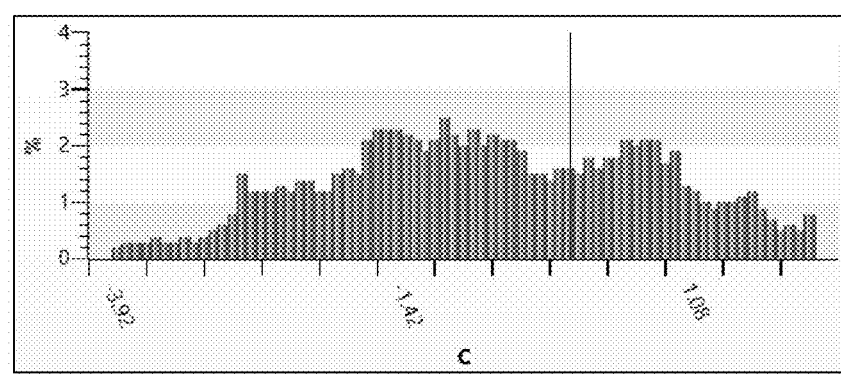

FIG. 43 includes FIGS. 43A to 43D. FIG. 43A shows: A plot of relative temperature histogram data from the wound bed, periwound, wound site, and unaffected reference area.

Figure 43B:
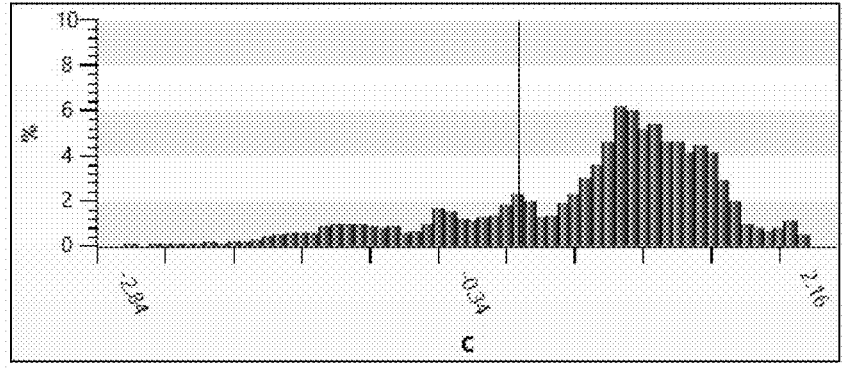

FIG. 43B shows: A plot of relative temperature histogram data from the wound bed, periwound, wound site, and unaffected reference area.

Figure 43C:
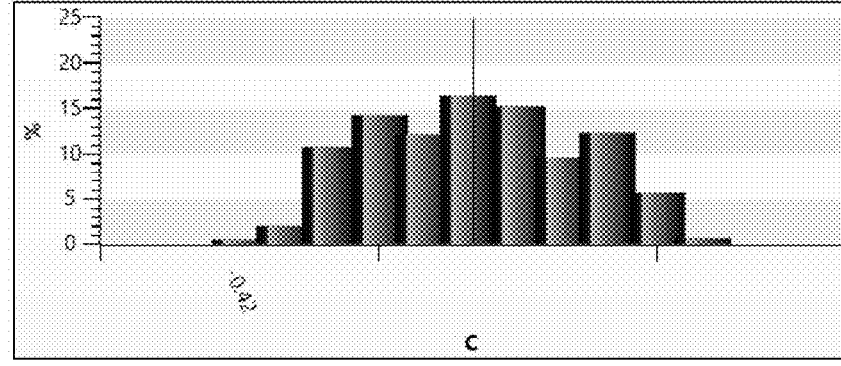

FIG. 43C shows: A plot of relative temperature histogram data from the wound bend, periwound, wound site, and unaffected reference area.

Figure 43D:
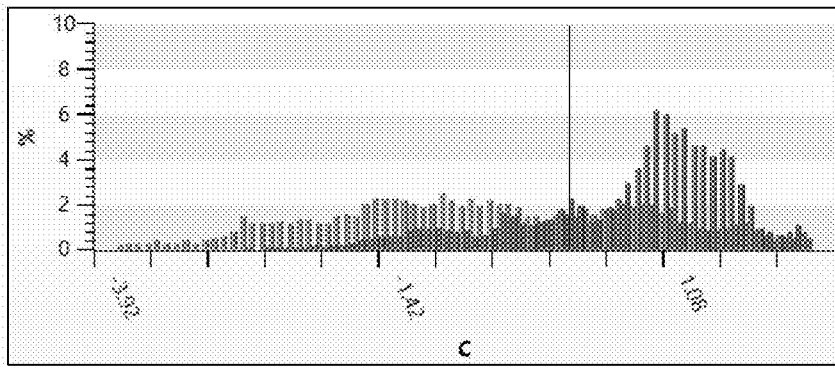

FIG. 43D shows: A plot of relative temperature histogram data from the wound bend, periwound, wound site, and unaffected reference area.

FIG. 44 shows: An exemplary algorithm for calculating the wound trace, overlaid wound trace, periwound trace, wound site trace, general (area of interest) trace and unaffected reference area in the manner of the present invention.

Figure 45:
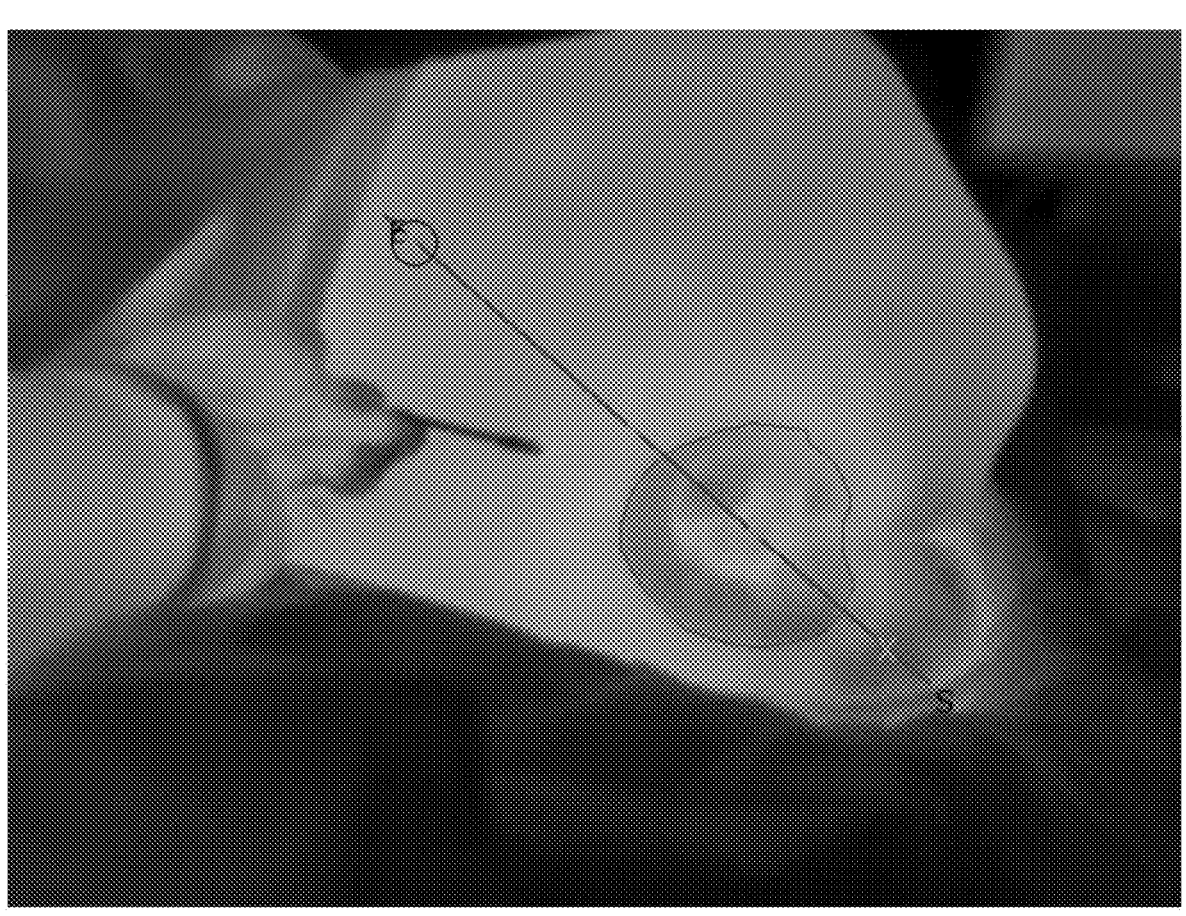

FIG. 45 shows: A photograph of a wound trace in profile line.

Figure 46:
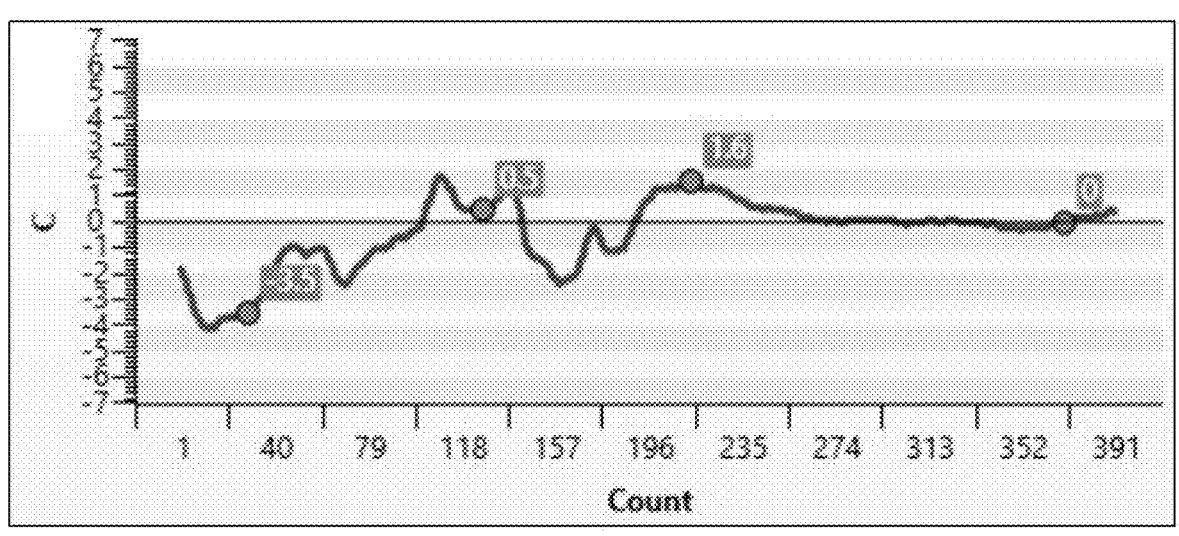

FIG. 46 shows: A plot of the profile line of FIG. 45.

Figure 47:
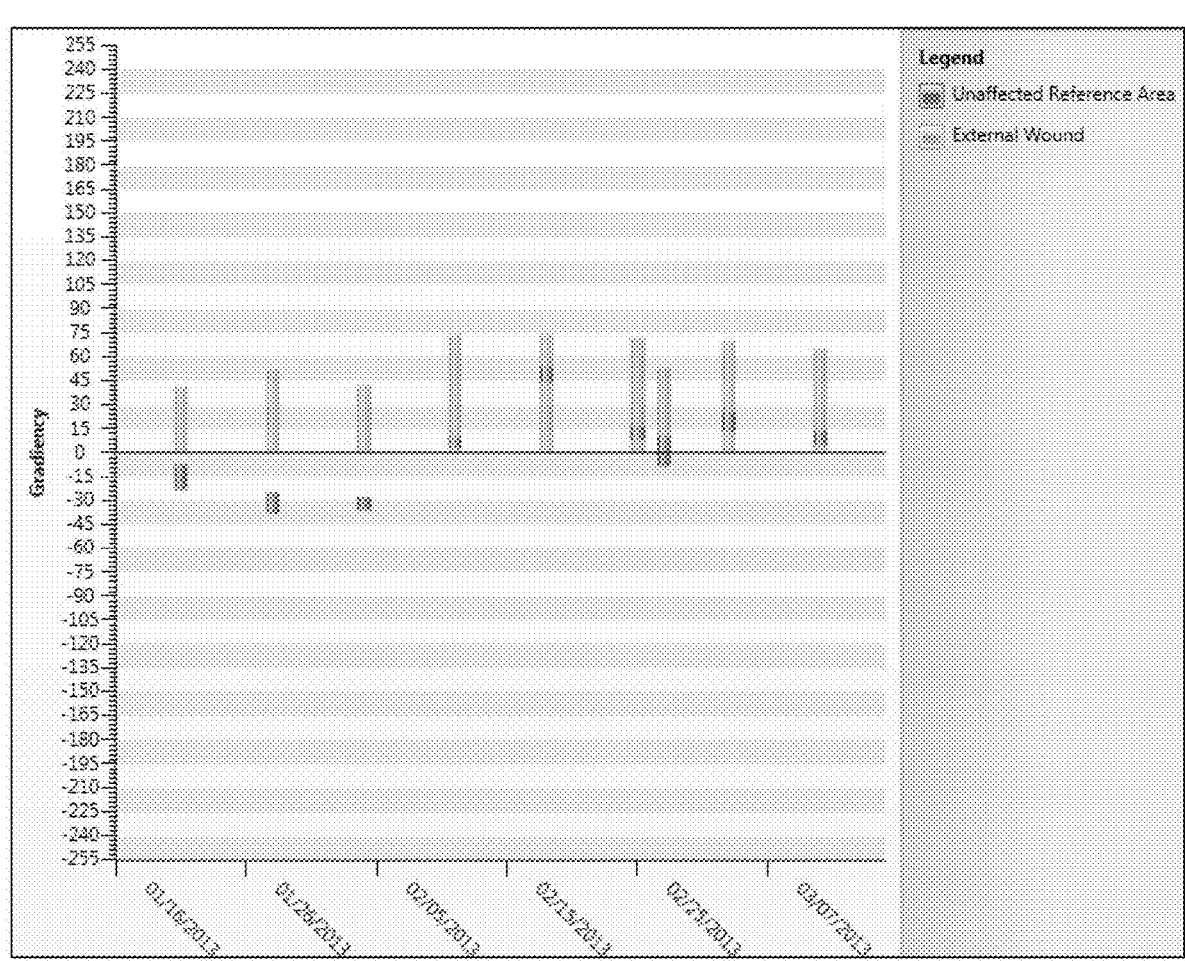

FIG. 47 shows: A plot of temperature gradiency of a wound bend.

Figure 48:
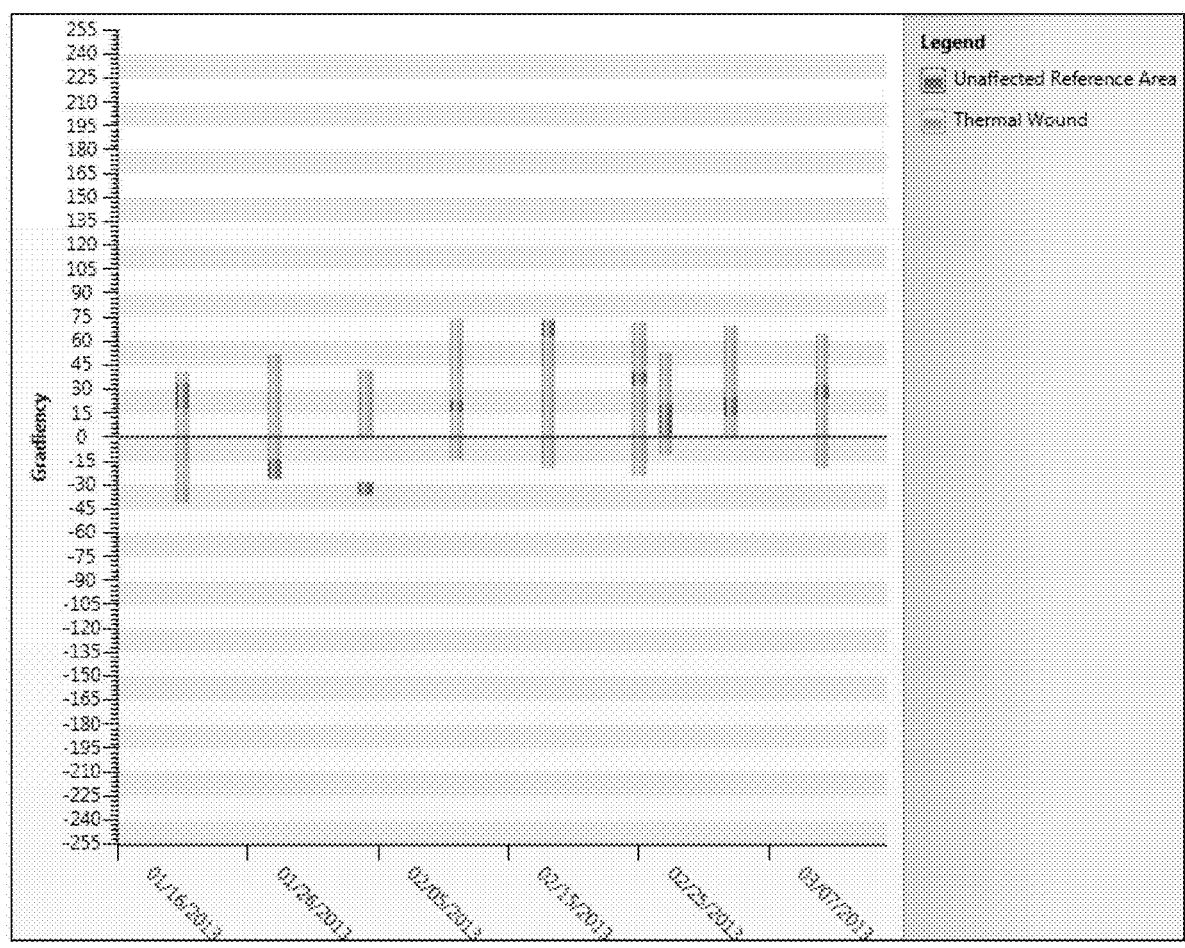

FIG. 48 shows: A plot of the temperature gradiency of a periwound.

Figure 49:
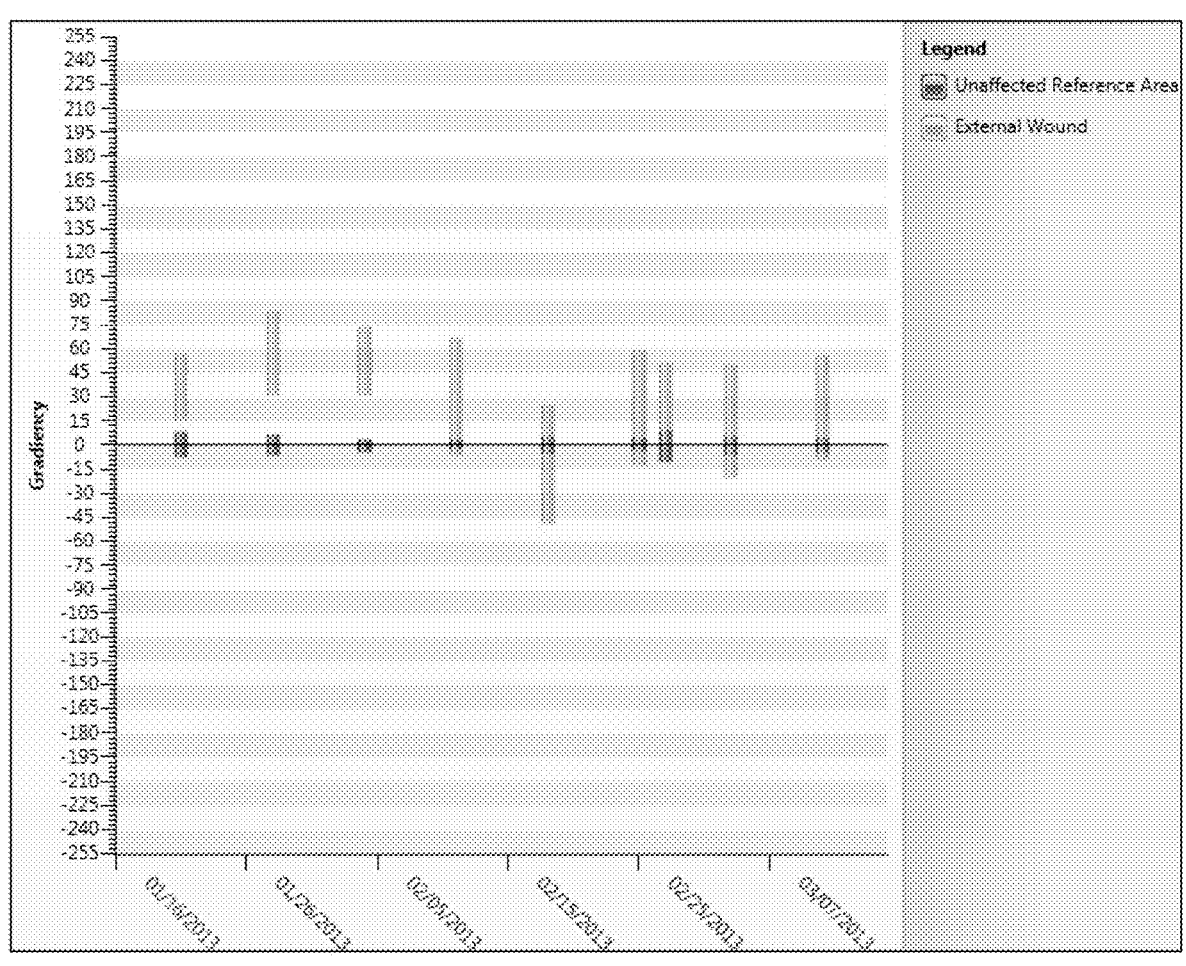

FIG. 49 shows: A plot of the temperature gradiency of the wound bed based on the unaffected reference area.

Figure 50:
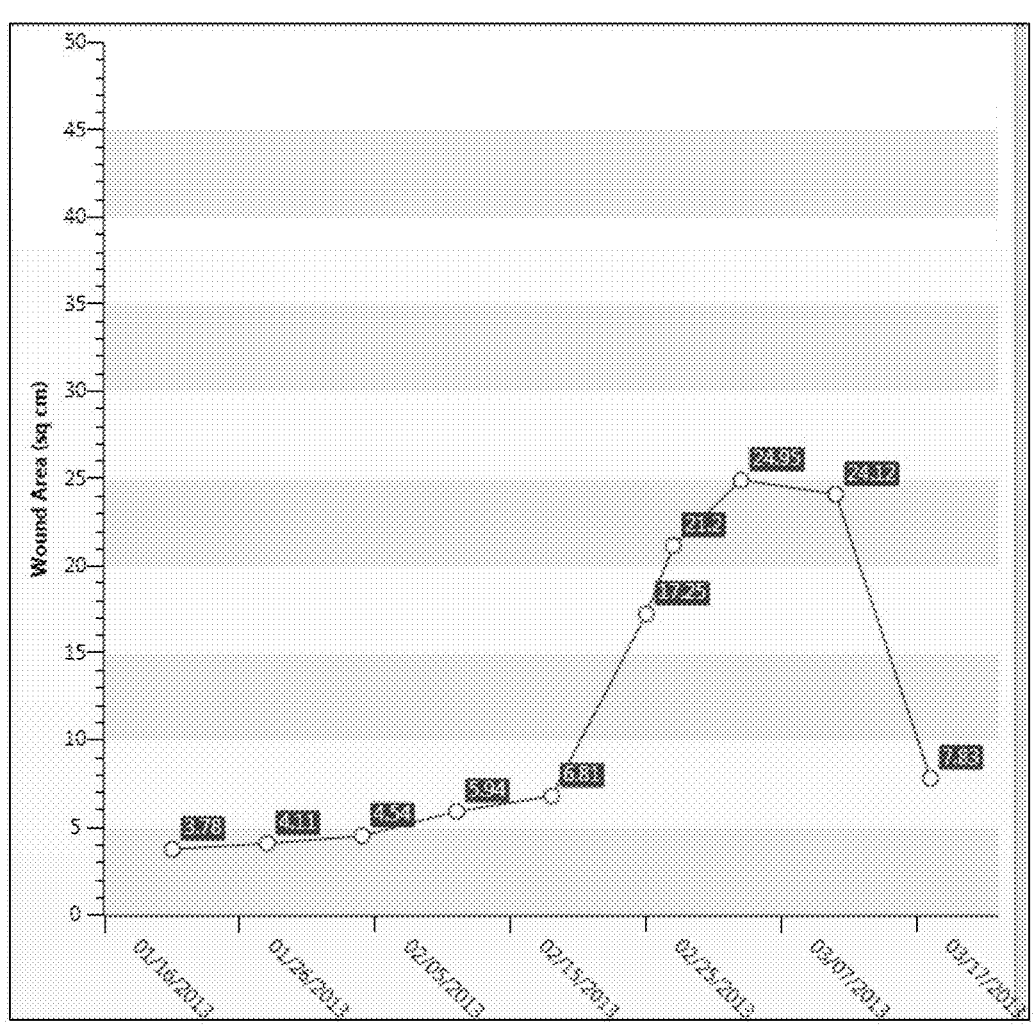

FIG. 50 shows: A plot of the wound bed area.

Figure 51:
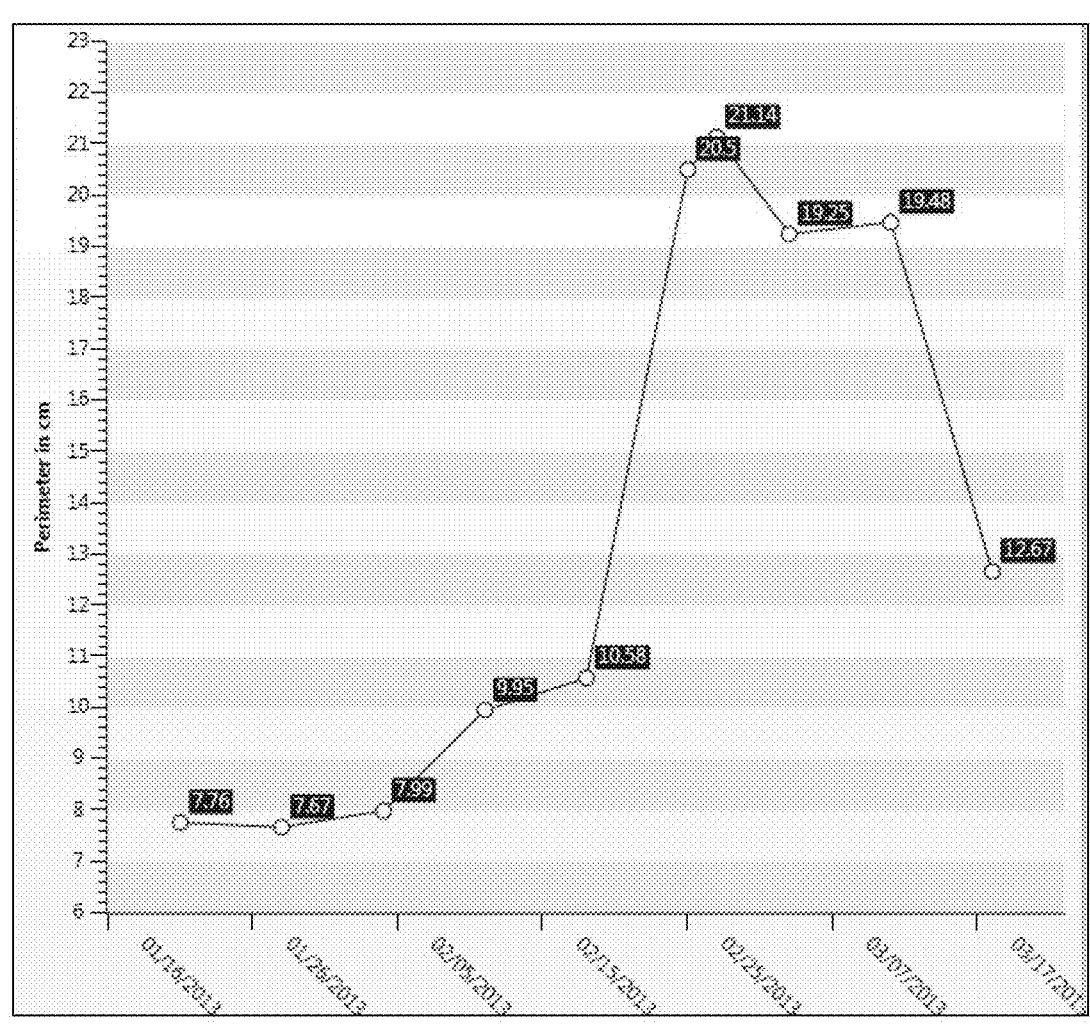

FIG. 51 shows: A plot of the wound bed perimeter.

Figure 52:
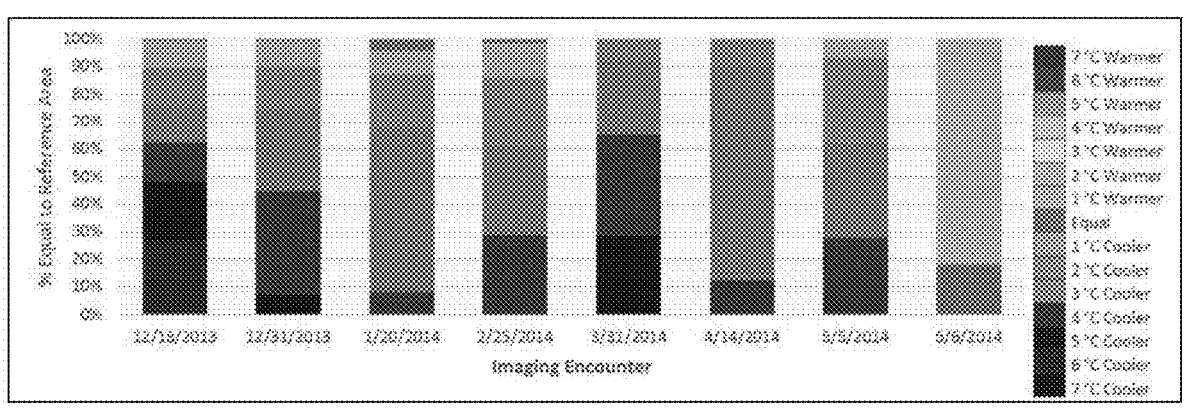

FIG. 52 shows: A plot of wound bed temperature gradiency compared to an unaffected area.

Figure 53:
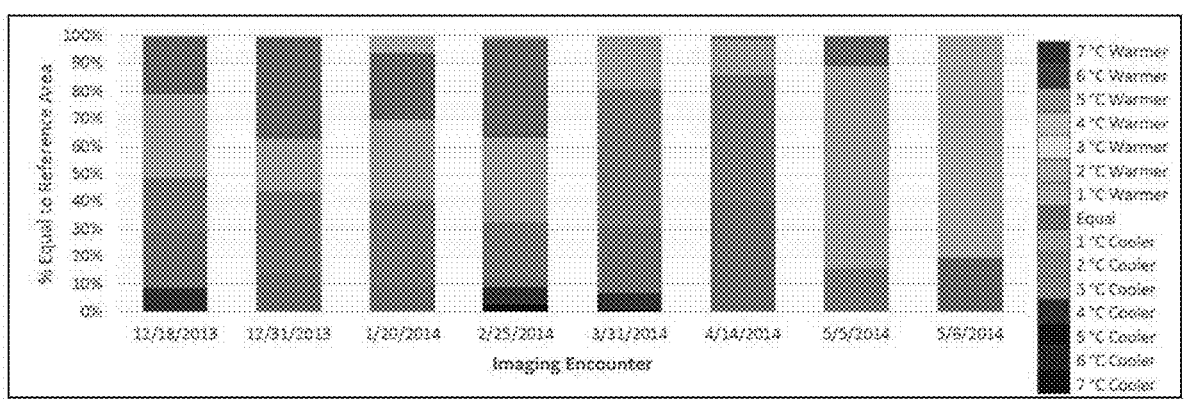

FIG. 53 shows: A plot periwound temperature gradiency compared to a gradiency of an unaffected area.

Figure 54:
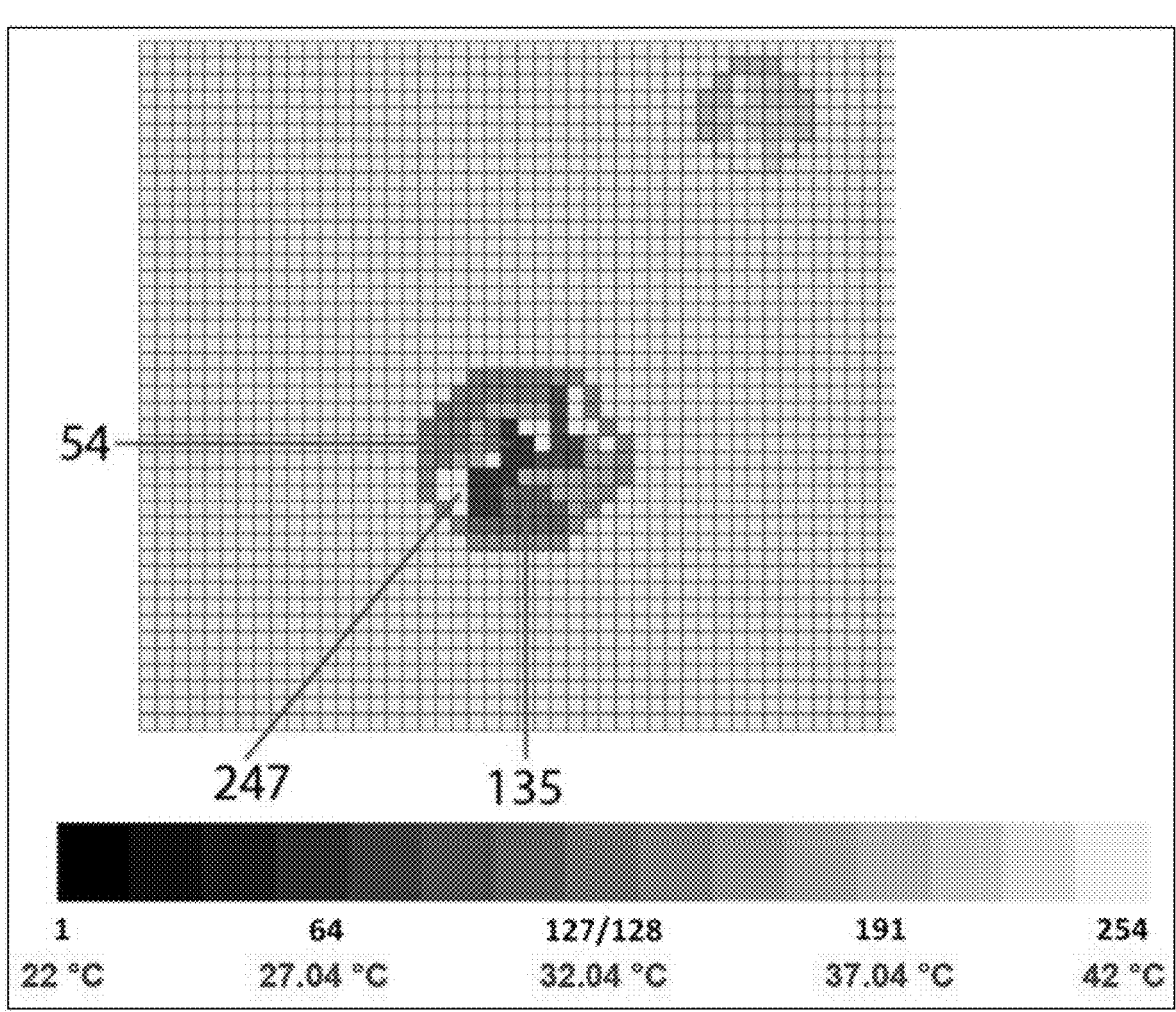

FIG. 54 shows: A schematic of pixel values applied to a thermal image of a wound.

FIG. 55 includes FIGS. 55A, 55B and 55C, showing photographic comparisons between non-relative thermal images and relative thermal images. FIG. 55A shows: A non-relative grayscale thermal image.

FIG. 55B shows: A non-relative iron color scale thermal image.

FIG. 55C shows: A relative color scale thermal image.

Figure 56:

FIG. 56 shows: Trace of visual wound edge.

Figure 57:
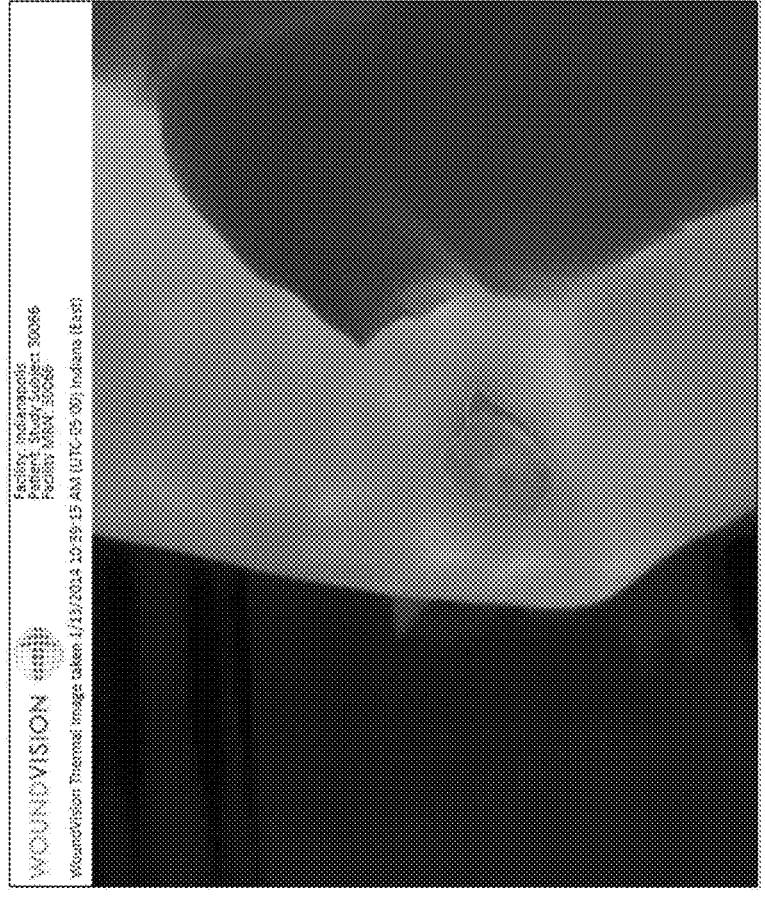

FIG. 57 shows: Traced wound edge on thermal.

Figure 58:
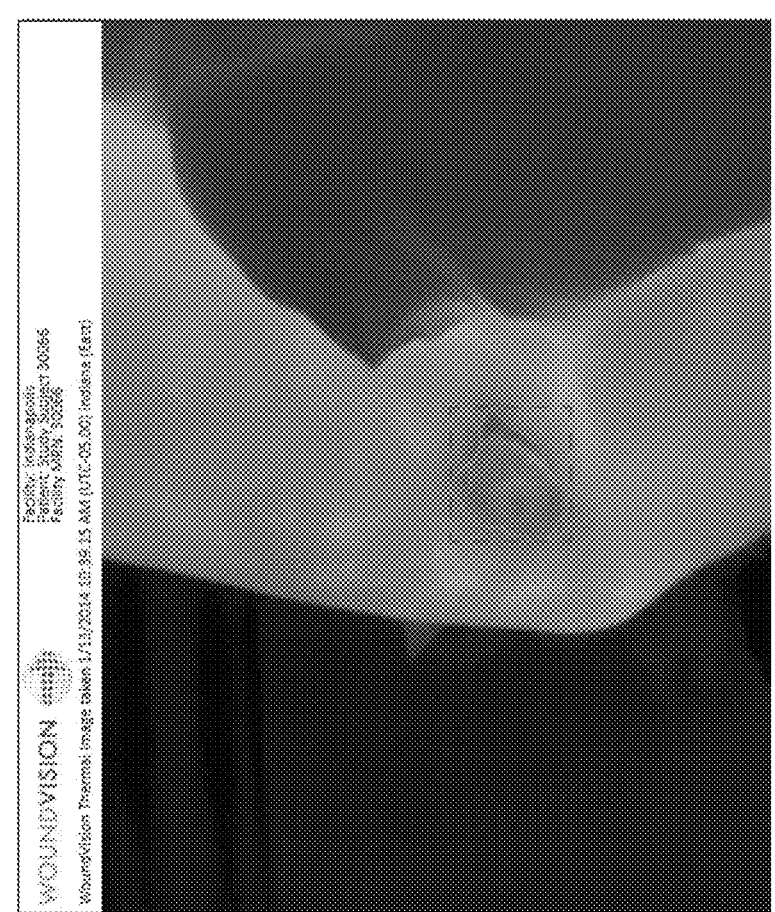

FIG. 58 shows: Center point of wound based on overlaid trace.

Figure 59:
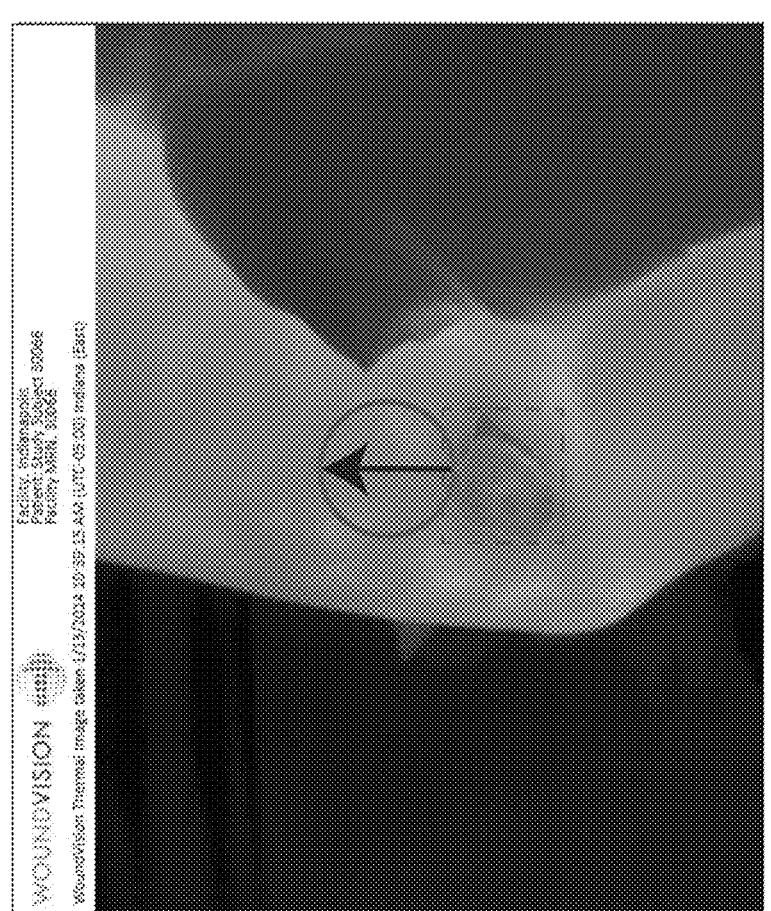

FIG. 59 shows: Head direction of wound selected based on visual or thermal image.

Figure 60:
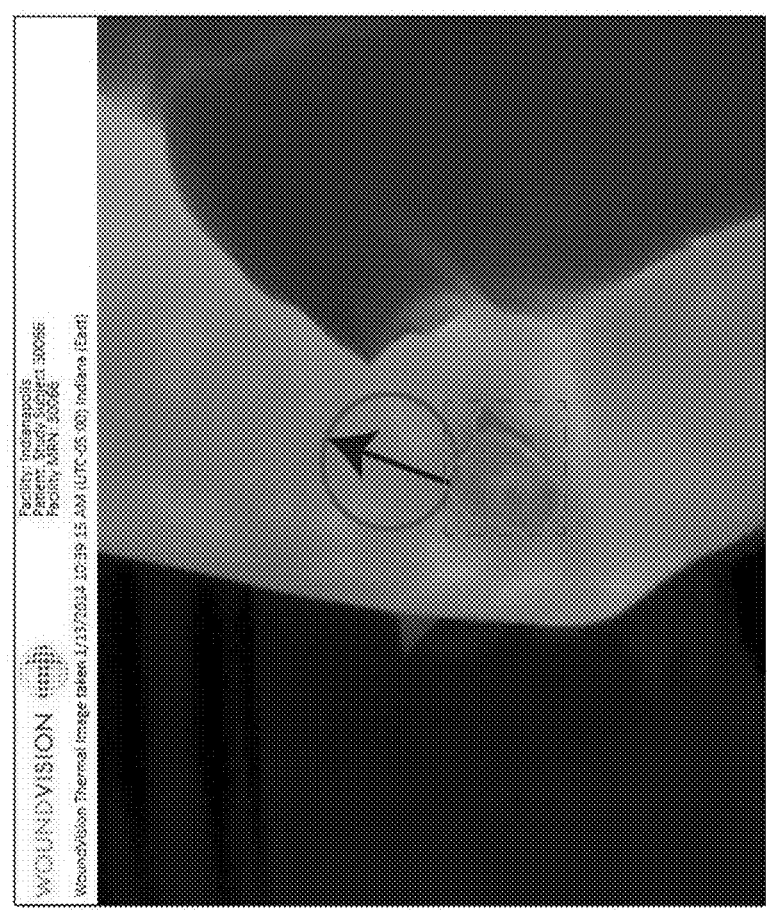

FIG. 60 shows: Head direction of wound selected based on visual or thermal image.

Figure 61:
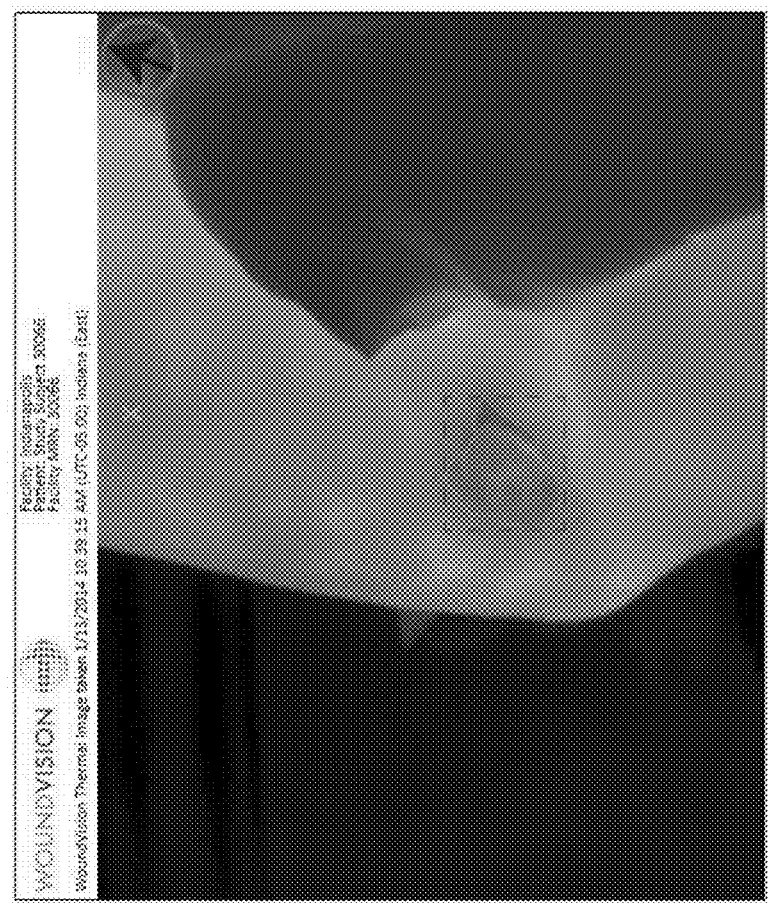

FIG. 61 shows: Reference area for software selected on thermal image.

Figure 62:
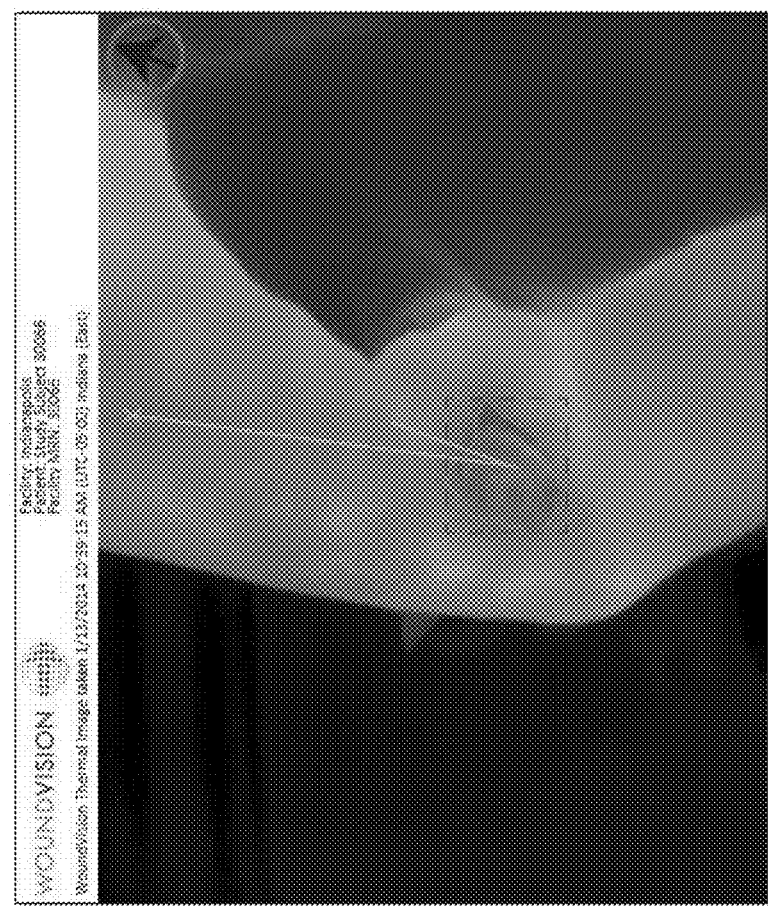

FIG. 62 shows: Distance from vertex to reference area on first day.

Figure 63:

FIG. 63 shows: Distance from vertex to reference area on second day.

Figure 64:
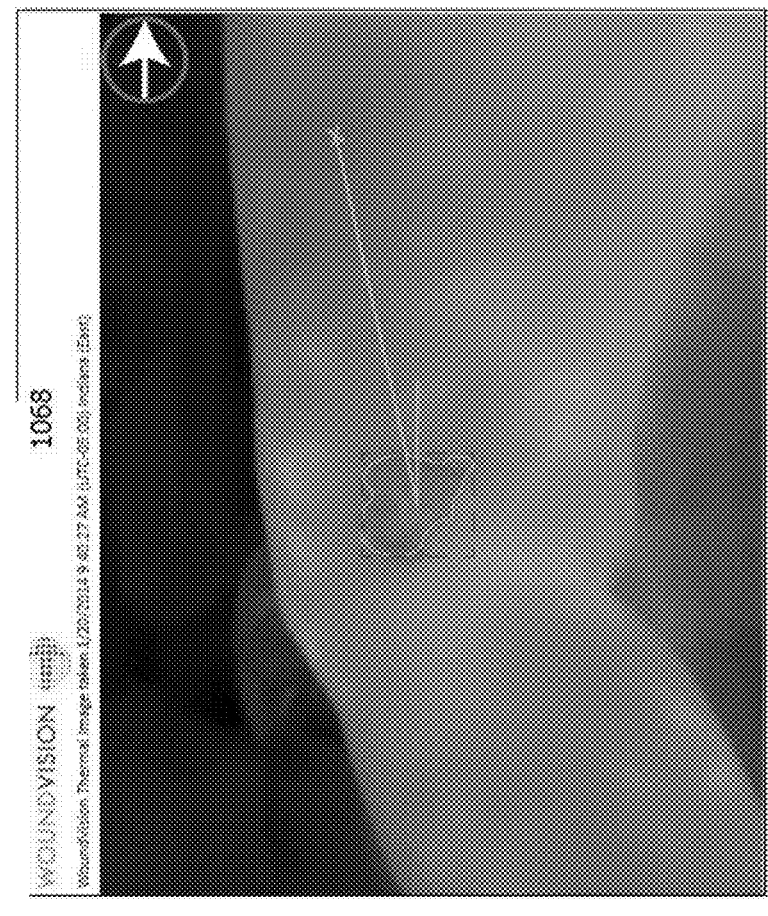

FIG. 64 shows: Distance from vertex to reference area on third day.

DETAILED DESCRIPTION OF THE EMBODIMENTS

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations.

All of the implementations described below are exemplary implementations provided to enable persons skilled in the art to make or use the embodiments of the disclosure and are not intended to limit the scope of the disclosure, which is defined by the claims. In the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Accurate and repeatable measurement of size is essential for documenting progression or regression of the wound and/or area of interest. The long-accepted standard of wound and/or area of interest measurement is to multiply the length of the wound and/or area of interest by its width. However, this method has been shown to have significant errors when used to compare the results of one observer to another. The present invention provides a system and method of tracing the wound and/or area of interest edge on a visual image to provide clinicians with both measurements of wound and/or area of interest area and perimeter. The present invention further comprises a system and method for using long wave infrared thermography to analyze physiological aspects such as perfusion and metabolic activity as measured by the effect of a body surface temperature. In another aspect of the present invention there is disclosed a new combination of digital and long wave infrared thermography cameras to simultaneously capture a visual and infrared image of a wound and/or area of interest and surrounding body surface.

Using the system and methods of the present invention, a visual image is captured and used to document the appearance of a wound and/or area of interest, trace the wound and/or area of interest's edge, and determine the area and perimeter of the wound and/or area of interest. Simultaneously, a long wave infrared thermographic camera is used to provide insight into the physiological functions of a wound and/or area of interest and surrounding body surface. The present invention thus includes means for a trace around an area of interest on a visual image of a wound and/or area of interest to be overlaid onto the congruent thermal wound and/or area of interest shown by the long wave infrared thermographic camera.

The present invention further comprises using long wave infrared thermography as a temperature measurement technique for the visualization and quantification of thermal energy emitted by the human body surface. When using long wave infrared thermography, thermal energy is represented through a unique conversion of gray scale pixel values to temperature values. The gray scale pixel value is a spectrum of absolute white to absolute black where pixel value of one (absolute black) is the coolest and a pixel value of 254 (absolute white) is the warmest. Since the imaging device of the present invention is calibrated to within a range of 22 to 42 degrees Celsius, it is able to detect temperature differentials within 0.08 degrees Celsius.

Advantageously, the system and methods of the present invention do not provide absolute measurements of temperatures. Instead, the system and method of the present invention allows clinicians to measure and record the temperature of a wound and/or area of interest area of interest and compare that to known unaffected areas on the patient. Thus, the effects of intrinsic and extrinsic variables that affect absolute temperature on a given day and make absolute measurements unreliable for clinical purposes especially when taken across different days or by different clinicians are avoided. Some of these intrinsic variables include the normal cycle of thermal production, age, chromatic morbidities, body region, medications, core temperature and others. Extrinsic variables including ambient temperature, humidity, air convection, climate adaption of the tissue, configuration of the body surface, sub straight temperature of the infrared core.

When assessing temperature data from multiple points in time, it is essential that the intrinsic and extrinsic variables described above are minimized. To accomplish this, selection of an unaffected area on a body surface can be used as a control relative to an affected area or likely affected area such as a wound and/or area of interest area of interest. Because the control is exposed to the same intrinsic and extrinsic variables as the affected area, a comparison of the two makes them independent of such variables. Since the temperature data can vary between body regions however it is important that the selection of the control area occur on or near the same body surface of the area of interest.

In combinations with other clinical information, clinicians are provided with relative quantitative data and relative qualitative data as shown in FIG. 55. Measurements of relative temperature differentials can allow clinicians to accurately and reliably evaluate wound and/or area of interest areas of interest by comparing the same over time through ratio analyses, graphs, and algorithms to unaffected areas thus eliminating the variables that might affect the accuracy of such measurements at a single point in time.

In the present invention, thermal images taken of the body surface are constructed by passively reading emitted radiant energy formed by the underlying tissue and the skin tissue by detecting wavelengths in the long-wave infrared range (LIR) of 7-14 microns, and then in real time converting these values into pixels within a digital image. The value assigned to the pixel indicates the thermal intensities of a particular area of the skin when imaged. Thermal images are presented in digital 8-bit grayscale with pixel values ranging from 0-254. Generally, the unaffected skin thermal intensity will be a uniform gray color within a range of +/−3-to-6-pixel values, which is equal to 0.25 to 0.5 degrees centigrade. Abnormally hot areas of the skin will be represented by patches of increasingly white pixels, while abnormally cold areas will be represented by increasingly dark patches of pixels.

These same techniques work with images of varying color resolutions.

These images are preferably stored in a data bank along with information about the data that can be retrieved by a clinician for future review and analysis.

The use of LIR (7-14 microns) imaging along with visual digital imaging allows both physiologic (long-wave infrared and visual) and anatomic assessment of skin and underlying tissue abnormalities and or existing open wound and/or area of interests. The gradiency of the thermal intensity, not the absolute amount of intensity, is the important component of the long-wave thermal image analysis that will allow the clinician to evaluate pathophysiologic events. This capability is beneficial to the clinician in the prevention, early intervention and treatment assessments of a developing existing condition caused by, but not exclusively, wound and/or area of interests, infection, trauma, ischemic events and autoimmune activity.

As stated previously herein, utilizing absolute temperature values (P, C0, and Kelvin) as the numerical values of LIR thermal heat intensity is complicated due to the need to have a controlled environment. This is required since the value of the absolute temperature scales is affected by ambient temperature, convection of air, and humidity. These variables would need to be measured and documented continuously if temperature values were used. Also, the emissivity, absorptivity, reflexivity and transmitability of the skin and underlying tissue can be affected by skin moisture, scabbing, slough and/or eschar formation in an open wound and/or area of interest.

The thermal imager of the present invention utilizes raw data captured by a microbolometer. This data is utilized in determining pixel values relating to the intensity of the thermal energy from the long-wave infrared electromagnetic radiation spectrum being emitted by the human body. The pixel gradient intensities are represented for visualization by the grayscale presentation.

The pixel values in the grayscale thermal images also vary with the varying conditions mentioned above and hence the algorithms proposed in this application use the average pixel value of the unaffected skin region for that patient on the day the image was taken as a reference point for all the calculations.

There is a difference in the LIR thermal intensity regions of the human body. LIR images have a defined pixel intensity range that is based on the specific usage of an LIR image. In the arena of skin and underlying tissue LIR thermal gradiency, the range is within homeostasis requirements to sustain life. The visualization of pixel intensities is accomplished by the use of a standardized 8-bit grayscale. Black defines cold, gray tones define cool and/or warm and white defines hot. When the imager is used for capturing extremely hot or extremely cold regions that fall outside the thermal range of the imager, the pixel values reach the saturation point, and it becomes extremely difficult for the human eye to differentiate variations in the pixel values.

Visual and thermal imagers used in the imaging apparatus of the present invention don't have the exact same field of view. Hence, the digital visual and thermal images cannot be overlaid automatically. To help the user with positioning the overlay image, the present invention comprises image alignment line feature by which a user can draw a line tracing the edges of an area of interest of a body part seen in a visual image. A transparent image is created showing the area traced on the visual image which is then overlaid on top of a thermal image. When creating the transparent overlay image, the lines along with the trace will be included. Since the edges of the human body are clearly distinguishable in a thermal image, having an alignment line, described herein below, along with the trace, provides visual aid in deciding the proper positioning of the overlay.

Referring to FIG. 2, once the trace has been placed around the area of interest on the visual image, for each coordinate along the trace, by adding the X and Y shift, the corresponding X and Y coordinates on the thermal image can be obtained. A transparent image is created, and a trace is drawn using the new X and Y coordinate and is overlaid on top of the thermal image as shown in FIG. 3, allowing the user to position it if needed before dropping the trace on the digital image.

When the user confirms the position where the trace needs to be dropped in the thermal image, the overlay image is removed, and the trace is placed on the thermal image itself as shown in FIG. 3.

Long wave infrared thermography captures thermal images that can provide insight into the physiological functions of the wound and/or area of interest and the surrounding body surface. They provide more in-depth information than an image captured using a regular digital camera. The method of the present invention comprises software means that allow the user to trace an area of interest and obtain several measurements including for example temperature gradiency within the wound and/or area of interest which is helpful in tracking the progression or regression of the area of interest.

Thus, the system and methods of the present invention allow a user to analyze a pair of thermal and visual images to obtain an in-depth understanding of the status of an area of interest on a patient. Using the present system and methods a trace is drawn around an area of interest on a visual image representing. The area and perimeter for the traced area are calculated and displayed as results. The traced area on the visual image is then overlaid on a thermal image.

The thermal core, however, of a camera according to the present invention is likely to produce an image with barrel distortion. In barrel distortion, image magnification decreases with distance from the optical axis. The apparent effect is that of an image which has been morphed around a sphere or a barrel. In order to correct for barrel distortion, several different methods may be used. However, in the present invention, it's preferable to use the lens distort algorithm available in MATLAB. The algorithm takes as input the original distorted image as well as additional parameters and generates as output a barrel distortion corrected image. The method of accomplishing this is shown in Appendix 1. Those of skill in the art will appreciate that the color scale has a degree of predetermined "grouping" to enhance visual clarity.

The barrel distortion corrected image is then adjusted for Keystone correction. In order to make sure that both cameras are pointing at the same field of view, the thermal camera is installed at an angle which produces a Keystone effect on the images. The Keystone effect algorithm developed in MATLAB takes the input image that needs to be corrected and the amount of blank space and generates the corrected images as output.

Thus, when the images are opened, the system of the present invention incorporates software means for correcting the images for barrel (and Keystone) distortion before the images are displayed on a screen for the user. The distortion correction software is applied each time the images are opened, but the original image data is never altered. In the preferred embodiment of the present invention, the only data stored in the database is the original images. The parameters used for the distortion correction are specific to each calibrated image capture device.

The image capture device of the present invention may further incorporate means for live video stream image capture from the thermal camera. Visual and thermal captured images may be displayed and stored (in grey scale, another color scale, or in a specific pixel value scale) simultaneously. The image is captured or stored in a database in their original format, i.e., without distortion correction. Distortion correction is not applied until the image is uploaded and pulled from the database for review.

A trace has been drawn around an area of interest on the visual image for later study. For each coordinate along the trace, by adding the X and Y shift, the corresponding X and Y coordinates on the thermal image can be obtained. A transparent image is created, and a trace is drawn using the new X and Y coordinates and is overlaid on top of the thermal image allowing the user to position it if needed before dropping the trace onto the thermal image. The user confirms the position where the trace needs to be dropped on the thermal image overlay. The overlay image is then removed and the trace is drawn on the thermal image itself.

To help the user with positioning the overlay image, an image alignment line feature is incorporated into the system of the present invention to allow the user to draw a line tracing the edges of the body part on the visual image. When creating the transparent overlay image, the line along with the trace is included. Since the edges of the human body are clearly distinguishable in a thermal image, having an alignment line along with a trace provides visual aid in deciding the proper positioning of the overlay. Once a trace has been drawn on the thermal image an unaffected reference point can be selected. To help with the process of selecting an unaffected reference point, a gray scale or iron scale thermal mosaic is applied to the thermal image. Grey scales (or other color scales, such as "iron") are used for "unbundled" raw data. "Bundled" data uses a single reference point rather than a reference area.

An area of interest needs to be traced before the unaffected reference point can be selected. The mean or average pixel value of the traced area is used as a reference. For the thermal images captured using the devices disclosed in the present invention, a pixel value difference of preferably about 12 represents a one degree Celsius change in temperature. All of the pixels whose pixel values fall within the range of a mean of plus or minus six are considered suitable to be selected as a reference point. A different color is used for representing each degree change in temperature. White is generally used to represent hot, and black generally represents cold in the preferred embodiment. However, those with skill in the art will appreciate that any colors may be chosen. Similarly for the R G B scale it is preferred to use red to represent hot and green or blue to represent pixels that are colder than the reference area.

To select an unaffected reference point a user of the system of the present invention should check whether a thermal trace exists. If yes, check to see whether pixels fall inside the trace and use the pixel values of all those pixels to calculate the average pixel value, decide on the color codes that represent each temperature interval, for example 15 different shades are chosen for the color scale, then use the base color that falls within the color scale to highlight all pixels within a pixel mean value of between plus and minus six. Appendix 2 shows the logic used to color the rest of the pixels.

After reviewing the images by drawing traces and obtaining measurements out of these traces, a particular session with regard to a particular patient may be saved. The system of the present invention can generate visual or graphical or tabular results based on the images obtained and the calculations made. FIGS. 32-43 show various representations of the steps of the methods described above.

FIG. 44 shows an exemplary logic model for the visual overlay trace and the wound and/or area of interest sight trace aspects of the present invention. In FIG. 46 shows a profile line plot according to the method of the present invention. FIG. 45 shows a visual representation on a patient of the profile line plot shown in FIG. 46.

FIGS. 47 through 53 show various graphical representations of the calculations that can be performed by the system in methods of the present invention.

The periwound is defined as the skin and all underlying tissue surrounding contiguously with the area that is recognized as the wound and/or area of interest base. Abnormalities of this tissue can be clinically or non-clinically recognizable. The periwound should be considered a deep tissue injury prone area. Accordingly, the periwound is an ideal area of interest for a trace on the visual image of a wound and/or area of interest.

The periwound is the tissue surrounding the wound and/or area of interest itself. This tissue provides an access corridor for blood, etc. to the wound and/or area of interest, for healing and progress. Complications to this ideal function come because periwound tissue can be adversely affected by infection prolonged inflammation; poor blood supply; poor metabolic activity. It is important to clean the area of the wound and/or area of interest and monitor the status of the wound and/or area of interest and periwound including the skin and underlying tissue. Even using the infrared thermographic images sometimes it is difficult to trace the edges of a periwound as the periwound region does not have an abrupt change in thermal intensity due to infrared radiation versus visual. Instead, it slowly fades into the unaffected portion of the skin.

To assist clinicians in choosing the periwound accurately, the following technique was developed:
1. Trace the area of interest or the visual image;
2. Overlay the trace from visual image onto the thermal image. The overlaid trace can now be treated as the wound and/or area of interest base;
3. Allow the user to specify the distance in centimeters, generally 1 to 5 centimeters, between the wound and/or area of interest base edge and the periwound edge;
4. Using the coordinates of the wound and/or area of interest base and the distance information a new set of coordinates can be calculated that represent the corners of the periwound.

To highlight the abnormal area of interest in a visual image:
1. Start tracing the area of interest by clicking on the image; see the X and Y coordinates of the click points.
2. Use the mouse, or other input device to draw lines connecting the adjacent points on the computer screen.
3. When the user double clicks the mouse join the last point of the first point which finishes up the trace.
4. Using each click point as a coordinate determine which pixels fall inside the polygon area representing the trace. The trace now represents the wound and/or area of interest base region as shown in FIG. 3.

Once the wound and/or area of interest base area has been traced, the user is given an option to provide the distance between the wound and/or area of interest base and the periwound regions. The user can specify the distance in centimeters or any other convenient set of measuring units. By knowing the distance at which the image was captured, we can convert the distance in centimeters to distance in pixels. For example, we know that for a thermal image captured at 18 inches, there would be approximately 40 pixels in an inch. So, if the user says the distance between the periwound base and the periwound traces is 1 centimeter, we can calculate the corresponding number of pixels between the two traces.

The wound and/or area of interest base can be considered as a polygon where each coordinate corresponds to a corner. The new coordinates of the periwound can be calculated by offsetting the polygon for a distance equal to the distance (in pixels) between the two traces. The Clipper Library was used for performing polygon offsetting. This library is based on Vatti's clipping algorithm. FIG. 4 shows the periwound trace obtained by offsetting the wound and/or area of interest base polygon by 1 centimeter in all directions.

Since the polygon is offset by the same amount in all directions, there are chances that a portion of the periwound trace may fall outside the desired area (for example the trace may coincide with the background or other portions of the body that do not comprise the periwound. As a work around for this problem the user can either manually resize the periwound trace by altering the position of one or more of the coordinates, or choose to exclude a certain portion of the trace that falls outside the desired area.

Wound and/or area of interest base and periwound together are considered as the wound and/or area of interest sight. The status of these traces can be monitored on a daily basis in comparison to previous measurements to assess whether the wound and/or area of interest is getting better or getting worse.

The periwound is defined as the area of skin surrounding a wound and/or area of interest. The periwound can be traced on the thermal image produced by the systems and methods of the present invention then overlaid on the visual image. The area and perimeter of the periwound can then be calculated relative to the visual image.

The system checks to ensure that the periwound trace does not overlap or fall outside the trace representing the base wound and/or area of interest. Periwound calculations include only the pixels that fall inside the outer thermal trace but not inside the wound and/or area of interest bed trace. The combination of the two is the wound site, as shown in FIG. 31.

A control unaffected area is chosen which allows for a true relative temperature comparison between an unaffected area and areas of interest. Relative temperature gradients above about 1.5 to 2 degrees Celsius are known to indicate significant physiological aberrations. Possible causes for these aberrations may include hyperthermia caused by inflammation or infection or hypothermia caused by poor perfusion and/or tissue necrosis. The present invention allows means to display the visual and thermographic recorded data concurrently in a quantitative and organized sequential format while storing the objective data for future reference.

Combining the above technique with suggested usage of unaffected skin and underlying tissue in the proximity of an abnormality of a skin/underlying tissue location as a real time control helps to minimize the variability and time-consuming requirements in utilizing temperature scales.

Choosing a controlled unaffected reference area ("CUA") allows for a minimization of intrinsic and extrinsic variables for the accurate determination of the relative temperature gradiency between the wound and/or area of interest base, periwound, or entire wound and/or area of interest sight in reference to the CUA. Relative temperature gradients greater than 0.5 degrees Celsius are known to indicate significant physiological aberrations. Possible causes for hyperthermia include inflammation, infection. Possible causes for hypothermia include poor perfusion, tissue necrosis, poor metabolic activity; inflammation. Using the systems and methods of the present invention visual and thermal recorded data are displayed in human readable form in a quantitative and organized sequential format. This thermal data allows for the objective assessment of relative parodies and disparities between the wound and/or area of interest base, periwound, and entire wound and/or area of interest sight. This data, combined with other information provided by the systems and methods of the present invention allows a clinician to save and record quantitative measurements from both an anatomical and physiological perspective that may otherwise go unseen.

As stated previously, an unaffected reference area needs to be chosen such that the temperature variation ("gradiency") across the area is less than 1.5 degrees Celsius. In order to aid with the selection of reference area, features like a "profile line" and "color mosaic" provided in the software can be used.

The portion of the plot shown in FIG. 10 where the various in temperature is less than 1.5 degrees Celsius represent the suitable position for selecting the unaffected reference area. The plot is user interactive, so the user can click on the chart to highlight the point on the image and vice versa.

A profile line is another tool provided by the systems and methods of the present invention that can be used to aid the user in selecting the unaffected reference point. Profile line plots show the variation in the pixel values across the line drawn at the top of the wound and/or area of interest. Since the thermal intensity is directly related to the gray scale pixel values in an image, these plots can be used to monitor how the thermal intensity is varying across the areas of interest.

Profile lines can be plotted by simply drawing a line across an area of interest. FIG. 9 shows an example of the profile line generated by drawing a line starting from the center of the wound and/or area of interest base to a point that represents unaffected skin. As seen in the plot, there is a huge drop in the pixel value/thermal intensity across the wound and/or area of interest base region and the value starts increasing as the line is moving away from the wound and/or area of interest base and entering the areas with normal skin tissue.

FIG. 11 shows an unaffected reference area chosen using the profile line plot. The area of interest can be traced as seen on the visual image and then overlaid onto the thermal image. The results of the wound and/or area of interest trace along with the information about head direction and unaffected reference area can then be used to predict the suitable position for placing the reference point on the images captured at future times.

Automating the process of selecting a reference point based on the information provided makes the reference point selection more consistent and eliminates variation between users evaluating patients on different dates. An algorithm used in the present invention for selecting a reference point comprises of the following steps:

1. Selecting a direction of the head on a visual image;

2. Overlaying an external wound and/or area of interest trace drawn on the visual image onto a thermal image or performing a thermal wound and/or area of interest trace on the thermal image;

3. And manually selecting a reference area on the thermal image.

Referring now to FIG. 12 there is shown a visual representation useful in performing the calculations for selecting a reference point. The method of selecting a reference point includes calculating the distance between the center point of the external wound and/or area of interest trace and the manually selected reference area. Since the wound and/or area of interest trace is a polygon, to find the center of the polygon one must first find the minimum and maximum x coordinates along the horizontal axis and the minimum and maximum y values along the vertical axis. The distance between the center of the wound and/or area of interest trace polygon (x1, y1) and the center of the reference area (x2, y2, as shown in FIG. 12, can be calculated using a standard distance formula where the distance equals the square root of (x2-x1) squared plus (y2-y1) squared. Next the angle formed between the selected head direction relative to the line joining the center point of the overlaid external wound and/or area of interest trace from the thermal image to the manually selected reference area is calculated. With reference to FIG. 13, in order to calculate angle B, angles H and A need to be calculated. H is the head direction angle, and A is the angle made by the line joining the center of the wound and/or area of interest trace and the center of the reference point which can be calculated as follows: Ifx1, y1 represent to the center of the wound and/or area of interest trace and x2, y2 represent to the center of the reference point, then the slope of the line can be calculated using traditional geometry as the slope equals y2–y1 divided by x2–x1. Since the slope can also be defined as tangent of angle A, angle A can be calculated as A equals tan superscript negative one times slope. Once angles H and A are known, angle B, can be calculated as B=A–H.

Thus in setting an automated reference area the user must set the head direction on the visual image; overlay the external wound and/or area of interest trace and place it onto the thermal image or perform a thermal wound and/or area of interest trace on the thermal image; identify the automated reference area feature then confirm the system determined automated reference area or manually place the same.

Based on user's current selection of head direction and the center point of the overlaid external wound and/or area of interest trace from the thermal image, the system of the present invention approximates the location of prior reference areas as shown in FIG. 14.

Again, as shown in FIG. 14, if "$H_{new}$" is a new head direction angle for the current session, based on the information from previous sessions the system of the present invention can determine the relative angle between the head direction line and a line joining the center of the wound and/or area of interest trace to the center of the reference point (B). Using the following formula: Theta=$H_{new}$+B, thereby giving the angle of the x axis.

For the imaginary line joining the center of the wound and/or area of interest trace to the center of the automated reference point, we know the starting point of the line which would be the coordinates of the center of the wound and/or area of interest trace, the angle made by the line along the x axis (Theta) and the length of the line, which is equal to the distance between the center of the wound and/or area of interest trace and the center of the pre-selected reference point. Using this information, the end point, the coordinates of the automated reference point, can be calculated as shown in FIG. 15.

User of the present invention is preferably given an option to either use the automated reference area selection or to manually select a new area. If the user chooses to use a manual selection instead, that manual selection now becomes the baseline. The user does not have to use the automated reference area. The user could perform a manual selection each time the system and methods of the present invention are used.

FIGS. 16 through 24 herein display the various steps described in the previous paragraphs for determining an automated reference area.

"Profile lines" can also be drawn to help with the selection of an unaffected reference point. Profile lines are freeform lines drawn across the image. The profile line plots display the variation in temperature along the line. If the line is flat, it indicates the temperature gradiency variation is very low and it is a suitable location for selecting the unaffected reference point. The user can click on the plot and the corresponding location on the image is highlighted by the system of the present invention. A user can then place the unaffected reference point in that location or choose a different one if the user so desires.

Even though the thermal images provide more in-depth definition of area of interest than the digital image, it becomes harder to differentiate between small variations in temperature as it is difficult to differentiate between shades of gray. The entire thermal image is made up of 254 different shades of gray as shown in FIG. 5.

To make visual differences between temperature variations greater the method of the present invention includes incorporating a unique color for each pixel value to generate a custom color bar as shown in FIG. 6. The custom color bar shown in FIG. 6 was developed using MATLAB'S color bar editor.

To apply the custom color bar to the gray scale thermal image, the present invention incorporates the following algorithm:
1. Generate a matrix that holds the R, G, and B values of 254 different colors representing pixel values ranging from 1 to 254;
2. Obtaining the pixel value for each pixel in the image;
3. Finding the corresponding color for that pixel value;
4. Setting the pixel value for that pixel to the new color;
5. Applying the new color scale to the entire image;
6. Displaying the new image blended with the new color scale.

Unmanaged code can be used to make the above-explained process faster. FIGS. 7 and 8 below show the thermal images before and after applying the blended custom color scale described above.

By looking at either the original gray scale thermal image or the image with the color scale, unaffected reference area tissue can be selected at a location that represent unaffected skin with less temperature variation.

As the wound and/or area of interest starts healing, the differences between the pixel value for the unaffected tissue and the pixel value from the wound and/or area of interest base starts decreasing and hence the drop scene in the graph of FIG. 10. The decrease in temperature shown in FIG. 10 indicates that a wound and/or area of interest is healing and is starting to get closer to the unaffected skin tissue.

If the drop in the pixel value starts increasing, when plots are generated for images taken on a timely basis, then it is an indication that the wound and/or area of interest is deteriorating and the clinician needs to turn to strategies to facilitate wound and/or area of interest healing.

The thermal mosaic is the colored representation of a gray scale thermal image. It shows the variation in pixel values using different colors. Even though thermal images provide more in-depth definition of area of interest than the digital image, it becomes harder to differentiate between small variations in temperature as it is difficult to differentiate between shades of gray. The entire thermal image is made up of 254 different shades of gray as shown in FIG. 25.

However, to make the visual representation of the thermal image clearer, the present invention also provides for a custom color representation of the thermal image. To accomplish this each gray scale pixel value is assigned a specific pixel value using the MATLAB color bar editor as shown in FIG. 26.

To apply the custom color bar FIG. 26 to a gray scale thermal image the following steps are performed:

1. Generating a matrix is that holds the R, G, and B values of 254 different colors representing the pixel values ranging from 1 to 254;
2. For each pixel in the image obtaining the pixel value;
3. Finding the corresponding color for each pixel and setting the pixel value for that pixel to the new color;
4. Looping the image to apply the new color scale; and
5. Displaying the new image with the blended color scale.

FIGS. 27 and 28 show before and after images respectively for the blended color scale.

Using the original gray scale image or the image with the custom color scale applied, an unaffected reference area can be chosen which can be used for tracking the progression or regression of an area of interest.

Once the reference area has been chosen, another custom color scale option can be provided where the mean pixel value of an unaffected reference area is used as a reference and is represented in a particularly desirable color. For example green. Using the new color scale all the pixels in the image can be viewed relative to the selected unaffected reference area. If an area of interest is warmer than reference it will be assigned a color closer to the warmer end of the color scale and vice versa. FIG. 29 shows a new custom color scale that takes unaffected reference area into consideration.

A method for applying a custom color bar to the gray scale thermal image comprises choosing an unaffected reference area such as the temperature variation within the area is less than 1.5 degrees Celsius, finding the average of all the pixel values that fall within the unaffected reference area called the reference mean; generating a matrix that holds the R, G, and B values for the new custom colors; assigning each pixel in the image a pixel value; and calculating the difference between the current pixel value and the reference mean. Using the formula difference in pixel value equals current pixel value minus reference mean. Finding the R G B, color that corresponds to the difference in pixel value and setting the pixel value for the pixel to the new color; looping the whole image to apply the new color scale; and displaying the resulting image with the blended color scale.

As shown in FIG. 30, all the portions of the image that have a temperature equal to the unaffected reference area are presented with the same color in this case green. Using the above color scale as a reference, and by comparing the color of an area of interest with an unaffected reference area, a clinician can get a clear understanding of how much cooler or warmer an area of interest is with respect to the reference area.

By monitoring the images on a scheduled basis and choosing a reference point consistently between the images a clinician is able to see a pattern in which the temperatures across the area of interest are changing. By monitoring changes in colors over time a clinician is able to visually to interpret whether the wound and/or area of interest is getting better or worse.

Thermal mosaic is the colored representation of the thermal image. It shows the variation in pixel values using different colors. Gray scale colors are used for the thermal mosaic before the unaffected reference point is selected, an R G B color scale is used after the selection is made.

Once a reference point or reference area is selected, the color mosaic can be turned on for the whole image and use that as a visual aid for drawing the periwound trace. In order to generate the color mosaic, the mean or average pixel value of the unaffected reference point or mean pixel value of the unaffected reference area is used as the mean in the algorithm for generating a thermal mosaic. Since the reference point is just one pixel, there is only one pixel value. If each time a user engages the system a different reference point is selected needless variation will be introduced. Since just one pixel is used as a pixel value, a reference mean is used instead to generate the color mosaic using the methods disclosed in Appendix 3 attached hereto.

The thermal mosaic can be turned on or off for each trace separately. Using this information, clinicians can calculate using this system the difference in thermal intensity within the wound and/or area of interest in degrees Celsius or degrees Fahrenheit; the percent of pixels that fall within a particular pre-determined range of the unaffected reference area; the minimum temperature compared to an unaffected reference point; the maximum temperature compared to an unaffected reference point; or a mean temperature compared to an unaffected reference point.

Baseline Reference Area User Requirements

User must set head direction on the visual image (can be obtained from either current Lx W function or the addition of a Set Head Direction only function)

User must either overlay an External Wound Trace and place it onto thermal image or perform a Thermal Wound Trace on the thermal image A manual Reference Area must be selected using the current functionality Baseline Database Requirements Angle formed from the selected head direction relative to the center point of the overlaid External Wound Trace or Freeform Wound Trace from thermal image and the manually selected Reference Area Distance from the center point of the External Wound Trace or Freeform Wound Trace to the manually selected Reference Area Automated Reference Area User Requirements User must set head direction on the visual image (can be obtained from either current LxW function or the addition of a Set Head Direction only function)

User must either overlay an External Wound Trace and place it onto thermal image or perform a Thermal Wound Trace on the thermal image User must click the Automate Reference Area button User must either confirm they agree with automated placement or disagree and place it manually.

Automated Reference Area Database Requirements

Recall of angle formed from the selected head direction relative to the center point of the overlaid External Wound Trace or Freeform Wound Trace from thermal image and the manually selected Reference Area from the most recent session with a manually selected Reference Area Recall distance from the center point of the External Wound Trace or Freeform Wound Trace from the most recent session with a manually selected Reference Area Based upon the user's current selection of head direction and the center point of the overlaid External Wound Trace or Freeform Wound Trace from thermal image, an approximation of the location of prior Reference Areas can be determined Miscellaneous User disagrees with Reference Area Automation and manually selects a new area; this manual selection now becomes the baseline.

User does not have to user Automated Reference Area; a user could do the manual selection every time.

APPENDIX 1

If selecting unaffected reference point:
1. Check whether thermal trace exists
2. If yes, check to see which pixels fall inside the trace and use the pixel values of all those pixels to calculate the average pixel value (mean). If not stop
3. Decide on the color codes that represent each temperature interval change. Fifteen (15) different shades were chosen for the color scale. Gray scale colors are used before the reference point is selected.

4. Use the base color that falls in the middle of the color scale to highlight all the pixels with a pixel value between mean−6 and mean+6. The following logic was used to color rest of the pixels

5.

```
if(PV <(Mean− 6− (6 '"PI)))
{
Highlight the pixels using the color'that falls in the bottom of the scale representing the coldest
pixels
}
else if (PV >=(Mean − 6 − (6 *PI)) & PV <(Mean− 6 − (5 *PI)))
{
Highlight the pixels using the color that is second from the bottom of the scale
}
else if (PV >=(Mean − 6 − (5 * PI)) & PV <(Mean− 6 − ( 4 * PI)))
{
Highlight the pixels using the color that is third from the bottom of the scale
}
else if (PV >=(Mean − 6 − ( 4 *PI)) & PV <(Mean − 6 − (3 * PI)))
{
3
Highlight the pixels using the color that is fourth from the bottom of the scale
}
else if (PV >= (Mean − 6− (3 *PI)) & PV <(Mean −6 − (2 *PI)))
{
Highlight the pixels using the color that is fifth from the bottom of the scale
}
else if (PV >= (Mean − 6 − (2 *PI)) & PV < (Mean −6 − (1 *PI)))
{
Highlight the pixels using the color that is sixth from the bottom of the scale
}
else if(PV >=(Mean − 6− (1 *PI)) & PV <(Mean − 6))
{
Highlight the pixels using the color that is seventh from the bottom of the scale
}
else ir(PV >= (Mean − 6) & PV <=(Mean + 6))
{
Highlight the pixels using the base color representing unaffected area. (Center color)
}
else if(PV >(Mean + 6) & PV <=(Mean + 6 + (1 * PI)))
{
Highlight the pixels using the coJor that is seventh from the top of the scale
}
else if(PV >(Mean + 6 + (1 *PI)) & PV <= (Mean + 6 + (2 * PI)))
{
Highlight the pixels using the color that is sixth from the top of the scale
}
else if(PV > (Mean + 6 + (2 * PI)) & PV <=(Mean + 6 + (3 *PI)))
{
Highlight the pixels using the color that is fifth from the top of the scale
}
else if (PV >(Mean + 6 + (3 * PI)) & PV <= (Mean + 6 + ( 4 *PI)))
{
Highlight the pixels using the color that is fourth from the top of the scale
}
else if (PV >(Mean + 6 + (4 *PI)) & PV <=(Mean + 6 + (5 * PI)))
{
Highlight the pixels using the color that is third from the top of the scale
}
else if (PV >(Mean + 6 + (5 *PI)) & PV <=(Mean + 6 + (6 *PI)))
{
Highlight the pixels using the color that is second from the top of the scale
}
else if (PV >(Mean + 6 + (6 * PI)))
{
Highlight the pixels using the color that falls in the top of the scale representing the hottest pixels
}
Where PV—Pixel Value and PI = pixel increment. PI is set to 13 when the mosaic needs to show
1° C. change in temperature, PI is set to 9 for 0.75° C. and 6 for 0.5° C. change in temperature.
```

APPENDIX 2

The 'lensdistort' algorithm in Matlab takes as input the original distorted image and the following parameters and generates as output the barrel distortion corrected image.

'bordertype'—String that controls the treatment of the image edges. Valid strings are 'fit' and 'crop'. By default, 'bordertype' is set to 'crop'.

'interpolation'—String that specifies the interpolating kernel that the separable re-sampler uses. Valid strings are 'cubic', 'linear' and 'nearest'. By default, the 'interpolation' is set to 'cubic'

'padmethod'—String that controls how the re-sampler interpolates or assigns values to output elements that map close to or outside the edge of the input array. Valid strings are 'bound', circular', 'fill', 'replicate', and symmetric'. By default, the 'padmethod' is set to "fill'

'ftype'—Integer between 1 and 4 that specifies the distortion model to be used. The models available are 1. 'ftype'=1: s=r.*(1./(1+k.*r));
2. 'ftype'=2: s=r.*(1./(1+k.*(r/'2)));
3. 'ftype'=3: s=r.*(1+k.*r);
4. 'ftype'=4; s=r.*(1+k.*(r.A2);

By default, the 'ftype' is set to 4.

APPENDIX 3

In order to generate the color mosaic the mean (average) pixel value of the unaffected reference point would be used as the 'Mean' in the algorithm described above for generating thermal mosaic. Since reference point is just one pixel there is only one pixel value. If that pixel value is used as the mean it introduces a lot of variation in the results. Every time a different reference point is selected, even though very close to the previously selected location the results varied a lot and were not repeatable so instead the following method was used.

1. Calculate the difference between the selected reference point pixel value and mean pixel value of the thermal trace (the value that was used for generating the gray scale thermal mosaic)

2.

$$increment = \frac{\text{Difference calculated from step 1}}{\text{Pixel Increment}}$$

Pixel Increment is set to 13 when the mosaic needs to show 1° C. change in temperature, 9 for 0.75° C. and 6 for 0.5° C. change in temperature 3. if (increment>0)

```
{
    Reference_min =(mean + 6 +((increment – 1) *Pixel Increment)) + 1;
    Reference _max= (mean+ 6 + ((increment) *Pixel Increment));
}
else if (increment= 0)
{
    Reference _min= (mean– 6);
    Reference _max= (mean + 6);
}
```

-continued

```
else if (increment< 0)
{
    Reference _min= (mean– 6 +((increment) *Pixel Increment));
    Reference _max= (mean– 6 +((increment+ I) *Pixel Increment)) –1;
}
where mean= mean pixel value of the thermal trace;
```

4. Mean (average) pixel value of the unaffected reference point can then be calculated as. Reference_mean= (Reference_min+Reference_max)/2

Reference_mean as calculated above can then be used as the 'Mean' in the algorithm described earlier for generating thermal mosaic. Use RGB color codes to generate Color mosaic.

The invention claimed is:

1. A system for determining a clinically relevant temperature differential between a predetermined area of clinical interest on the body surface of a mammal and a control area on the body surface of said mammal, said system comprising:

an image capturing device, said image capturing device comprising;

a housing, and a visual image capturing device and a thermal image capturing device disposed within said housing;

a display apparatus on which a visual image including the area of clinical interest and a thermal image, each captured by said image capturing device, are displayed; and a computing apparatus, said computing apparatus operatively connected to said image capturing device and to said display apparatus, said computing apparatus configured and operable to execute software for:

determining a temperature differential in degrees between the area of clinical interest and a selected control area on the body surface of said mammal;

modifying the thermal image to display the temperature differential; and overlaying said visual image onto said thermal image in a desired orientation on said display apparatus.

2. The system of claim 1, wherein the selected control area is within said captured visual image.

3. The system of claim 1, wherein the computing apparatus is further configured and operable to execute software instructions for calculating plane geometric features of said selected area of clinical interest, said plane geometric features including one or more of area, perimeter and coordinates of corners of said selected area of clinical interest.

4. The system of claim 1, wherein the computing apparatus is further configured and operable to execute software instructions for:

calculating plane geometric features of said selected area of clinical interest, said plane geometric features including one or more of area, perimeter and coordinates of corners of said selected area of clinical interest; and applying a unique pixel value to a specific predetermined range of temperature differentials in degrees on said thermal image.

5. A method of contemporaneously comparing an average temperature of predetermined area of clinical interest on the body surface of a mammal and a control area on the body surface of said mammal, said method comprising the steps of:

capturing a visual image of a portion of the body surface of a mammal;

capturing a thermal image of said body surface portion;

displaying said visual image and said thermal image on a display screen;

selecting a control area on the body surface portion;

determining a temperature of said control area;

selecting an area of clinical interest within said visual image;

determining a temperature of said area of clinical interest;

determining a temperature differential in degrees between said area of clinical interest and said selected control area;

modifying the thermal image to display the temperature differential; and overlaying said visual image onto said thermal image in a desired orientation on said display screen.

6. The method of claim 5, wherein the selected control area is within said visual image.

7. The method of claim 5, further comprising the step of applying to said thermal image a unique pixel value to a specific predetermined range of temperature differentials in degrees between said area of clinical interest and said control area.

* * * * *